(12) United States Patent
Stamler et al.

(10) Patent No.: US 6,884,773 B1
(45) Date of Patent: *Apr. 26, 2005

(54) MODIFIED HEMOGLOBINS, INCLUDING NITROSYLHEMOGLOBINS, AND USES THEREOF

(75) Inventors: Jonathan S. Stamler, Chapel Hill, NC (US); Andrew J. Gow, Doylestown, PA (US)

(73) Assignee: Duke University, Durham, NC (US)

( * ) Notice: Subject to any disclaimer, the term of this patent is extended or adjusted under 35 U.S.C. 154(b) by 514 days.

This patent is subject to a terminal disclaimer.

(21) Appl. No.: 08/796,164

(22) Filed: Feb. 6, 1997

Related U.S. Application Data

(63) Continuation-in-part of application No. PCT/US96/14659, filed on Sep. 13, 1996, and a continuation-in-part of application No. 08/667,003, filed on Jun. 20, 1996, now Pat. No. 6,197,745, and a continuation-in-part of application No. 08/616,371, filed on Mar. 15, 1996, now Pat. No. 6,855,691, said application No. PCT/US96/14659, filed on Sep. 13, 1996, is a continuation of application No. 08/667,003, filed on Jun. 20, 1996, now Pat. No. 6,197,745, and a continuation of application No. 08/616,371, filed on Mar. 15, 1996, now Pat. No. 6,855,691, said application No. 08/667,003, filed on Jun. 20, 1996, is a continuation-in-part of application No. 08/616,371, filed on Mar. 15, 1996, now Pat. No. 6,855,691.

(60) Provisional application No. 60/003,801, filed on Sep. 15, 1995.

(51) Int. Cl.[7] ........................ A61K 38/42; C07K 14/805
(52) U.S. Cl. ................ 514/6; 514/2; 514/832; 530/385; 530/829
(58) Field of Search ............................ 514/2, 6, 832; 530/385, 829

(56) References Cited

U.S. PATENT DOCUMENTS

| | | | | |
|---|---|---|---|---|
| 4,900,719 | A | 2/1990 | Means et al. ................ 514/18 |
| 5,380,758 | A | 1/1995 | Stamler et al. ............. 514/562 |
| 5,385,937 | A | 1/1995 | Stamler et al. ............. 514/557 |
| 5,395,314 | A | * 3/1995 | Klatz et al. ................... 604/24 |
| 5,405,919 | A | 4/1995 | Keefer et al. ............... 525/377 |
| 5,427,797 | A | 6/1995 | Frostell et al. ............. 424/434 |
| 5,439,882 | A | * 8/1995 | Feola et al. ..................... 514/6 |
| 5,480,866 | A | 1/1996 | Bonaventura et al. ......... 514/6 |
| 5,574,068 | A | 11/1996 | Stamler et al. ............. 514/562 |
| 5,583,101 | A | * 12/1996 | Stamler et al. ............... 514/2 |
| 5,593,876 | A | 1/1997 | Stamler et al. ............. 435/188 |
| 5,863,890 | A | 1/1999 | Stamler et al. |
| 6,087,479 | A | 7/2000 | Stamler et al. ............. 530/363 |
| 6,255,277 | B1 | 7/2001 | Stamler et al. |
| 6,291,424 | B1 | 9/2001 | Stamler et al. |
| 2002/0052314 | A1 | 5/2002 | Stamler et al. |
| 2003/0007967 | A1 | 1/2003 | Stamler et al. |
| 2003/0022267 | A1 | 1/2003 | Stamler et al. |

FOREIGN PATENT DOCUMENTS

| | | |
|---|---|---|
| WO | WO 93/09806 | 5/1993 |
| WO | WO 93/12068 | 6/1993 |
| WO | WO 94/22306 | 10/1994 |
| WO | WO 94/22482 | 10/1994 |
| WO | WO 94/22499 | 10/1994 |
| WO | WO 95/07691 | 3/1995 |
| WO | WO 96/03139 | 2/1996 |
| WO | WO 96/15797 | 5/1996 |
| WO | WO 96/16645 | 6/1996 |
| WO | WO 96/17604 | 6/1996 |
| WO | WO 96/30006 | 10/1996 |
| WO | WO 97/18000 | 5/1997 |
| WO | WO 97/37644 | 10/1997 |

OTHER PUBLICATIONS

U.S. Appl. No. 08/123,331, filed Sep. 17, 1993, now abandoned.
U.S. Appl. No. 08/438,418, filed May 10, 1995, now US 6,255,277.
U.S. Appl. No. 08/460,465, filed Jun. 2, 1995, now US 6,087,479.
U.S. Appl. No. 09/433,550, filed Nov. 4, 1999, now US 6,174,539.
U.S. Appl. No. 09/621,610, filed Jul. 21, 2000, now US 6,471,978.
U.S. Appl. No. 09/661,190, filed Sep. 13, 2000, now US 6,352,709.
U.S. Appl. No. 07/791,668, filed Nov. 14, 1991, now abandoned.
U.S. Appl. No. 08/198,854, filed Feb. 17, 1997, now abandoned.
U.S. Appl. No. 08/287,830, filed Aug. 9, 1994, now US 5,593,876.
U.S. Appl. No. 08/437,868, filed May 9, 1995, now abandoned.
U.S. Appl. No. 08/907,217, filed Aug. 6, 1997, now US 5,863,890.
U.S. Appl. No. 09/835,038, filed Apr. 16, 2001, published as 20020052314 (cited on PTO form 1449). The status and currently pending claims of this appliction are not known to Applicant.
U.S. Appl. No. 10/216,865, filed Aug. 13, 2002, published as 20030007967 (cited on PTO form 1449). The status and currently pending claims of this application are not known to Applicant.
U.S. Appl. No. 08/281,427, filed Jul. 27, 1994, which is the priority application for WO 96/03139. Status unknown to Applicant.
U.S. Appl. No. 08/043,653, filed Apr. 6, 1993, now US 5,427,797.

(Continued)

*Primary Examiner*—Bennett Celsa
(74) *Attorney, Agent, or Firm*—Hamilton, Brook, Smith & Reynolds, P.C.

(57) ABSTRACT

Diseases which can be ameliorated by delivery of NO to tissues affected by the disease can be treated by administration of nitrosyl-heme-containing donors of NO, including nitrosylhemoglobin. Nitrosylhemoglobin can be made by the reaction of NO with hemoglobin under certain conditions in which the NO:hemoglobin ratio is critical, and is converted to SNO-Hb under physiological conditions.

6 Claims, 28 Drawing Sheets

OTHER PUBLICATIONS

U.S. Appl. No. 10/066,320, filed Jan. 31, 2002, published as 20030022267 (cited on PTO form 1449). A copy of the claims currently pending is attached.

U.S. Appl. No. 10/280,085, filed Oct. 25, 2002. A copy of the claims currently pending is attached.

Search results from Derwent Word Patent Index: Stamler patent applications as of Mar. 12, 2001 (26 pages).

Wade, Ruth S. and Castro, C.E., "Redox Reactivity of Iron(III) Porphyrins and Heme Proteins with Nitric Oxide: Nitrosyl Transfer to Carbon, Oxygen, Nitrogen and Sulfur," *Chem. Res. Toxicol.*, 3(4):289–291 (1990).

Addison, Anthony W. and Stephanos, Joseph j., "Nitrosyliron (III) Hemoglobin: Autoreduction and Spectroscopy," *Biochemistry* 25(14):4104–4113 (1986).

Perutz, Max F., et al., "Influence of Globin Structures on the State of the Heme: Ferrous Low Spin Derivatives," *Biochemistry*, 15(2):378–387 (1976).

John, Maliyakal E. and Waterman, Michael R., "Structural Basis for the Conformational States of Nitrosyl Hemoglobins M Saskatoon and M Milwaukee," *The Journal of Biological Chemistry*, 255(10):4501–4506 (1980).

Trittelvitz, Eberhard and Gersonde, Klaus, "Electron–Spiin Resonance of Nitrosyl Haemoglobins: Normal α and β Chains and Mutants Hb M Iwate and Hb Zürich," *Eur. J. Biochem.*, 51:33–42 (1975).

Lancaster, Jack R., Jr., "Simulation of the Diffusion and Reaction of Endogenously Produced Nitric Oxide," *Proc. Natl. Acad. Sci. USA*, 91:8137–8141 (1994).

Butler, Anthony R. et al., "NO, Nitrosonium Ions, Nitroxide Ions, Nitrosothiols and Iron–Nitrosyls in Biology: A Chemist's Perspective," *TiPS*, 16:18–22 (1995).

Sharma, Vijay S. and Ranney, Helen M., "The Dissociation of NO from Nitrosylhemoglobin," *The Journal of Biological Chemistry*, 253(18):6467–6472 (1978).

Moore, Edwin G. and Gibson, Quentin H., "Cooperativity in the Dissociation of Nitric Oxide from Hemoglobin," *The Journal of Biological Chemistry*, 251(9):2788–2794 (1976).

Khartitonov, V.G., et al., "Interactions of Nitric Oxide with Heme Proteins Using UV–VIS Spectroscopy," *Methods in Nitric Oxide Research*, pp. 39–45, Edited by Martin Feelisch and Jonathan S. Stamler, John Wiley & Sons Ltd. (1996).

Taketa, Fumito, et al., "Chain Nonequivalence in Binding of Nitric Oxide to Hemoglobin," *The Journal of Biological Chemistry*, 253(15):5448–5451 (1978).

Henry, Y. and Cassoly, R., "Chain Non–Equivalence in Nitric Oxide Binding to Hemoglobin," *Biochemical and Biophysical Research Communications*, 51(3):659–665 (1973).

Wennmalm, ÅA., et al., "Dependence of the Metabolism of Nitric Oxide (NO) in Healthy Human Whole Blood on the Oxygenation of Its Red Cell Haemoglobin," *Br. Journal Pharmacol.*, 106:507–508 (1992).

Hille, Russ, et al., "Spectral Transitions of Nitrosyl Hemes During Ligand Binding to Hemoglobin," *The Journal of Biological Chemistry*, 254(23):12110–12120 (1979).

Cassoly, R. and Gibson, Q.H., "Conformation, Co–Operativity and Ligand Binding in Human Hemoglobin," *J. Mol. Biol.*, 91:301–313 (1975).

Cantilena, Louis R., Jr., et al., "Nitric Oxide Hemoglobin in Patients Receiving Nitroglycerin as Detected by Electron Paramagnetic Resonance Spectroscopy," *J. Lab. Clin. Med.*, 120(6):902–907 (1992).

Salhany, J.M, et al., "Correlations Between Quaternary Structure and Ligand Dissociation Kinetics for Fully Liganded Hemoglobin," *Biochemistry*, 14(10):2180–2190 (1975).

Kruszyna, Harriet, et al., "Red Blood Cells Generate Nitric Oxide From Directly Acting, Nitrogenous Vasodilators," *Toxicology and Applied Pharmacology*, 91:429–438 (1987).

Stamler, Jonathan S. et al., "S–Nitrosylaton of Proteins with Nitric Oxide: Synthesis and Characterization of Biologically Active Compounds," *Proc. Natl. Acad. Sci. USA*, 89:444–448 (1992).

Langford, E.J. et al., "Inhibition of Platelet Activity by S–Nitrosoglutathione During Coronary Angioplasty," *The Lancet*, 344:1458–1460 (1994).

Simon, Daniel I. et al., "Polynitrosylated Proteins: Characterization, Bioactivity, and Functional Consequences," *Proc. Natl. Acad. Sci. USA*, 93:4736–4741 (1996).

Doyle, Michael P. et al., "Structural Effects in Alkyl Nitrite Oxidation of Human Hemoglobin," *Journal of Biological Chemistry.* 259(1):80–87 (1984).

Shah, N.S. et al., "Efficacy of Inhaled Nitric Oxide in a Porcine MOdel of Adult Respiratory Distress Syndrome," *Archives of Surgery*, 129(2):158–164 (1994).

Kukovetz, W.R. et al., "Cellular Mechanism of Action of Therapeutic Nitric Oxide Donors," *European Heart Journal*, 12 (Suppl. E) :16–24 (1991).

Greenburg, A.G. and Kim, H.W., "Nitrosyl Hemoglobin Formation In Vivo After Intravenous Administration of a Hemoglobin–Based Oxygen Carrier in Endotoxemic Rats," *Artif. Cells, Blood Substitutes, Immobilization Biotechnol.*, 23(3):271–276 (1995).

Clancy, Robert M. et al., "Use of Thionitrobenzoic Acid to Characterize the Stability of Nitric Oxide in Aqueous Solutions and in Porcine Aortic Endothelial Cell Suspensions," *Anal. Biochem.*, 191(1):138–143 (1990).

Charache, S. et al., "Evaluation of Extracorporeal Alkylation of Red Cells as a Potential Treatment for Sickle Cell Anemia," *Blood*, 47(3):481–488 (1976).

Wheeler, G.P. et al., "Anti–Sickling Acitivty of Nitrosoureas," *Biochem. Biphys. Res. Comm.* 54(3):1024–1029 (1973).

Clancy, Robert M. al., "Nitric Oxide Reacts with Intracellular Glutathione and Activates the Hexose Monophosphate Shunt in Human Neutrophils: Evidence for S–Nitrosoglutathione as a Bioactive Intermediary," *Proc. Natl. Acad. Sci. USA*, 91:3680–3684 (1994).

Stamler, Jonathan S., "Redox Signaling: Nitrosylation and Related Target Interactions of Nitric Oxide," *Cell*, 78:931–936 (1994).

Arnelle, Derrick R. and Stamler, Jonathan S., "NO$^+$, NO , and NO$^-$Donation by S–Nitrosothiols: Implications for Regulation of Physiological Functions by S–Nitrosylation and Acceleration of Disulfide Formation" *Archives of Biochemistry and Biophysics*, 318(2):279–285 (1995).

Kondo, T. et al., "Thiol Transport from Human Red Blood Cells," *Methods in Enzymology*, 252:72–82 (1995).

Jia, Li et al., "S–Nitrosohaemoglobin: A Dynamic Activity of Blood Involved in Vascular Control," *Nature*, 380:221–226 (1996).

Ignarro, Louis J. et al., "Mechanism of Vascular Smooth Muscle Relaxation by Organic Nitrates, Nitrites, Nitroprusside and Nitric Oxide: Evidence for the Invovlement of S–Nitrosothiols as Active Intermediates," *The Journal of Pharmacology and Experimental Therapeutics, 218*(3):739–749 (1981).

Ribeiro, JoséM.C. et al., "Reversible Binding of Nitric Oxide by a Salivary Heme Protein from a Bloodsucking Insect," *Science, 260*:539–541 (1993).

Simon, Daniel I. et al., "Effect of Nitric Oxide Synthase Inhibition on Bleeding Time in Humans," *Journal of Cardiovascular Pharmacology, 26*:339–342 (1995).

Radomski, Marek W. et al., "S–Nitroso–Glutathione Inhibits Platelet Activation In Vitro and In Vivo," *Br. J. Pharmacol., 107*:745–749 (1992).

Scharfstein, Jonathan S. et al., "In Vivo Transfer of Nitric Oxide Between a Plasma Protein–Bound Reservoir and Low Molecular Weight Thiols," *J. Clin. Invest., 94*:1432–1439 (1994).

Kosaka, H. et al., "ESR Spectral Transition by Arteriovenous Cycle in Nitric Oxide Hemoglobin of Cytokine–Treated Rats," *Am. J. Physiol., 266*(5):1400–1405 (1994).

Kruszyna, R. et al., "Generation of Valency Hybrids and Nitrosylated Species of Hemoglobin in Mice by Nitric Oxide Vasodilators," *Toxicol. Appl. Pharmacol., 94*(3):458–465 (1988).

Freedman, Jane E. et al., "Glutathione Peroxidase Potentiates the Inhibition of Platelet Function by S–Nitrosothiols," *J. Clin. Invest., 96*:394–400 (1995).

Feelisch, M. and Stamler, J.S., "Donors of Nitrogen Oxides," *Methods In Nitric Oxide Research*, John Wiley & Sons Ltd. (1996).

Stamler, J.S. and Feelisch, M., "Preparation and Detection of S–Nitrosothiols," *Methods In Nitric Oxide Research*, John Wiley & Sons Ltd. (1996).

* cited by examiner

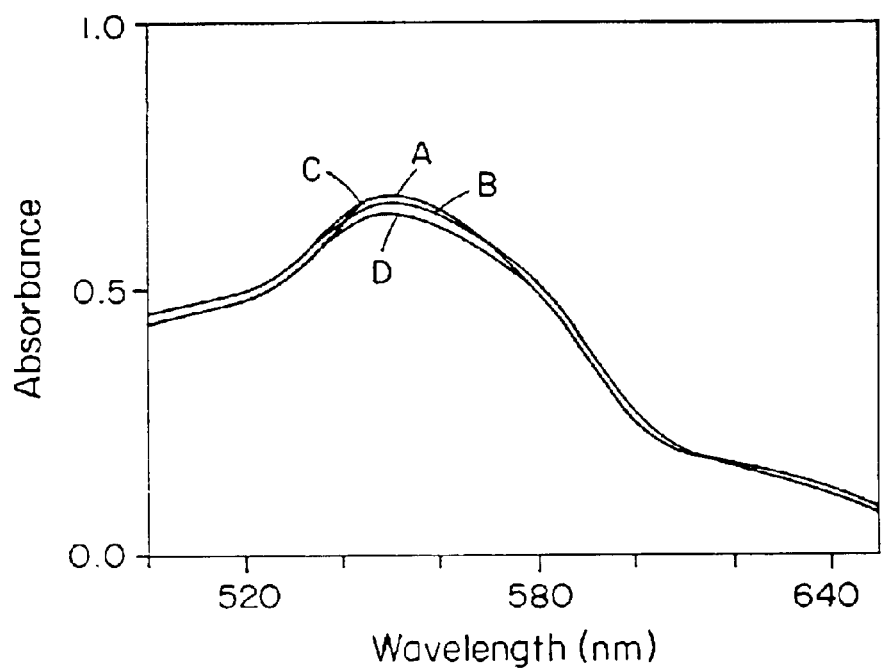
FIG. IC
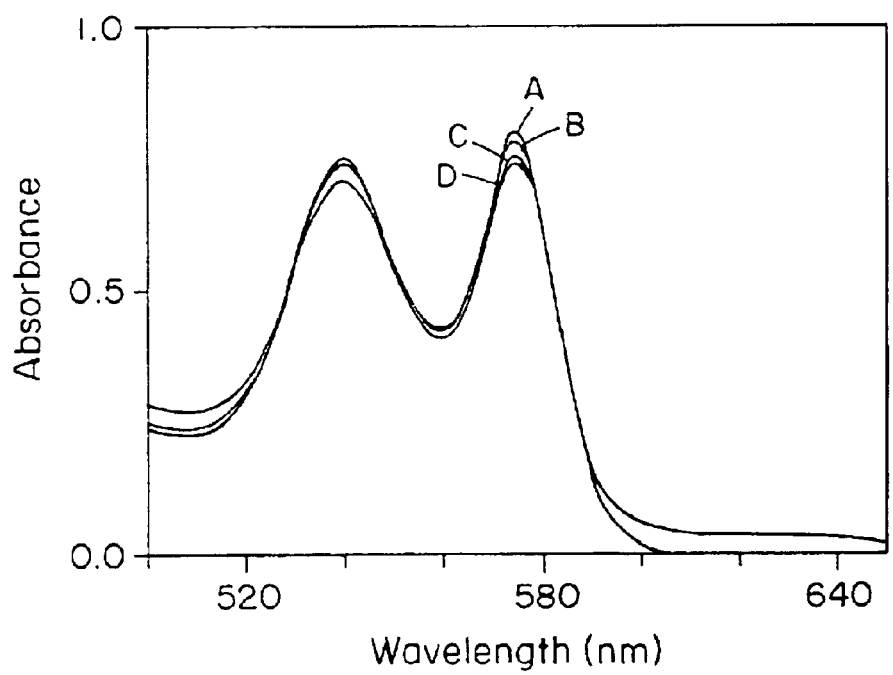
FIG. ID

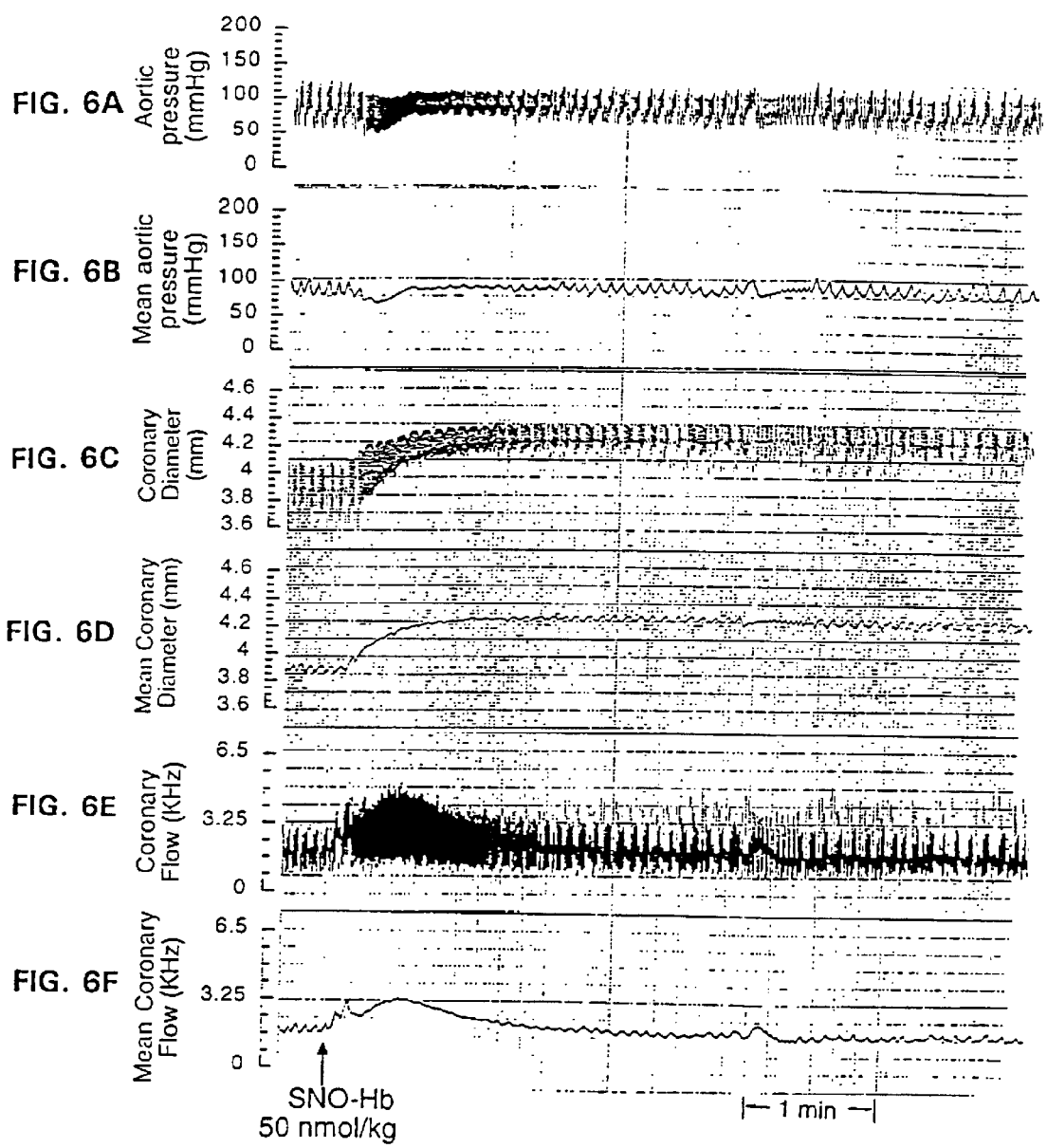

MODIFIED HEMOGLOBINS, INCLUDING NITROSYLHEMOGLOBINS, AND USES THEREOF

RELATED APPLICATIONS

This application is a continuation-in-part of PCT/US96/14659 filed on Sep. 13, 1996, and a continuation-in-part of U.S. patent application Ser. No. 08/667,003 filed on Jun. 20, 1996, now U.S. Pat. No. 6,197,746 and a continuation-in-part of U.S. patent application Ser. No. 08/616,371 filed on Mar. 15, 1996, now U.S. Pat. No. 6,355,691. PCT/US96/14659 is a continuation of Ser. No. 08/667,003 filed on Jun. 20, 1996, now U.S. Pat. No. 6,197,745 and a continuation-in-part of Ser. No. 08/616,371 filed on March 15, 1996, now U.S. Pat. No. 6,855,691 and claims the benefit of U.S. Provisional Application No. Ser. No. 60/003,801 filed on Sep. 15, 1995. U.S. patent application Ser. No. 08/667,003 is a continuation-in-part of U.S. patent application Ser. No. 08/616,371, and a claims the benefit of Provisional Application No. 60/003,801. The teachings of all of the above applications are each incorporated herein by reference in their entirety.

GOVERNMENT SUPPORT

This invention was made with government support under Grant No. HL52529 awarded by the National Institutes of Health. The government has certain rights in the invention.

BACKGROUND OF THE INVENTION

Interactions of hemoglobin (Hb) with small diffusible ligands, such as $O_2$, CO2 and NO, are known to occur at its metal centers and amino termini. The $O_2/CO_2$ delivery functionalities, which arise in the lung and systemic microvasculature, are allosterically controlled. Such responsiveness to the environment is not known to apply in the case of NO. Specifically, it has been thought previously that Hb(Fe) is involved in limiting NO's sphere of action (Lancaster, J. R., Proc. Natl. Acad. Sci. USA 91:8137–8141 (1994); Wood, J. and Garthwaite, J., J. Neuropharmacol. 33:1235–1244 (1994)), but that NO does not modify the functional properties of Hb to any physiologically significant degree. Kinetic modeling based on this assumption, however, predicts that the vast majority of free NO in the vasculature should be scavenged by Hb (Lancaster 1994). Accordingly, the steady-state level of NO may fall below the $K_m$ for target enzymes such as guanylate cyclase (Lancaster 1994), if not in the unperturbed organism, then with oxidant stress such as that found in atherosclerosis. These considerations raise the fundamental question of how NO exerts its biological activity.

One answer to this paradox may be found in the propensity of nitric oxide to form S-nitrosothiols (RSNOs) (Gaston, B. et al., Proc. Natl. Acad. Sci. USA, 90:10957–10961 (1993)), which retain NO-like vasorelaxant activity (Stamler, J. S., et al., Proc. Natl. Acad. Sci, USA, 89:444–448 (1992)), but which are not subject to the diffusional constraints imposed by the high concentration of Hb in the blood. In particular, the NO group of RSNOs possesses nitrosonium ($NO^+$) character that distinguishes it from NO itself. It is increasingly appreciated that RSNOs have the capacity to elicit certain functions that NO is incapable of (DeGroote, M. A. et al., Proc. Natl: Acad. Sci. USA, 92:6399–6403 (1995); Stamler, J. S., Cell, 78:931–936 (1994)). Moreover, consideration has been given to the possibility that —SNO groups in proteins may serve a signaling function, perhaps analogous to phosphorylation (Stamler, J. S. et al., Proc. Natl. Acad. Sci. USA, 89:444–448 (1992); Stamler, J. S. Cell, 78:931–926 (1994)). Although S-nitrosylation of proteins can regulate protein function (Stamler, J. S. et al., Proc. Natl. Acad. Sci. USA, 89:444–448 (1992); Stamler, J. S., Cell, 78:931–936 (1994)), intracellular S-nitrosoproteins—the sine qua non of a regulatory posttranslational modification—has heretofore not been demonstrated.

Hemoglobin is a tetramer composed of two alpha and two beta subunits. In human Hb, each subunit contains one heme, while the beta (β) subunits also contain highly reactive SH groups (cys93) (Olson, J. S., Methods in Enzymology 76:631–651 (1981); Antonini, E. & Brunori, M. In Hemoglobin and Myoglobin in Their Reactions with Ligands, American Elsevier Publishing Co., Inc., New York, pp. 29–31 (1971)). These cysteine residues are highly conserved among species although their function has remained elusive.

NO (nitric oxide) is a biological "messenger molecule" which decreases blood pressure and inhibits platelet function, among other functions. NO freely diffuses from endothelium to vascular smooth muscle and platelet and across neuronal synapses to evoke biological responses. Under some conditions, reactions of NO with other components present in cells and in serum can generate toxic intermediates and products at local concentrations in tissues which are effective at inhibiting the growth of infectious organisms. Thus, it can be seen that a method of administering an effective concentration of NO or biologically active forms thereof would be beneficial in certain medical disorders.

Platelet activation is an essential component of blood coagulation and thrombotic diathesis. Activation of platelets is also seen in hematologic disorders such as sickle cell disease, in which local thrombosis is thought to be central to the painful crisis. Inhibition of platelet aggregation is therefore an important therapeutic goal in heart attacks, stroke, peripheral vascular disease and shock (disseminated intravascular coagulation). Researchers have attempted to give artificial hemoglobins to enhance oxygen delivery in all of the above disease states. However, as recently pointed out by Olsen and coworkers, administration of underivatized hemoglobin leads to platelet activation at sites of vascular injury (Olsen S. B. et al., Circulation 93:327–332 (1996)). This major problem has led experts to conclude that cell-free underivatized hemoglobins may pose a significant risk in the patient with vascular disease or a clotting disorder (Marcus, A. J. and J. B. Broekman, Circulation 93:208–209 (1996)). New methods of providing for an oxygen carrier and/or a method of inhibiting platelet activation would be of benefit to patients with vascular disease or who are otherwise at risk for thrombosis.

SUMMARY OF THE INVENTION

The invention relates to methods of forming SNO-Hb by reaction of Hb with S-nitrosothiol in procedures which avoid oxidation of the heme. The invention also includes methods of producing nitrosated (including nitrosylated at thiols or metals) and nitrated derivatives of hemoglobins in which the heme Fe may or may not be oxidized, depending on the steps of the method. The invention also relates to a method of therapy for a condition in which it is desired to oxygenate, to scavenge free radicals, or to release $NO^+$ groups to tissues. SNO-Hb in its various forms and combinations thereof (oxy, deoxy, met; specifically S-nitrosylated, or nitrosated or nitrated to various extents) can be administered to an animal or human in these methods. Thiols and/or NO donating agents can also be administered to enhance the transfer of $NO^+$ groups. Examples of conditions to be treated by nitrosated or nitrated forms of hemoglobin include ischemic injury, hypertension, angina, reperfusion injury and inflammation, and diseases characterized by thrombosis.

BRIEF DESCRIPTIONS OF THE DRAWINGS

FIGS. 1A–1D are spectrographs of different forms of Hb as described in Example 1.

FIGS. 6A–6F are a series of tracings recording blood pressure (FIGS. 6A and 6B), coronary artery diameter (FIGS. 6C and 6D) and coronary artery flow (FIGS. 6E and 6F), after administration of S-nitrosohemoglobin to anesthetized dogs.

Figure 7A:
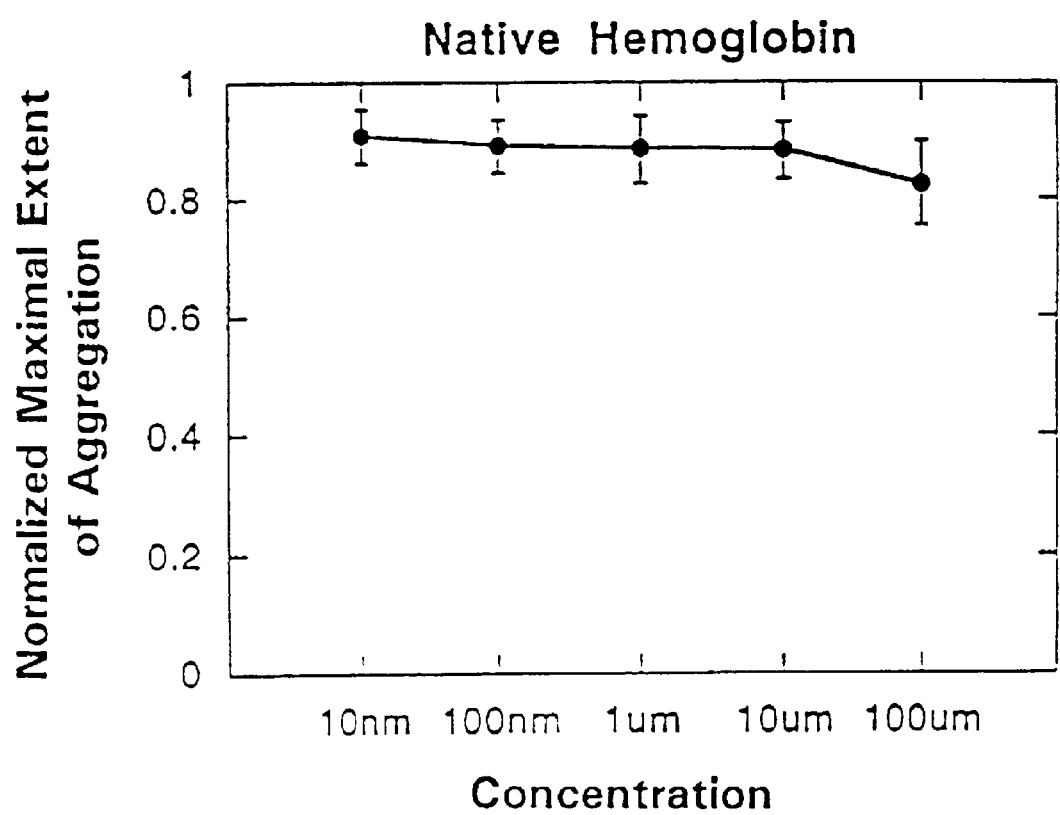

FIG. 7A is a graph illustrating the effect of unmodified $HbA_0$ on platelet aggregation. The maximal extent of aggregation of platelets is plotted against the concentration of HbA (10 nM to 100 μm) preincubated with platelets. Experiments were performed as in Example 9. Vertical bars plotted with each data point indicate the standard deviation.

Figure 7B:
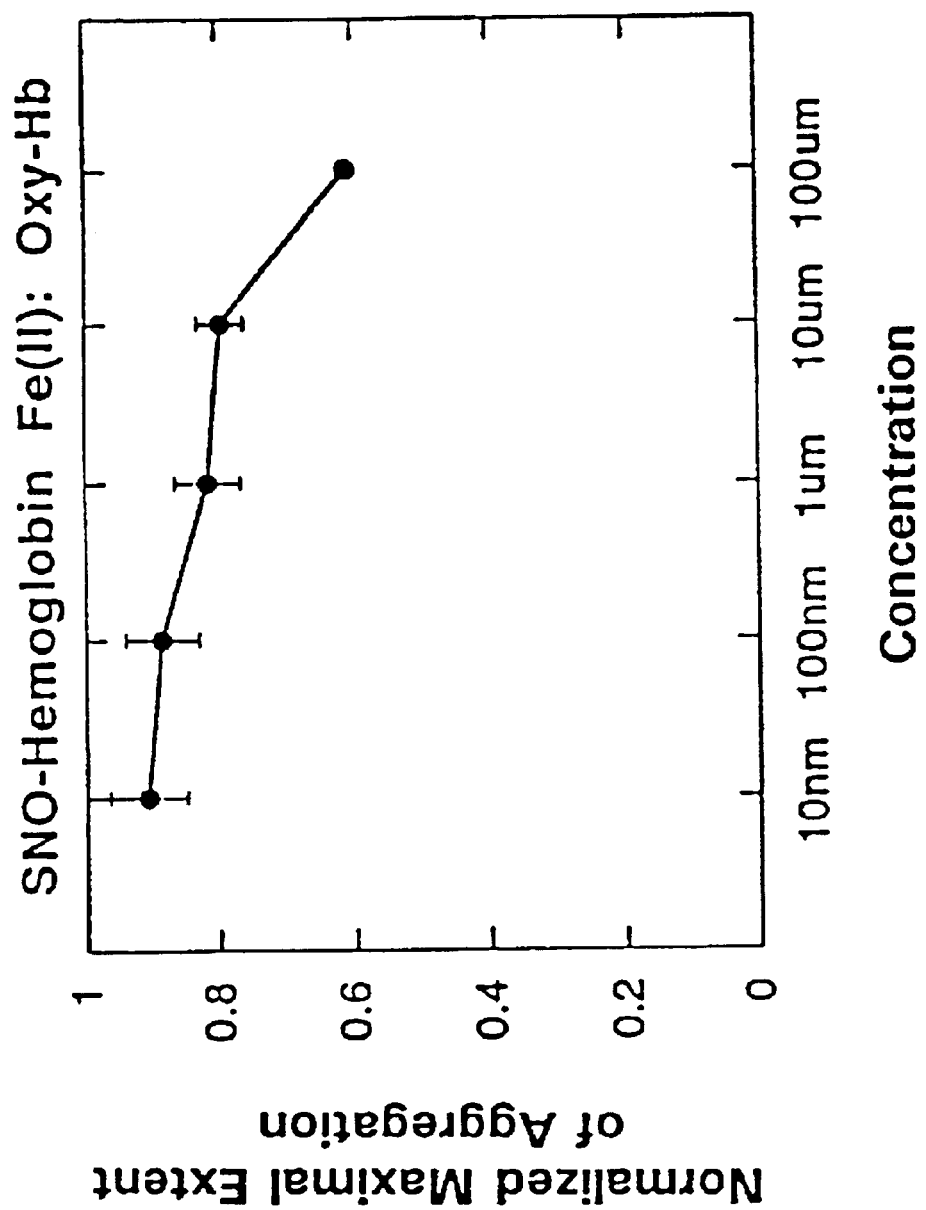

FIG. 7B is a graph illustrating the effect of S-nitroso(oxy) hemoglobin on platelet aggregation. The normalized maximal extent of aggregation of platelets is plotted against the concentration of HbA (10 nM to 100 μm) preincubated with platelets.

Figure 7C:
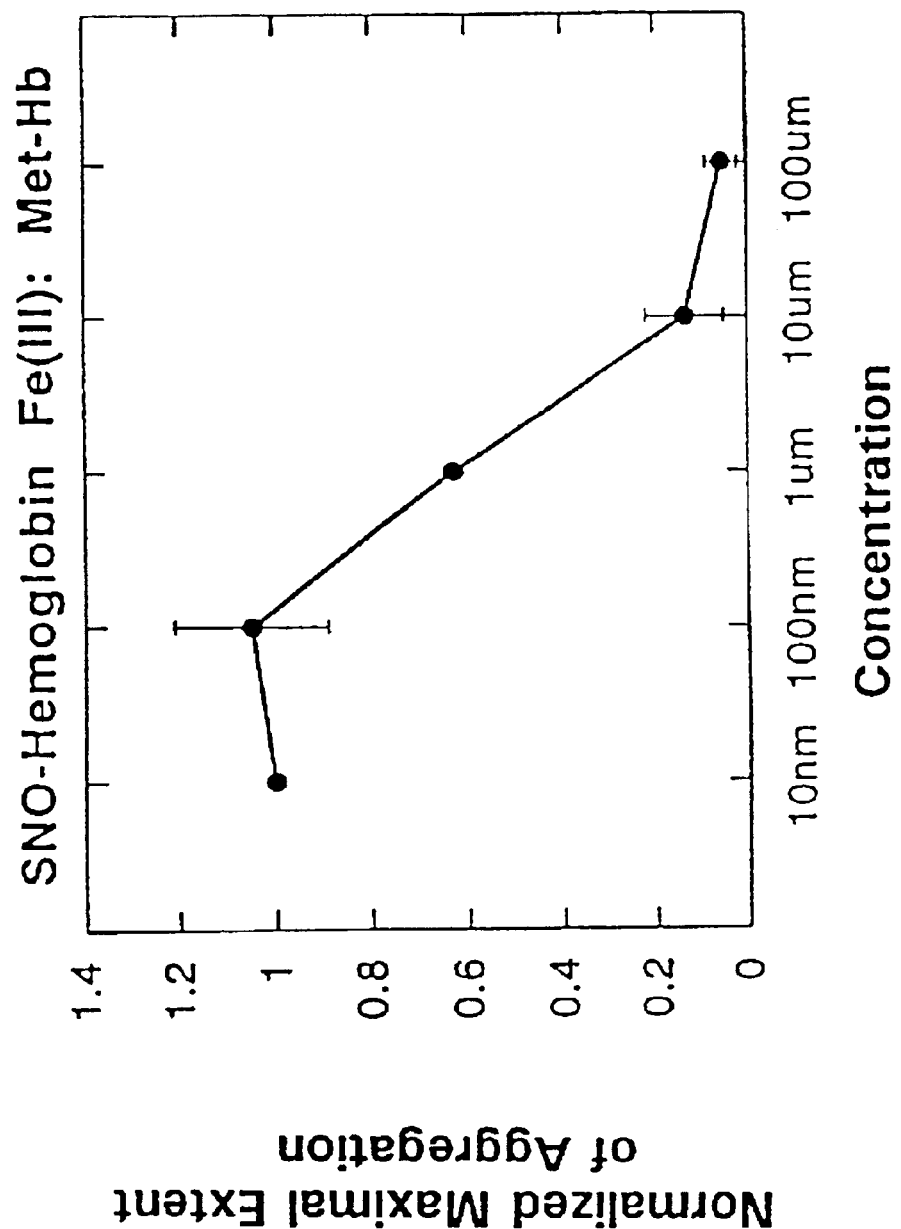

FIG. 7C is a graph illustrating the antiaggregation effects on platelets by S-nitroso(met)hemoglobin.

Figure 8:
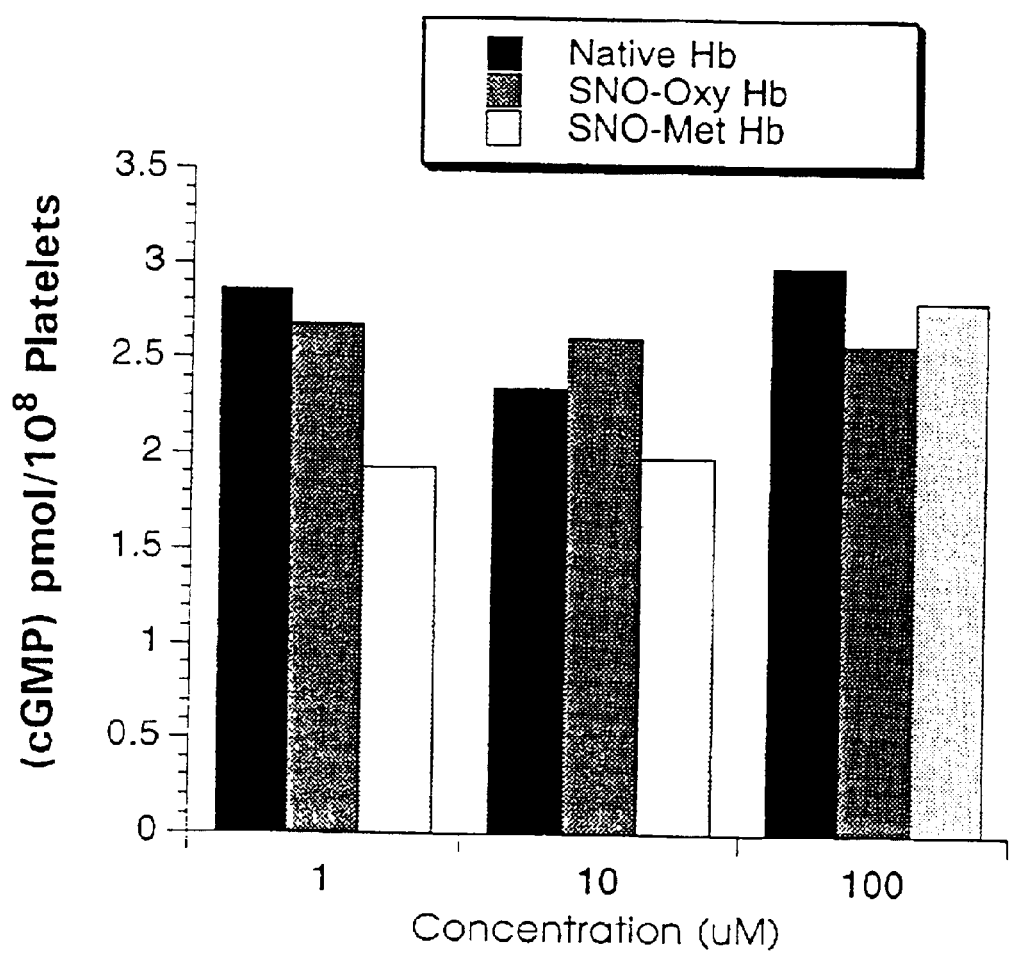

FIG. 8 is a bar graph showing the amount of cGMP (guanosine 3',5'-cyclic phosphoric acid), assayed as in Example 10, for 1, 10 and 100 μM concentrations of native Hb, SNO-oxyHb or SNO-metHb interacting with $10^8$ platelets.

Figure 9A:
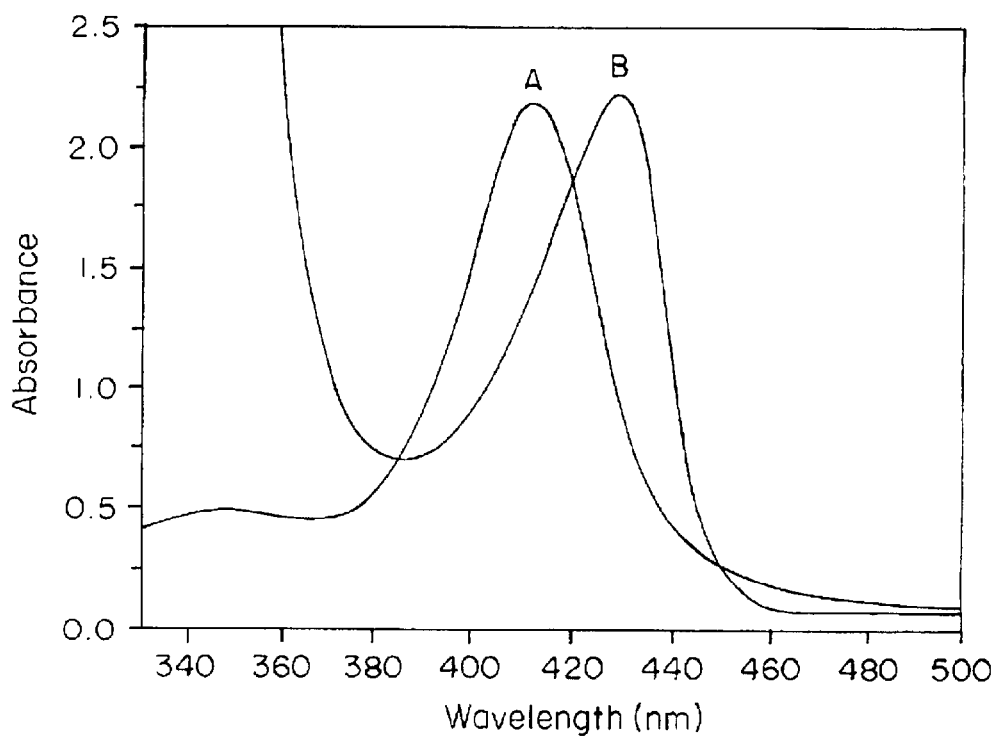

FIG. 9A is a graph which shows the spectra (absorbance versus wavelength in nanometers) of $HbA_0$ treated as described in Example 11. The shift in the wavelength of maximum absorbance of spectrum B relative to spectrum A illustrates the extent of addition of No groups to $HbA_0$.

Figure 9B:
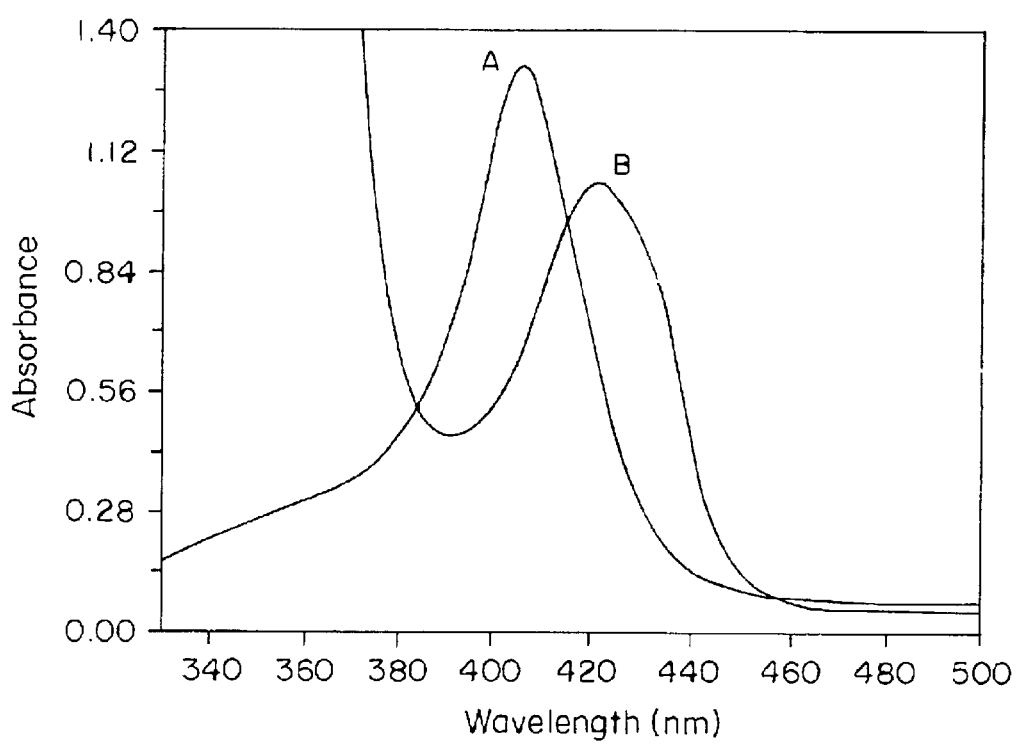

FIG. 9B is a graph which shows the spectra of Hb treated with 100-fold excess S-nitrosoglutathione as described in Example 11.

Figure 9C:
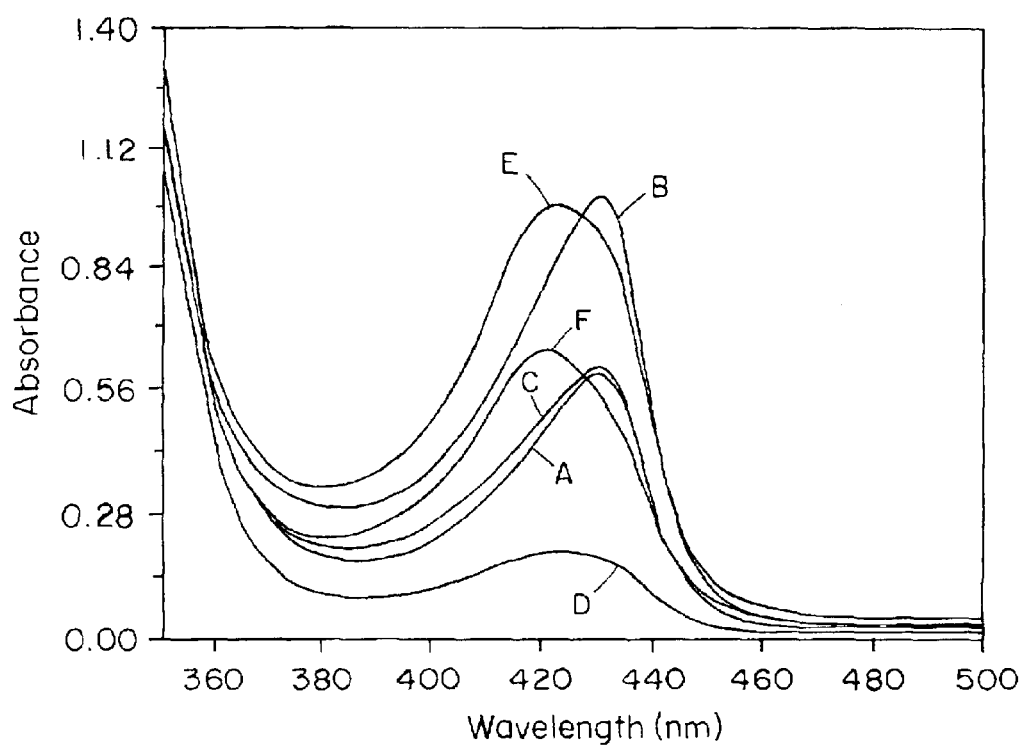

FIG. 9C is a graph which shows the spectra of $HbA_0$ treated with excess S-nitrosocysteine as described in Example 11.

Figure 9D:
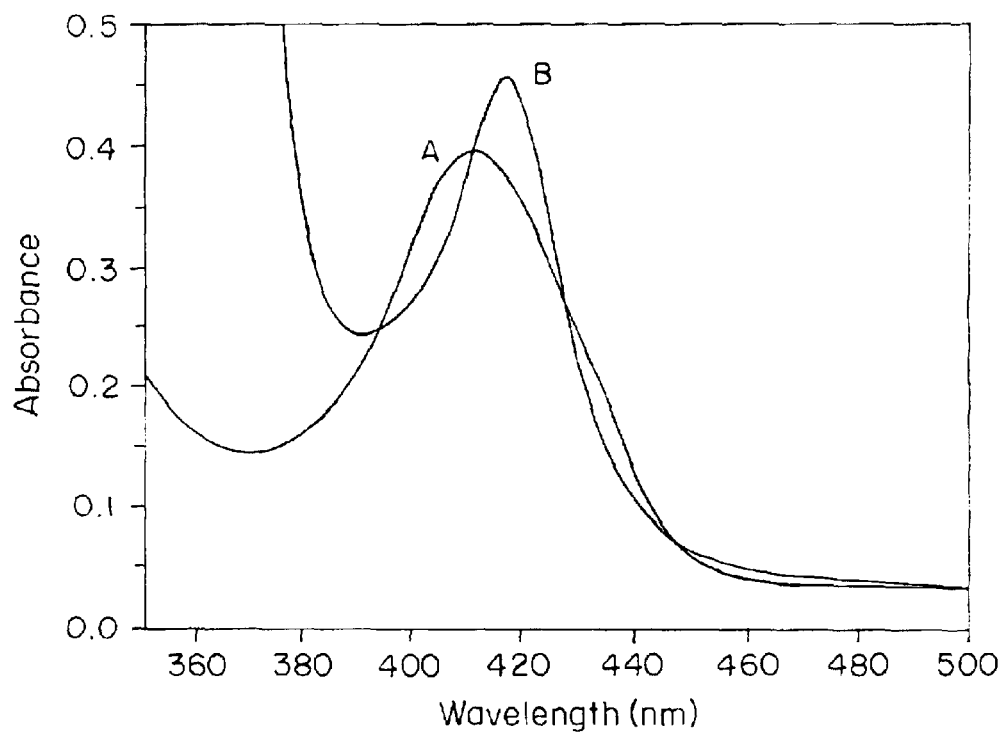

FIG. 9D is a graph which shows the spectra of rat Hb treated with 100-fold excess S-nitrosocysteine. Spectrum A shows nitrosated Hb not further treated with dithionite; spectrum B shows nitrosated Hb further treated with dithionite.

Figure 9E:
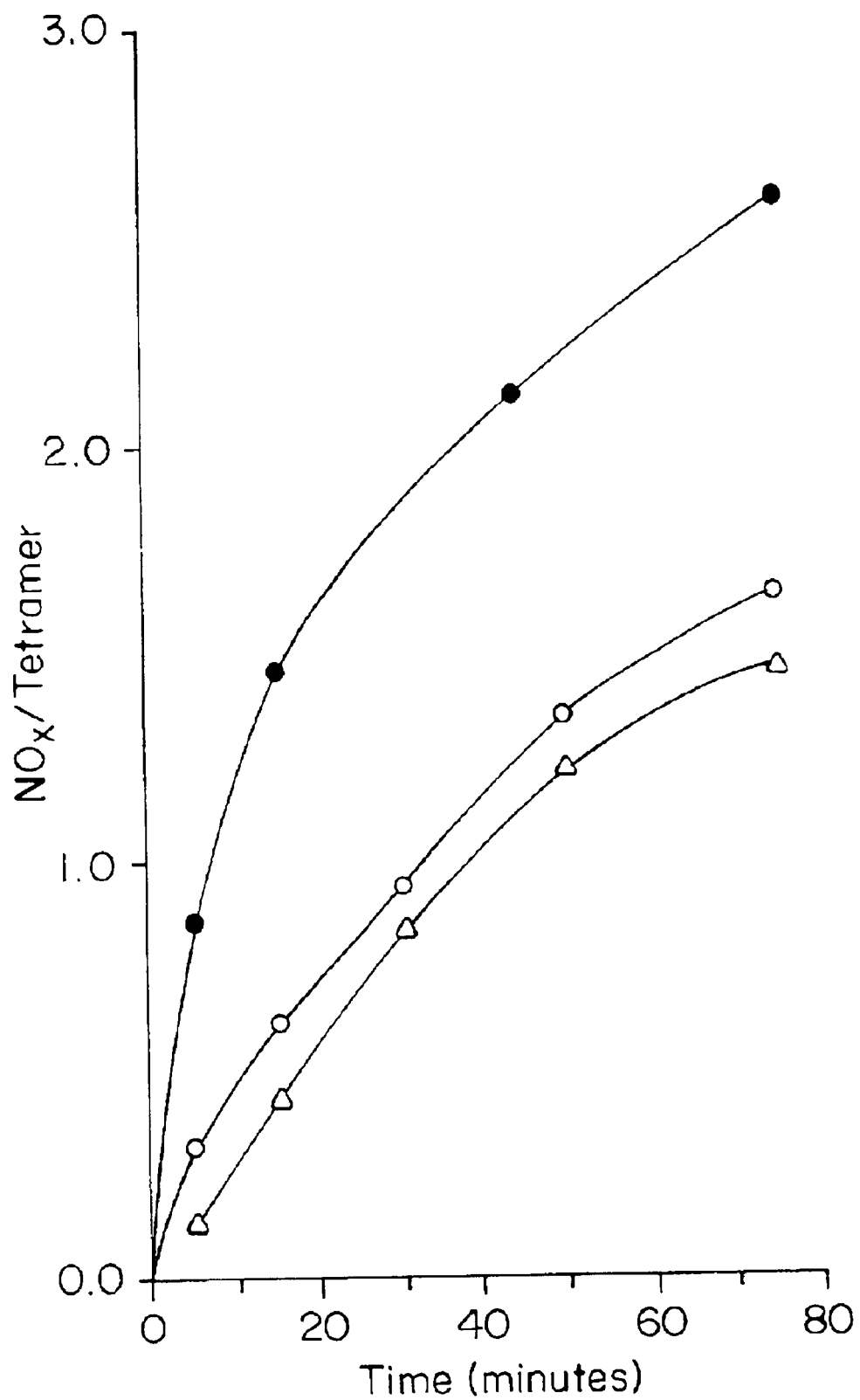

FIG. 9E is a graph illustrating the increase in nitrosated Hb product with time by reacting $HbA_0$ with either 100× excess S-nitrosocysteine (top curve) or 10×excess S-nitrosocysteine (middle curve). $HbA_0$ was preincubated with 100 μM inositol hexaphosphate before reacting with 10×excess S-nitrosocysteine (bottom curve; triangle points). (See Example 11.)

Figure 10:
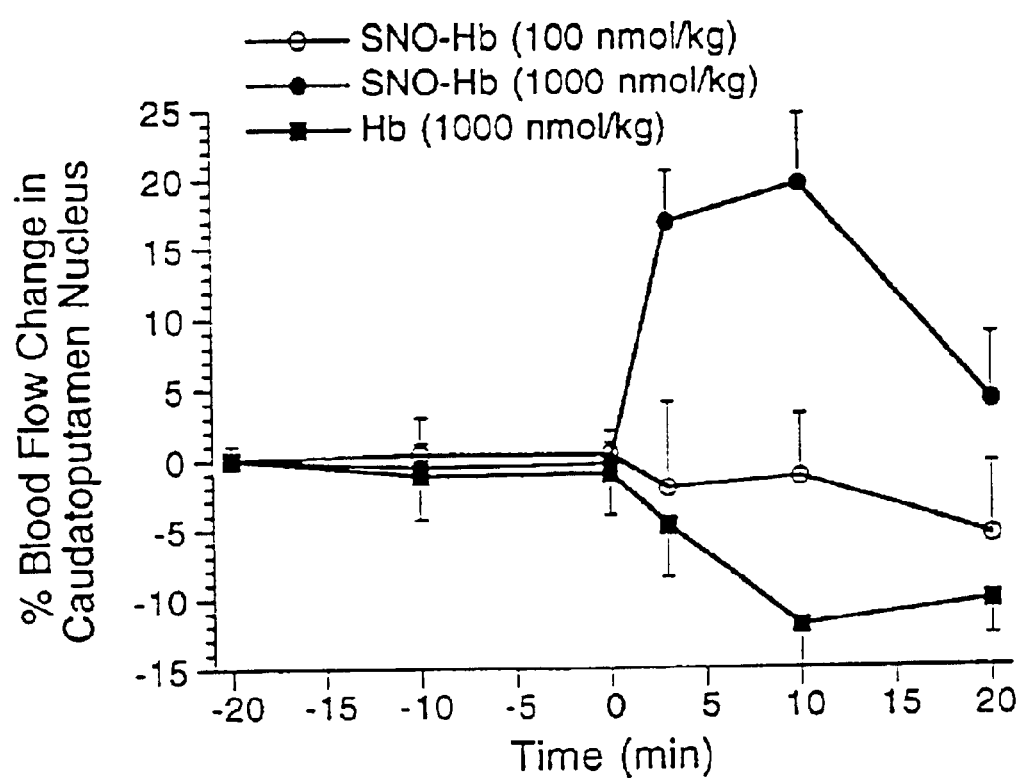

FIG. 10 is a graph illustrating the percent change, with time, in blood flow measured in caudatoputamen nucleus of rats after injection of the rats with: ○, 100nmol/kg SNO-Hb; ●, 1000 nmol/kg SNO-Hb; or ■, 1000 nmol/kg underivatized Hb (see Example 12).

Figure 11:
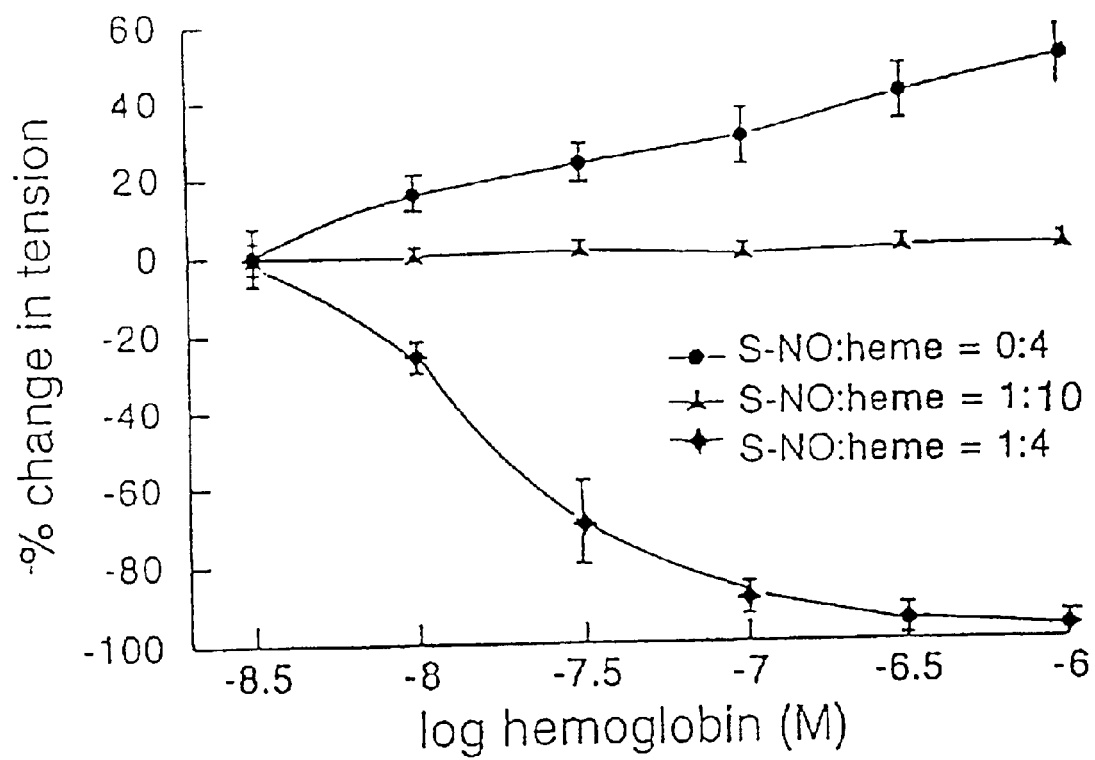

FIG. 11 is a graph illustrating the percent change in tension of a ring of aorta from rabbit, plotted as a function of the log of the molar concentration of hemoglobin tested (see Example 13). ●, Hb treated with S-nitrosocysteine at a ratio of 1:1 CYSNO/Hb; ○, Hb treated with CYSNO at a ratio of 10:1 CYSNO/Hb; ♦, Hb treated with CYSNO at a ratio of 100:1.

Figure 12:
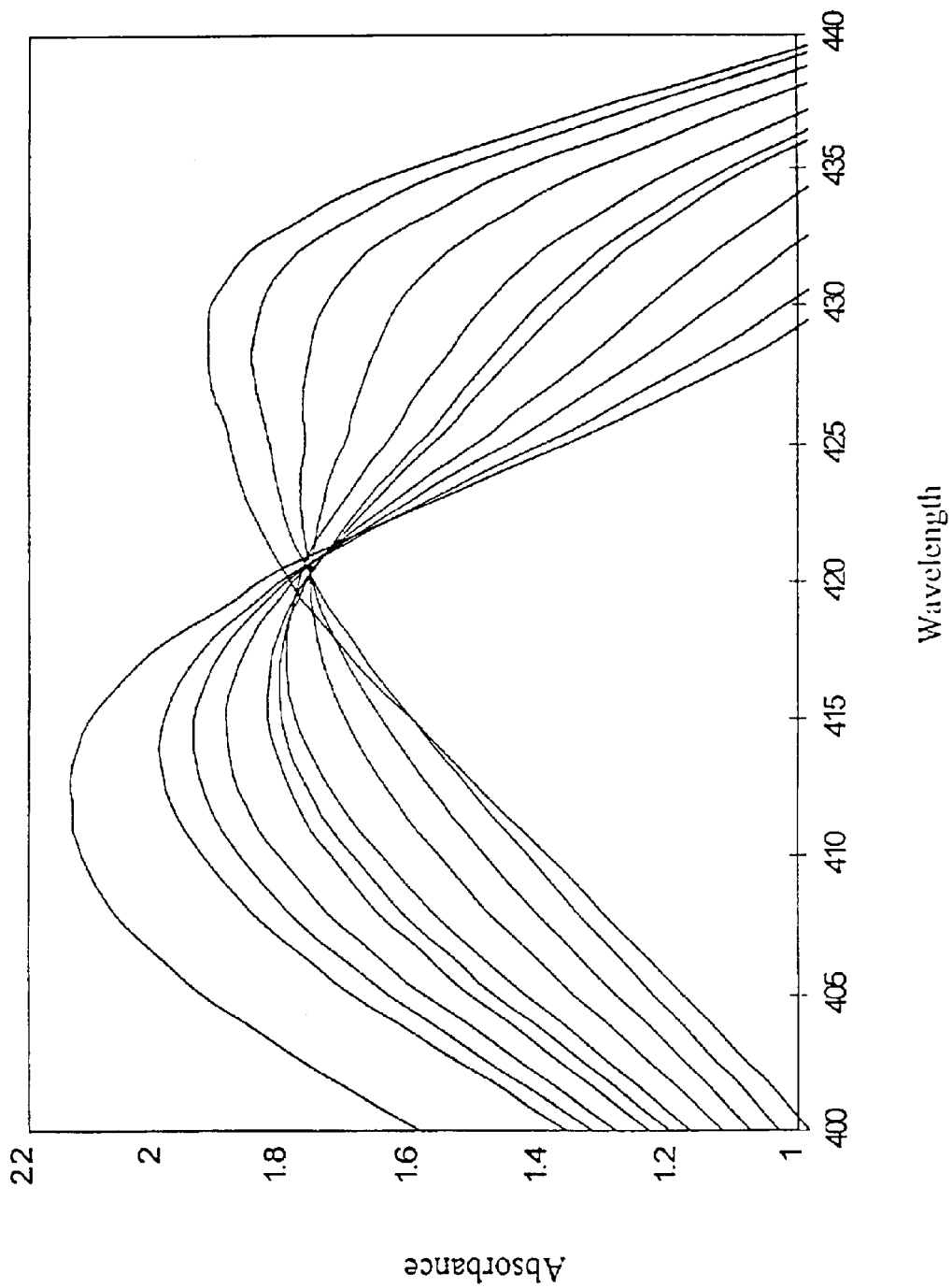

FIG. 12 is a graph of the absorbance versus the wavelength of light (nm), for aqueous solutions of 17 μM deoxyhemoglobin, 1 μM NO, and varying amounts of dissolved oxygen added by sequential injections of room air. The absorbance of the initial solution (no added air) is shown by the curve with the highest peak at approximately 430 nm. Sequential additions of 50 μl of air shift the curve leftwards on the graph. See Example 14.

Figure 13:
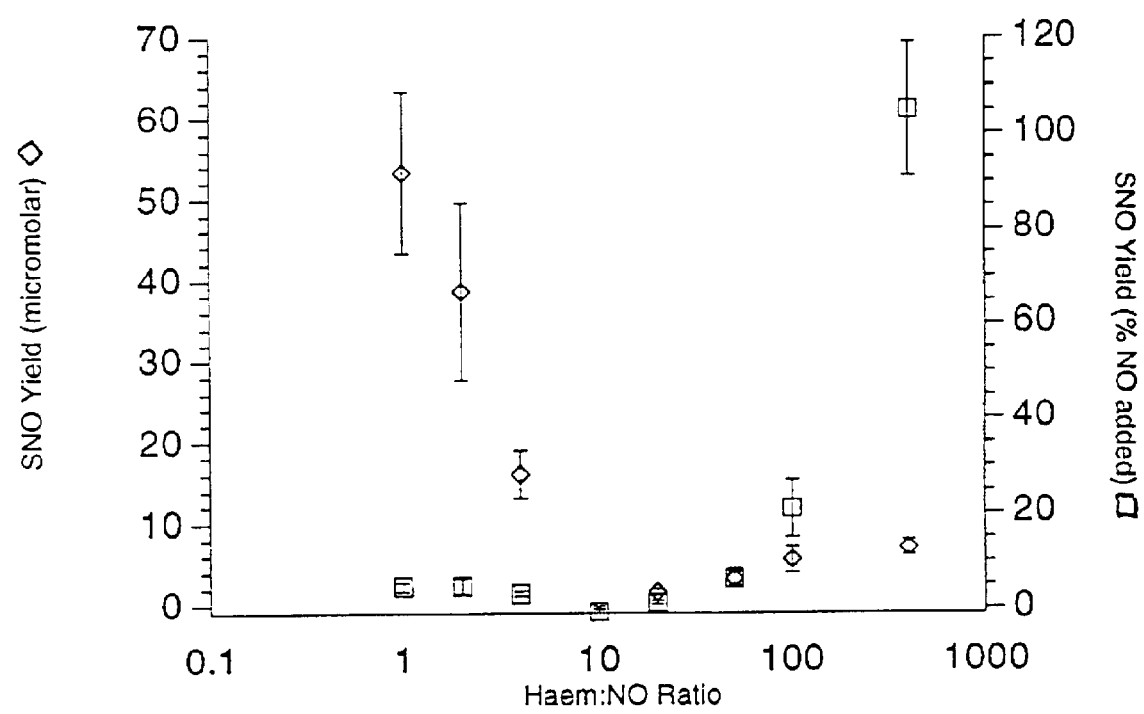

FIG. 13 is a graph showing the yield of SNO-Hb as micromolar concentration (left axis, diamonds) and as % of NO added (right axis, squares), plotted against the heme:NO ratio, when nitrosyl-deoxyHb made at various ratios of heme:NO was exposed to oxygen. See Example 15.

Figure 14A:
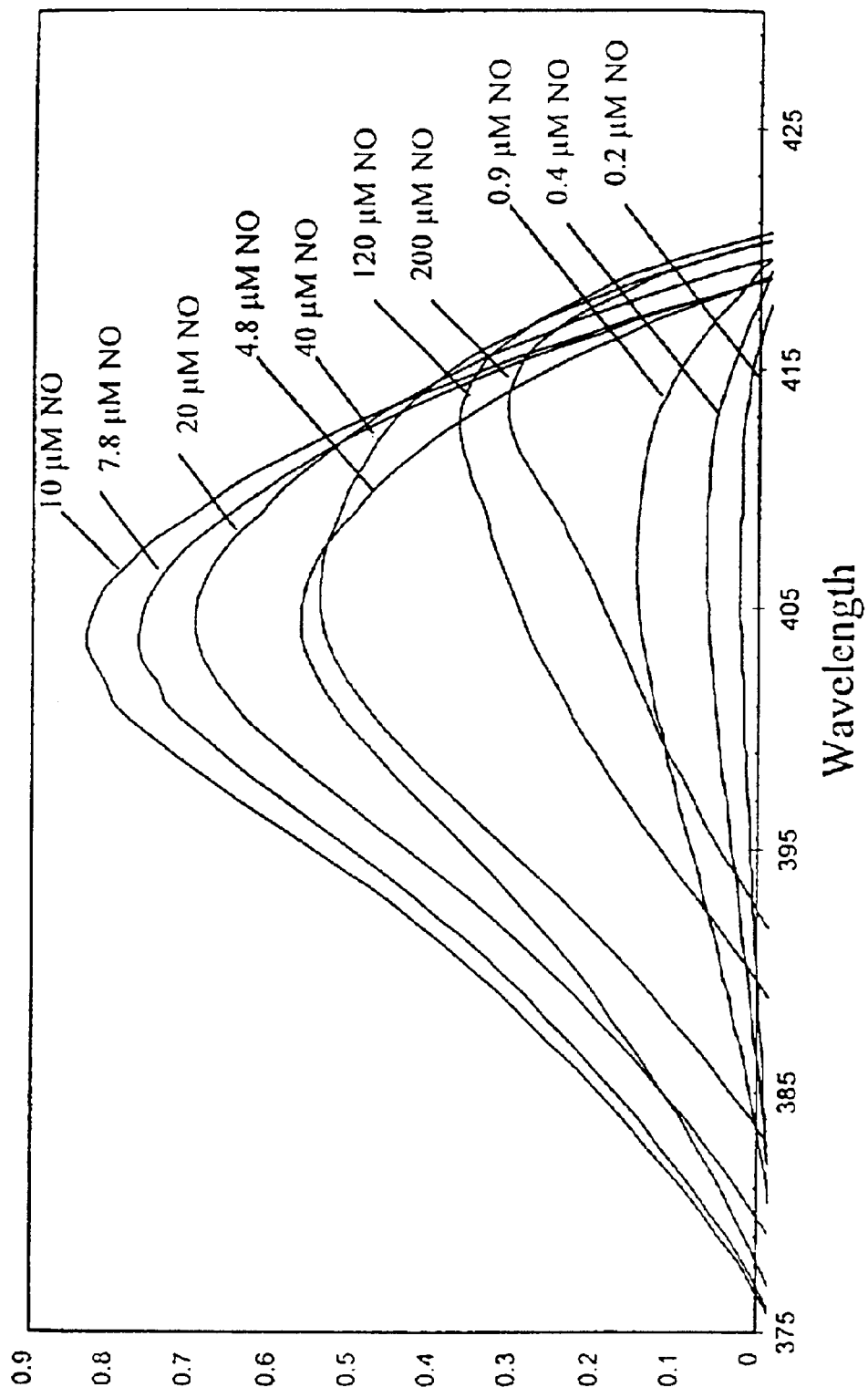

FIG. 14A is a graph showing difference spectra (each a spectrum of the NO and Hb mixture minus spectrum of the starting deoxyHb), for 17 μM hemoglobin and NO mixtures, for the concentrations of NO shown. See Example 16.

Figure 14B:
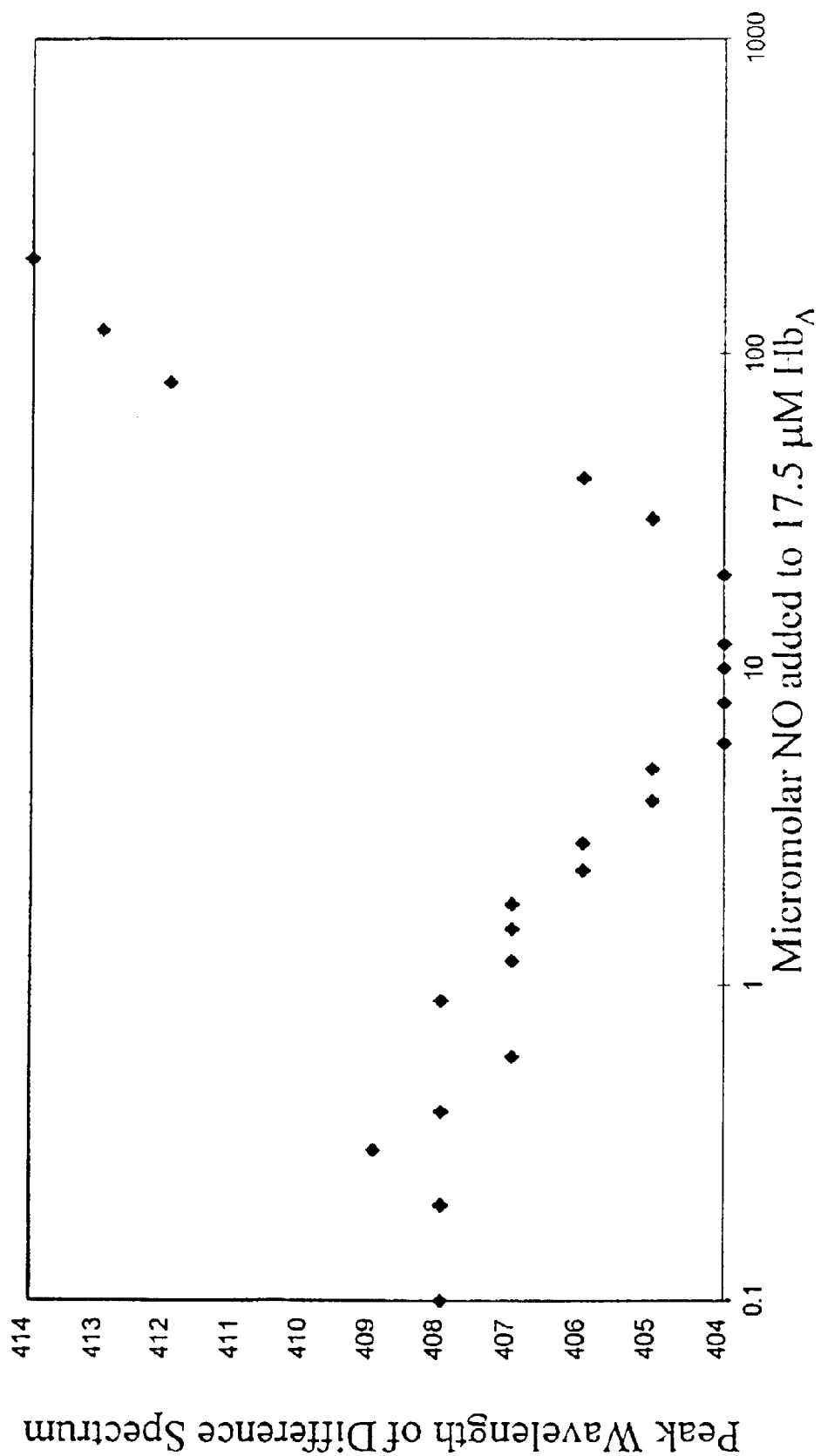

FIG. 14B is a graph showing the peak wavelength of the difference spectra plotted against the concentration of nitric oxide added to the solution as in FIG. 14B.

Figure 15A:
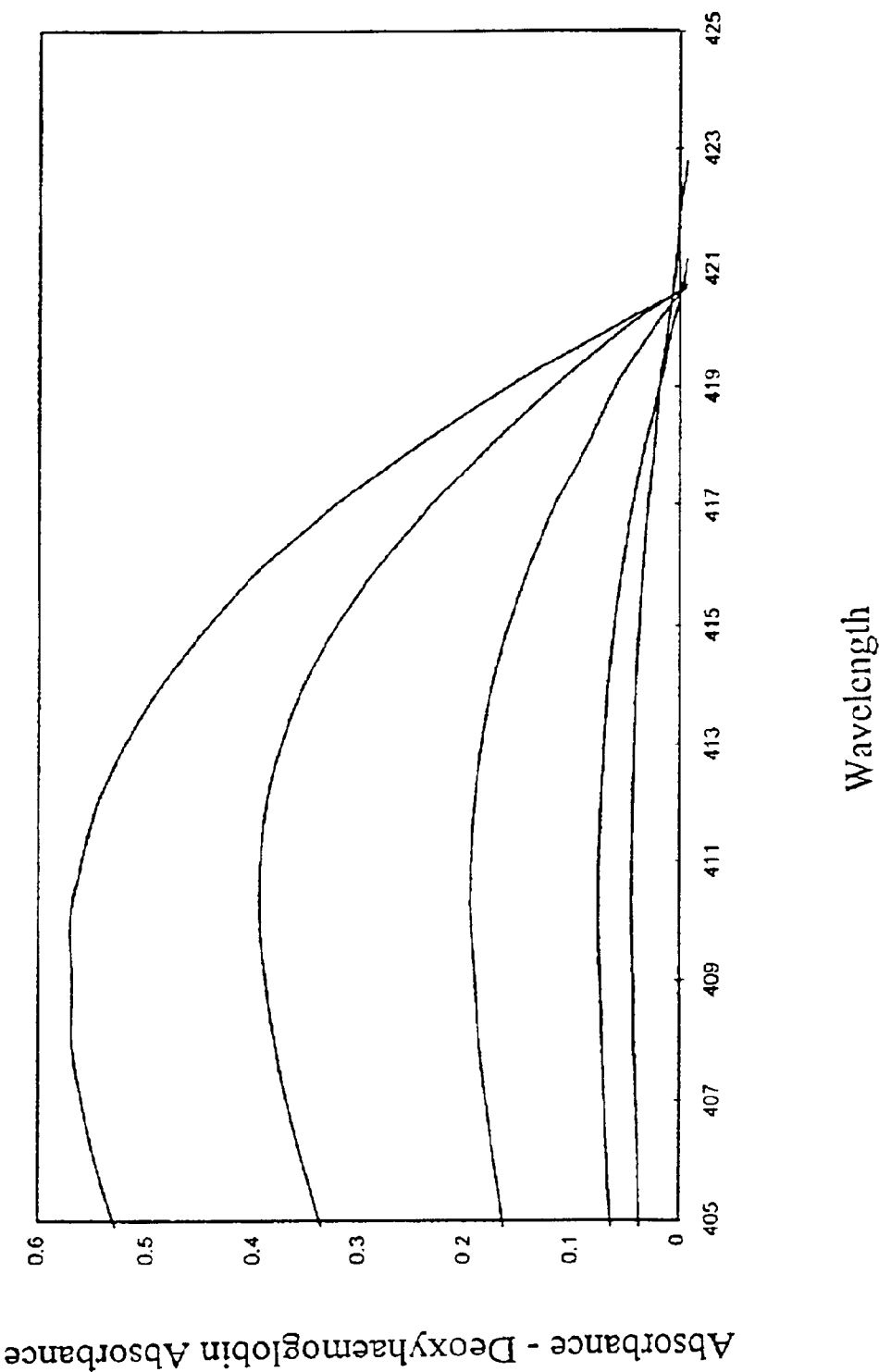

FIG. 15A is a graph showing difference spectra (deoxyhemoglobin and air mixtures minus initial deoxyhemoglobin spectrum), for successive additions of air.

Figure 15B:
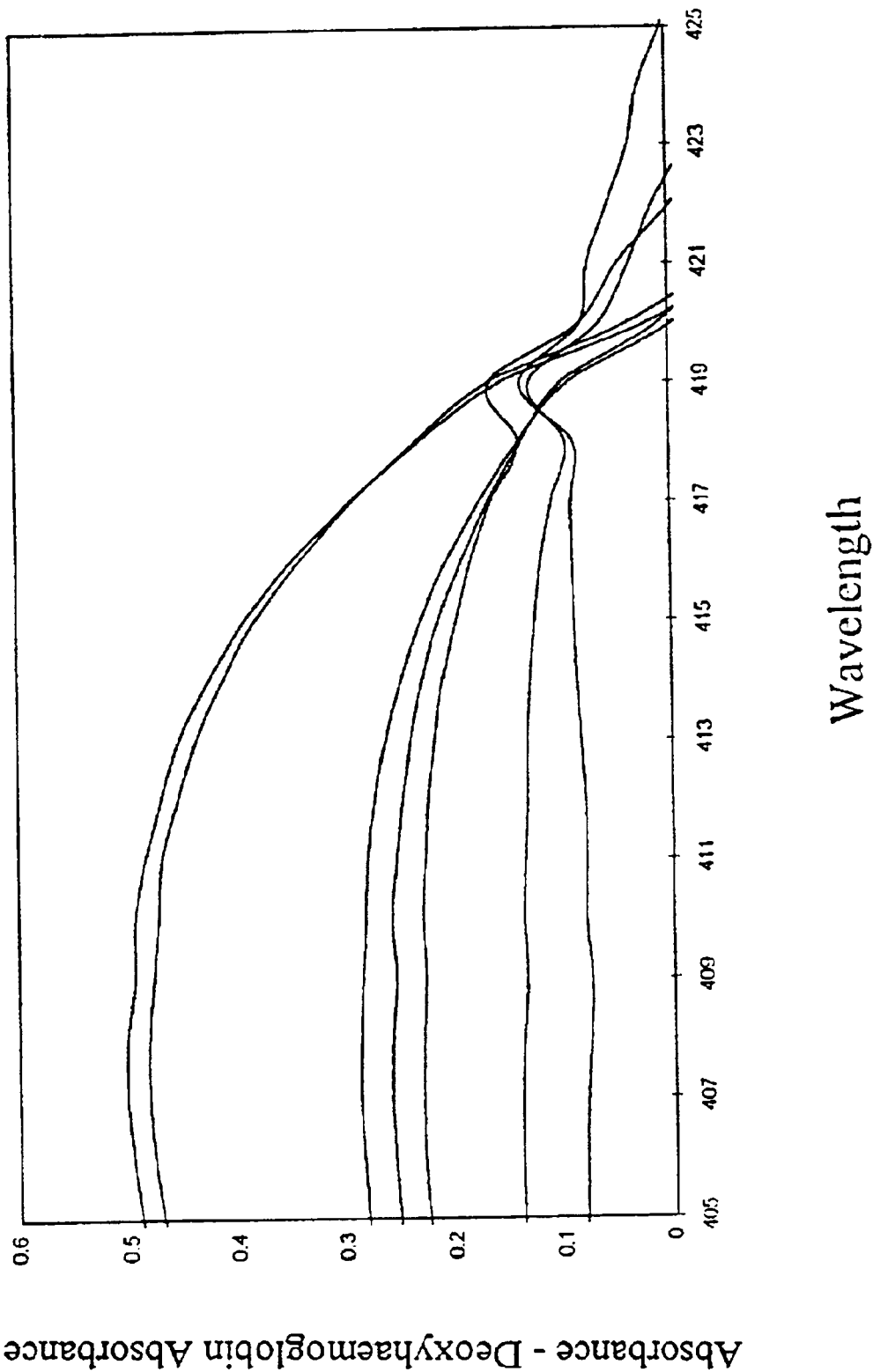

FIG. 15B is a graph showing difference spectra (20 μM deoxyhemoglobin and 1 μM NO mixture, with successive additions of air, minus initial deoxyhemoglobin spectrum). See Example 17.

Figure 16:
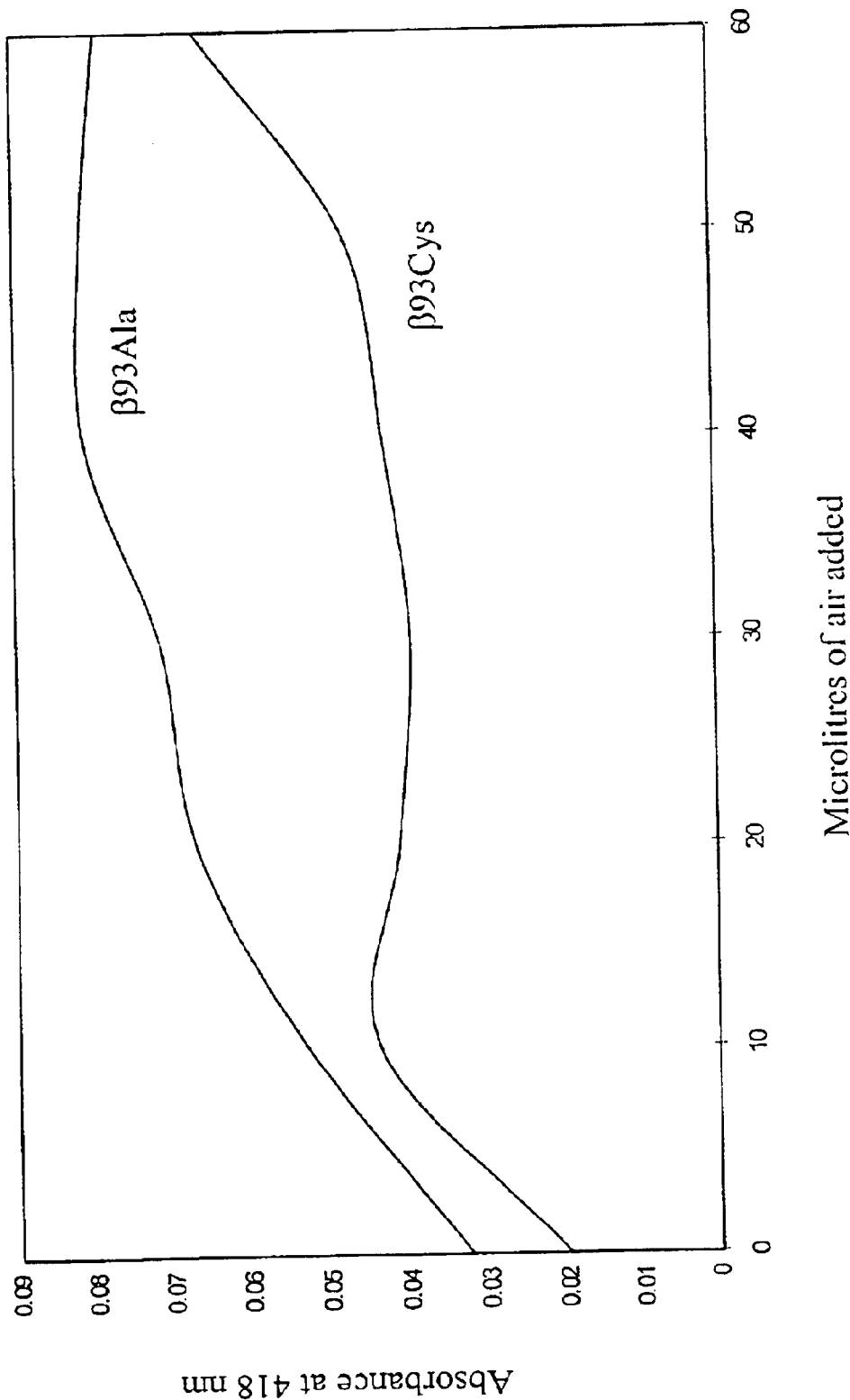

FIG. 16 is a graph showing two difference spectra ($A_{418}$ of hemoglobin and NO solution at heme:NO 20:1 minus initial deoxyhemoglobin $A_{41}8$) for the mutant β93Ala Hb and wild type β93Cys Hb. See Example 18.

Figure 17:
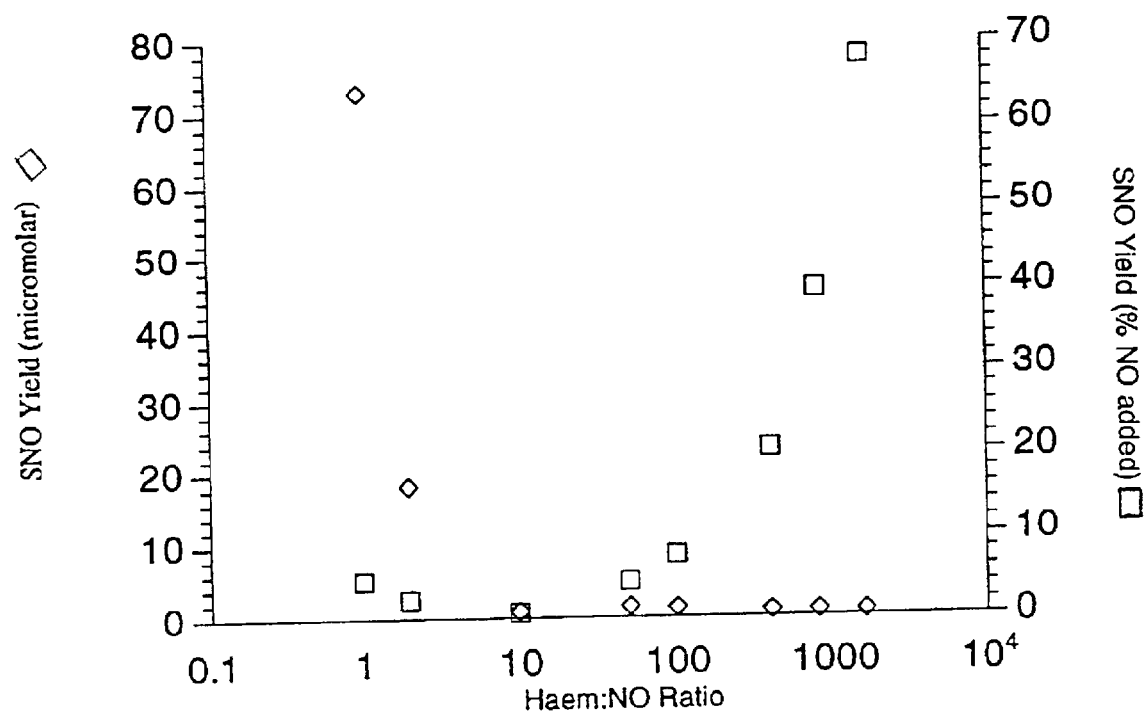

FIG. 17 is a graph showing the yield of SNO-Hb as micromolar concentration (left axis, diamonds) and as % of NO added (right axis, squares), plotted against the heme:NO ratio, when nitrosyl-deoxyHb made at various ratios of heme:NO was exposed to oxygen. See Example 19.

Figure 18A:
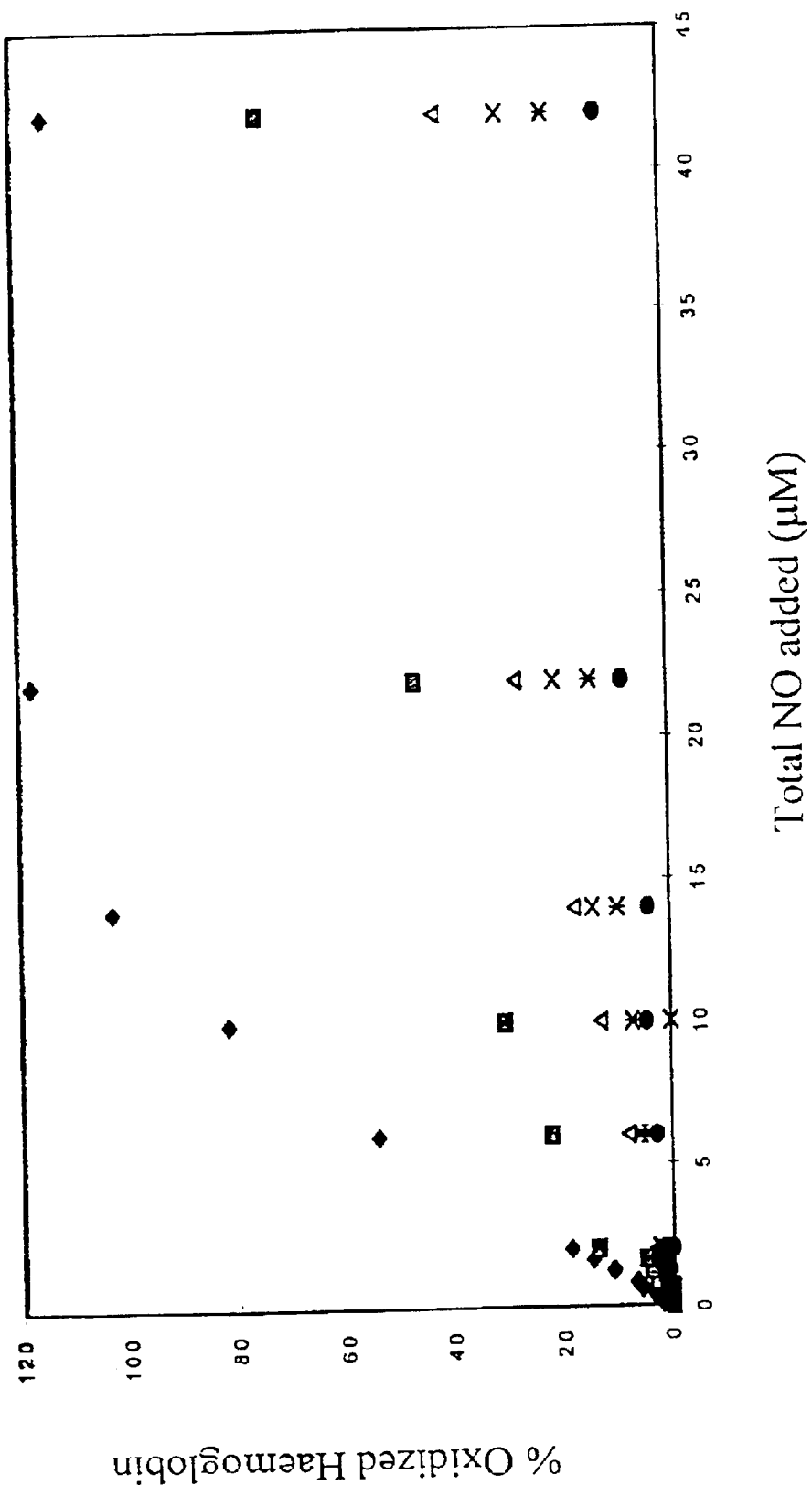

FIG. 18A is a graph showing the percentage content of oxidized hemoglobin (metHb) for different concentrations of Hb (symbols below) to which NO was added to reach varying final concentrations (horizontal axis). ♦ represents 1.26 $\mu$M hemoglobin, ■ represents 5.6 $\mu$M hemoglobin, ▲ represents 7.0 $\mu$M hemoglobin, X represents 10.3 $\mu$M hemoglobin, represents 13.3 $\mu$M hemoglobin, and ● represents 18.3 $\mu$M hemoglobin. See Example 20.

Figure 18B:
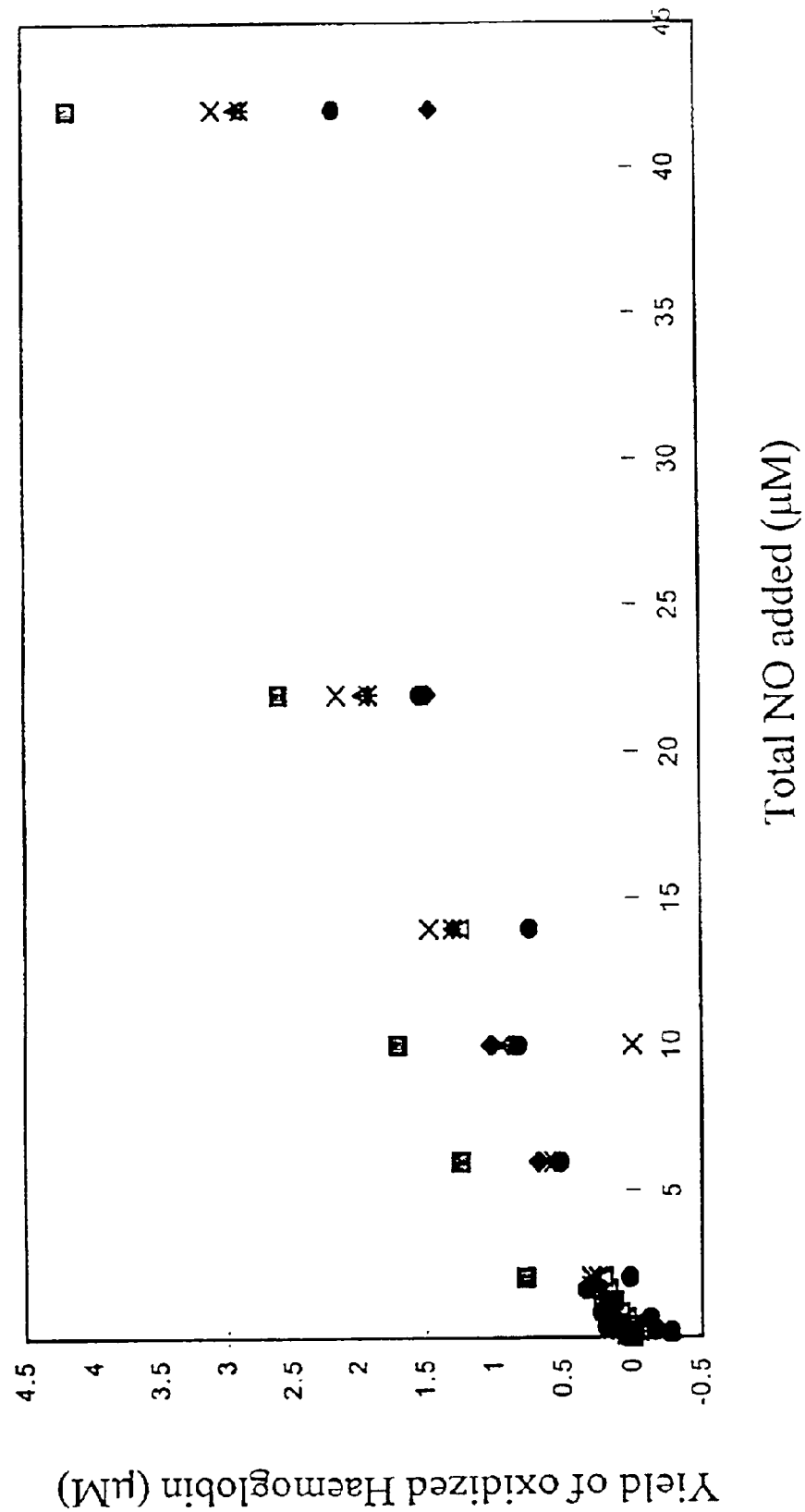

FIG. 18B is a graph showing the yield of oxidized hemoglobin ($\mu$M) plotted against the final concentration of NO added to solutions of Hb at the concentrations indicated by the symbols as for FIG. 18A.

Figure 19:
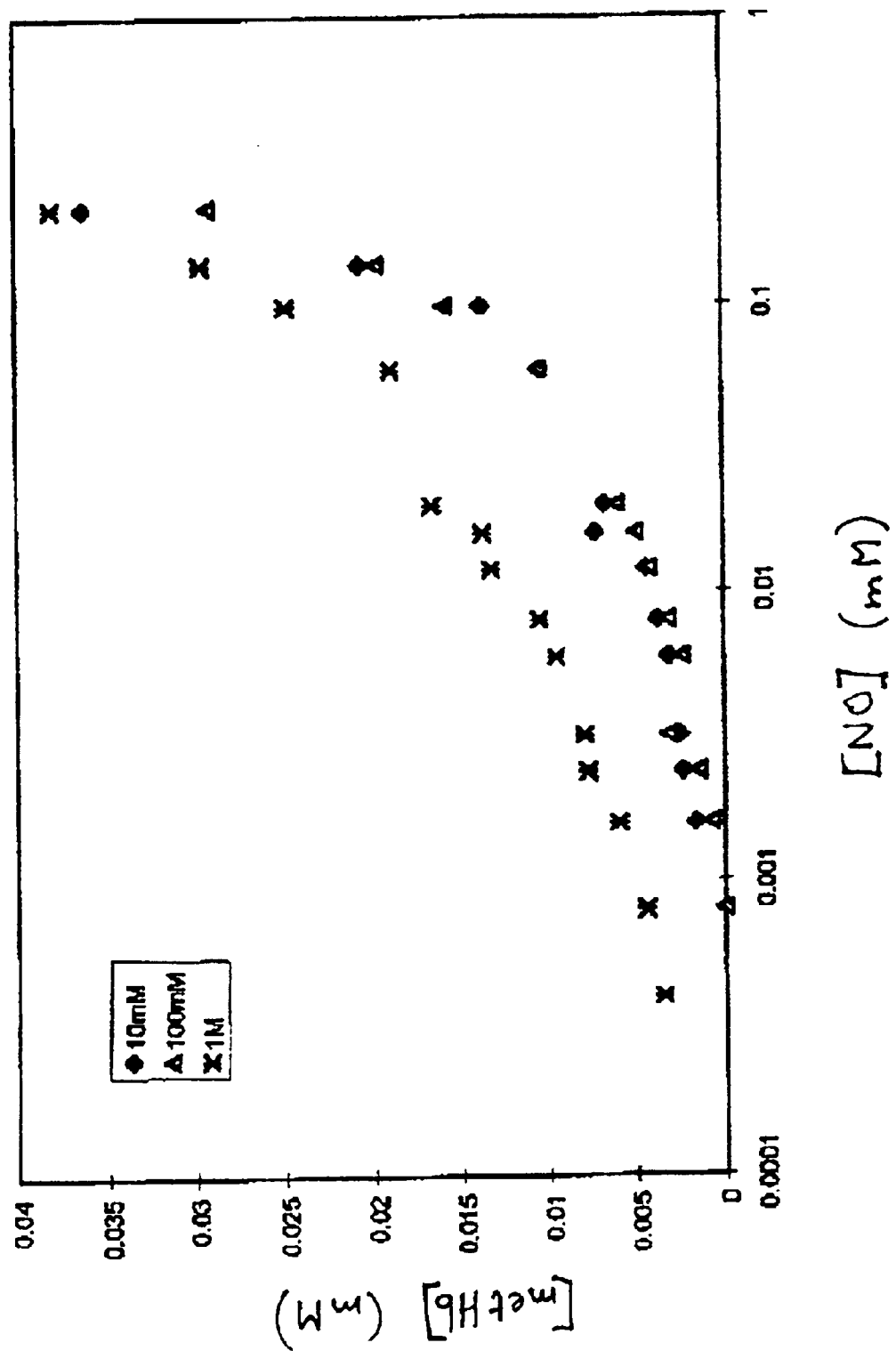

FIG. 19 is a graph showing the concentration of oxidized Hb (metHb) plotted against the NO concentration, in experiments performed as described in Example 21 in 10 mM (♦), 100 mM (Δ), or 1 M (X) sodium phosphate buffer, pH 7.4.

DETAILED DESCRIPTION OF THE INVENTION

Roles for Hemoglobin in Physiology

The increase in SNO-Hb content of red cells across the pulmonary circuit (right ventricular inport-left ventricle) suggests that the Hb molecule is S-nitrosylated in the lung. Selective transfer of the NO group from endogenous RSNOs found in lung (Gaston, et al. (1993) and blood (Scharfstein, J. S. et al., *J. Clin. Invest.* 94:1432–1439 (1995)) to SH groups of Hb, substantiate these findings. The corresponding decline in Hb(FeII)NO levels across the pulmonary bed reveals a role for the lung either in the elimination of NO or in its intramolecular transfer from heme to cysβ93. Taken in aggregate, these data extend the list of function-regulating interactions of Hb with small molecules within the respiratory system, previously known to include the elimination of CO and $CO_2$ and uptake of $O_2$. Since oxygenation of Hb leads to structural changes that increase the NO-related reactivity of cysβ93, $O_2$ may be regarded as an allosteric effector of Hb S-nitrosylation. This is a newly discovered allosteric function for the protein.

The arterial-venous difference in SNO-Hb concentration suggests that the protein acts as an NO group donor in the systemic circulation. There is good indication that SNO-Hb functions in regulation of vasomotor tone. In the microcirculation, where control of blood pressure is achieved, erythrocytes come in intimate contact with endothelial surfaces. Under these conditions, Hb can contract the vasculature by sharply decreasing the steady state level of free NO (Lancaster, J. R., (1994). This is believed to contribute to the increases in blood pressure that occur with infusion of cell-free Hbs (Vogel, W. M., et al., *Am. J. Physiol.*, 251:H413–H420 (1986); Olsen, S. B., et al., Circulation 93:329–332 (1996)). The transient nature of such hypertensive responses, however, is consistent with the subsequent formation of SNO-Hb which counteracts this effect, evidenced by its lowering of blood pressure at naturally occurring concentrations. Thus, the capacity of the erythrocyte to support the synthesis and metabolism of SNO-Hb may well be important for normal blood flow.

Figure 1A:
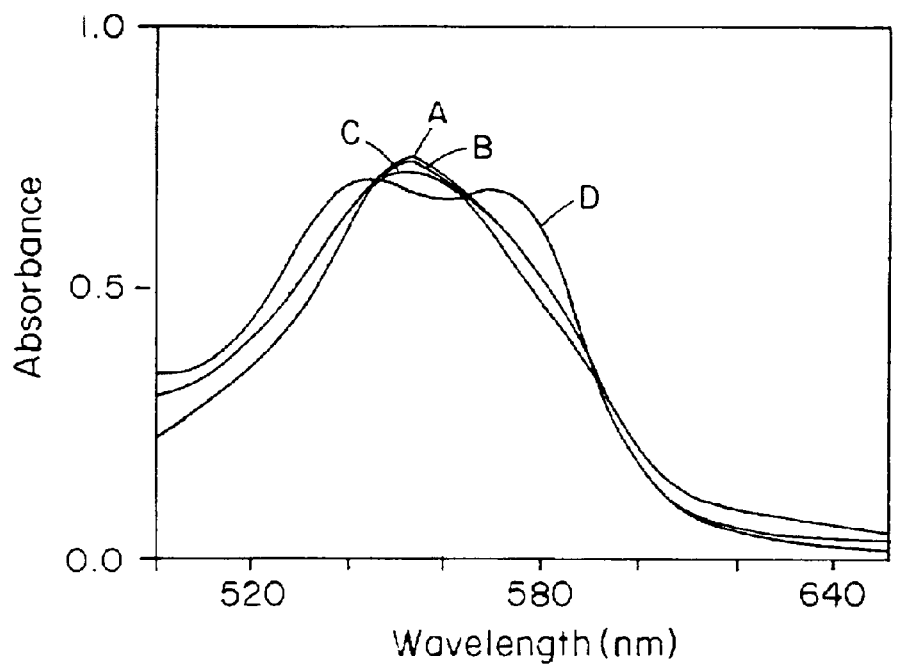
Figure 1B:
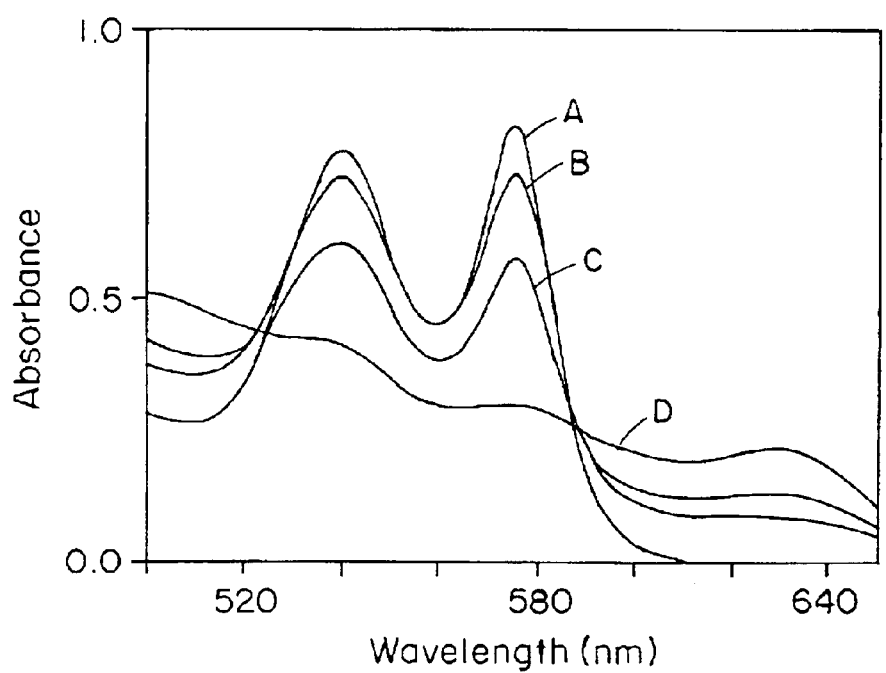
Figure 3A:
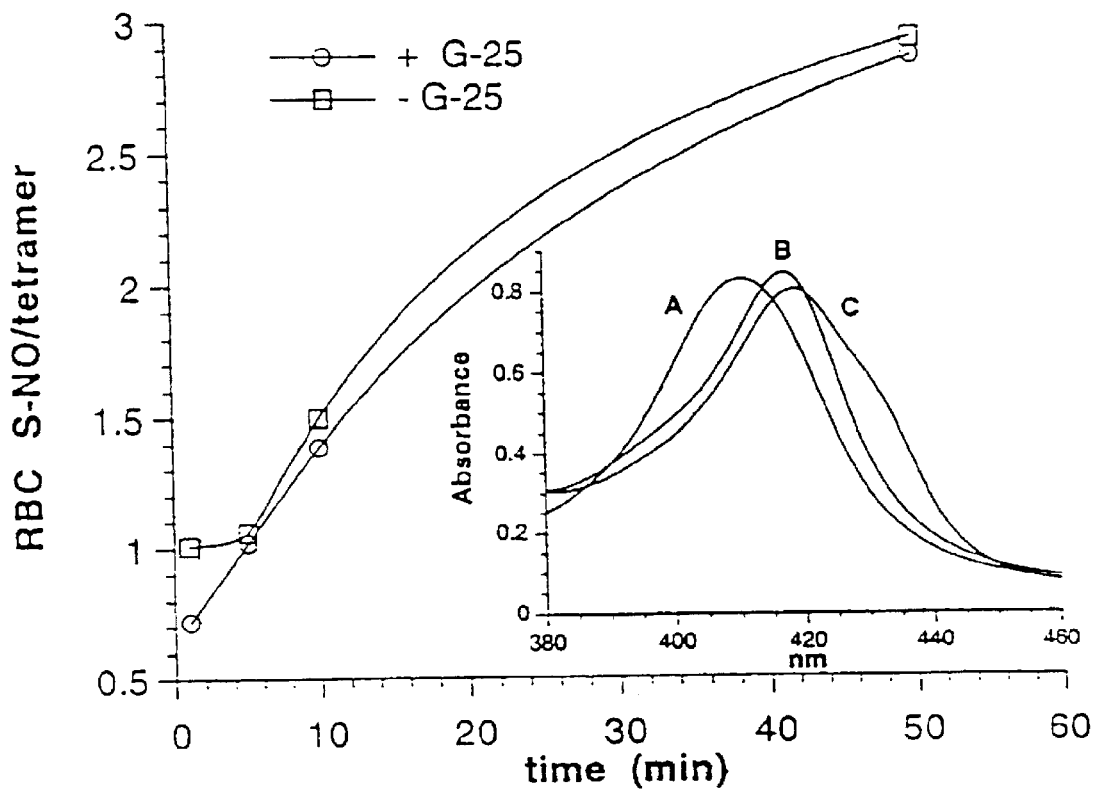
FIG. 3A is a graph showing the loading of red blood cells with S-nitrosocysteine, over time. The inset is a series of spectrographs of forms of Hb as described in Example 3.
Figure 3B:
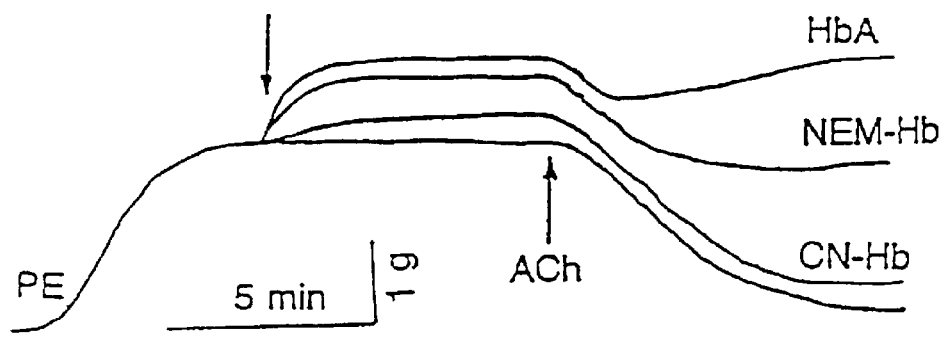
FIG. 3B is a series of tracings recording isometric tone of a rabbit aortic ring following treatment of the aortic ring with various agents as described in Example 3.
Figure 4A:
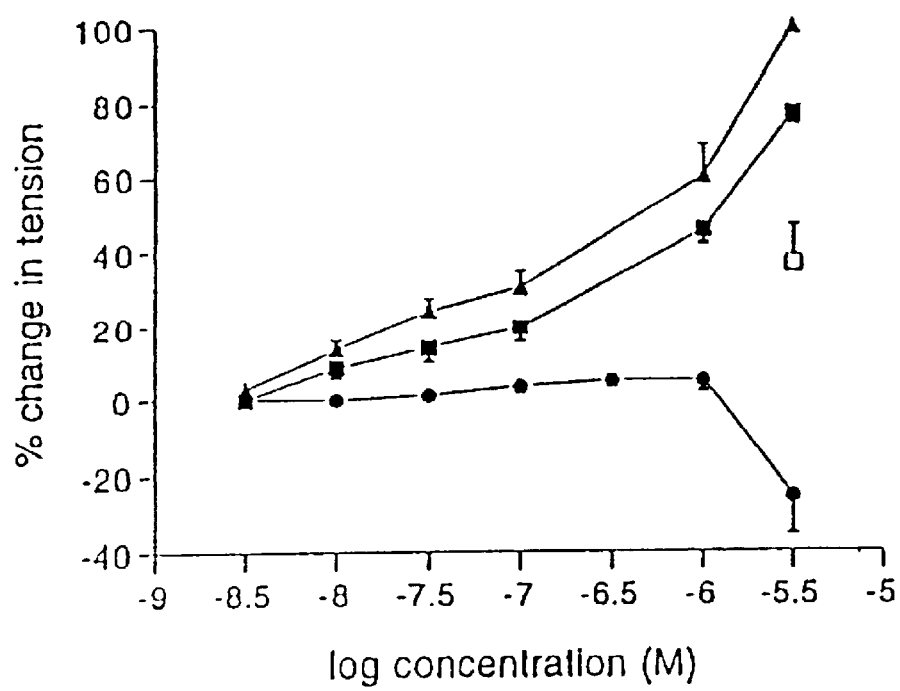
FIG. 4A is a graph of change in tension of a rabbit aortic ring versus concentration of the Hb used in the experiment.

Mammals must have adopted unique molecular mechanisms to ensure adequate NO delivery in the microcirculation. Results herein suggest that Hb may have evolved both electronic and conformational switching mechanisms to achieve NO homeostasis. Specifically, NO scavenging by the metal center(s) of SNO-Hb(FeII)$O_2$ would be sensed through its conversion to met(FeIII) (FIG. 1B). This electronic switch would effect decomposition of SNO-Hb with NO group release (FIGS. 3A, 3B, 4A). In this manner, the NO-related activity of SNO-Hb would be partly determined by the amount of NO scavenged. Changes in $O_2$ tension might also function to regulate NO delivery, as it is observed herein that NO release is facilitated by deoxygenation. This allosteric effect may promote the efficient utilization of $O_2$ as NO controls mitochondrial respiration (Shen, W., et al., Circulation 92:3505–3512 (1995)). It is also possible that NO group release serves to regulate capillary blood flow.

S-nitrosothiol groups in proteins have been implicated in NO metabolism and in regulation of cellular functions (Stamler, J. S., et al., *Proc. Natl. Acad. Sci USA*, 89:444–448 (1992); Stamler, J. S., *Cell*, 78:931–936 (1994)). The identification of SNO-Hb in erythrocytes is the first demonstration of an intracellular S-nitrosoprotein and gives further credence to the role of such proteins in cellular regulation. The question arises as to how SNO-Hb relaxes blood vessels when any free NO released would be scavenged instantaneously by Hb itself (Lancaster, J. R., (1994)). Noteworthy in this regard are studies showing that RSNO activity involves nitrosyl ($NO^+$) transfer to thiol acceptors (Scharfstein, J. S., et al., (1994); Arnelle, D. R. and Stamler, J. S., *Arch. Biochem. Biophys.* 318:279–285 (1995); Stamler, J. S., et al., *Proc. Natl. Acad. Sci USA*, 89:7674–7677 (1992)), which serve to protect the NO-related activity from inactivation at metal centers. Findings presented herein indicate that S-nitrosothiol/thiol exchange with glutathione (forming GSNO) occurs within erythrocytes, and is influenced by the oxidation state of heme and its occupation by ligand. Certain activities of GSNO in bacteria require transport of intact dipeptide (i.e., S-nitrosocysteinylglycine) across the cell membrane (DeGroote, M. A., et al., *Proc. Natl. Acad. Sci. USA* 92:6399–6403 (1995)). The data presented here show that S-nitrosothiol transport happens also in eukaryotic cells. GSNO, or related thiol carriers exported by erythrocytes (Kondo, T., et al., *Methods in Enzymology*, Packer, L., ed., Academic Press, 252:72–83 (1995)), might also initiate signalling in or at the plasmalemma (Stamler, J. S., *Cell*, 78:931–936 (1994)), given reports of thiol-dependent activation of potassium channels by EDRF (Bolotina, V. M., et al., *Nature*, 368:850–853 (1994)). Alternative possibilities also merit consideration. In particular, reports that Hb associates with red cell membranes via cysβ93 (Salhany, J. M. and Gaines, K. C., *Trends in Biochem. Sci.*, Jan, 13–15 (1981)) would place Hb in a position to donate the NO group directly to contacting endothelial surfaces, perhaps via SNO/SH exchange. Cell surface interactions appear to be operative in signaling mediated by other S-nitrosoproteins (Stamler, J. S., et al., *Proc. Natl. Acad. Sci. USA*, 89:444–448 (1992); Stamler, J. S., *Cell*, 78:931–936 (1994)).

The highly conserved Cysβ93 residues in Hb influence the oxygen affinity and redox potential of the heme iron and its physiochemical properties (Garel, C., et al., *Biochem.* 123:513–519 (1982); Jocelyn, P. C., et al., *Biochemistry of the SR Group*, p.243, Academic Press, London; (1972); Craescu, C. T., *J. Biol. Chem.* 261:14710–14716 (1986); Mansouri, A., *Biochem. Biophys. Res. Commun.*, 89:441–447 (1979)). Nonetheless, their long sought-after physiological function has remained a mystery. The studies herein suggest new sensory and regulatory roles for Hb, in which Cysβ93 functions in transducing NO-related signals to the vessel wall. In particular, the physiological function of Cysβ93, which is invariant in all mammals and birds, is to deliver under allosteric control, NO-related biological activity that cannot be scavenged by heme. Thus, these data bring to light a dynamic circuit for the NO group in which intraerythrocytic Hb participates as both a sink and a donor, depending on its microenvironment. Such observations may provide answers to paradoxes that arise from conceptual frameworks based solely on diffusional spread and reaction of free NO (Lancaster, J. R., (1994); Wood and Garthwaite, *J. Neuropharmacology* 33:1235–1244 (1994)); and may have implications that extend to other thiol- and metal-containing (heme) proteins, such as nitric oxide synthase and guanylate cyclase.

The discoveries reported here may have direct therapeutic implications. Specifically, concerns over loss of NO-related activity due to inactivation by blood Hb (Lancaster, J. R., (1994)) are obviated by the presence of an RSNO subject to allosteric control. SNO-Hb is free of the adverse hypertensive properties of cell-free Hb preparations that result from NO scavenging at the metal centers. A cell-free Hb solution that mimics blood by containing SNO-Hb can be used as a blood substitute.

Further Embodiments

The subject invention relates to a method of loading cells with a nitrosating agent as exemplified for red blood cells as in FIG. 3A, but which can be accomplished in more general ways. Suitable conditions for pH and for the temperature of incubation are, for example, a range of pH 7–9, with pH 8 being preferred, and a temperature range of 25 to 37° C. For red blood cells, short incubation times of 1 to 3 minutes are preferred for limiting the formation of S-nitrosylated forms of Hb. However, intracellular concentrations of 1 mM nitrosating agent can be reached.

The nitrosating agent should be a good donor of $NO^+$ and should be able to diffuse through the cell membrane of the target cell type. That is, it must be of low molecular weight, in contrast to S-nitrosoproteins. Examples are S-nitroso-N-acetylcysteine, S-nitrosocysteinylglycine, S-nitrosocysteine, S-nitrosohomocysteine, organic nitrates and nitrites, metal nitrosyl complexes, S-nitro and S-nitroso compounds, thionitrites, diazeniumdiolates, and other related nitrosating agents as defined in Feelisch, M. and Stamler, J. S., "Donors of Nitrogen Oxides" chapter 7, pp. 71–115 In *Methods in Nitric Oxide Research* (Freelisch, M. and Stamler, J. S., eds.) John Wiley and Sons, Ltd., Chichester, U. K. (1996), the contents of which chapter are hereby incorporated by reference in their entirety. Nitrosating agents have differential activities for different reactive groups on metal-containing proteins. A nitrosating agent can be chosen for minimal oxidation of the heme iron of Hb, and maximum activity in nitosylating thiol groups such as found on cysteine. Assay methods are available for detection of nitrosation products, including S-nitrosothiols. See, for example Keefer, L. K., and Williams, D. L. H., "Detection of Nitric Oxide Via its Derived Nitrosation Products," chapter 35, pp. 509–519 in *Methods in Nitric Oxide Research* (Freelisch, M. and Stamler, J. S., eds.) John Wiley and Sons, Ltd., Chichester, U. K., 1996; see also Stamler, J. S. and Feelisch, M., "Preparation and Detection of S-Nitrosothiols," chapter 36, pp. 521–539, ibid. Nitrite and nitrate products can be assayed by methods described, for instance, in Schmidt, H. H. H. W. and Kelm, M., "Determination of Nitrite and Nitrate by the Griess Reaction," chapter 33, pp. 491–497, ibid., and in Leone, A. M. and Kelm, M., "Capillary Electrophoretic and Liquid Chromatographic Analysis of Nitrite and Nitrate," chapter 34, pp. 499–507, ibid.

Such low molecular weight nitrosating agents can be used in red blood cells to deliver NO-related activity to tissues. Treatment of red blood cells with nitrosating agent further serves to increase the $O_2$ delivery capacity of red blood cells. Such treatment of red blood cells also allows for the scavenging of oxygen free radicals throughout the circulation. Therefore, it is possible to load red blood cells with S-nitrosothiol, for example, by a process outside a patient's body after removal of whole blood (as a minimal method of isolating the red blood cells) and then to reintroduce the red blood cells into the same patient, thereby allowing the treatment of a number of types of diseases and medical disorders, such as those which are characterized by abnormal $O_2$ metabolism of tissues, oxygen-related toxicity, abnormal vascular tone, abnormal red blood cell adhesion, or abnormal $O_2$ delivery by red blood cells. Such diseases can include, but are not limited to, ischemic injury, hypertension, shock, angina, stroke, reperfusion injury, acute lung injury, sickle cell anemia, schistosomiasis and malaria. The use of such "loaded" red blood cells also extends to blood substitute therapy and the preservation of living organs, as organs for transplantation, for example. In some cases, it may be appropriate to treat a patient with loaded red blood cells originating from a different person.

A particular illustration of the mechanism of the treatment method is presented here by considering sickle cell anemia. Sickle cell patients suffer from frequent vascular occlusive crises which manifest in clinical syndromes such as the acute chest syndrome and hepatic dysfunction. Both endothelial cell dysfunction, resulting in a clotting diathesis as well as dysfunction intrinsic to the red blood cell, are central to disease pathogenesis. At the molecular level, the increased expression of vascular adhesion molecules such as VCAM promote the adhesion of sickled red blood cells containing abnormal hemoglobin. It follows that decreasing cytokine expression on endothelial cells, promoting endothelial function and attenuating red cell sickling, are key therapeutic objectives. However, currently used therapies have been generally unsuccessful.

In this novel method for loading red blood cells with intracellular NO-donor S-nitrosothiols, the effect is to increase oxygen affinity—which in and of itself should attenuate red blood cell sickling—and to endow the red blood cell with vasodilator and antiplatelet activity, which should reverse the vasoocclusive crisis. Moreover, nitric oxide should attenuate the expression of adhesion molecules on endothelial cell surfaces, thus restoring endothelial function.

Herein is described a novel therapeutic approach to the treatment of sickle cell disease which involves loading of red blood cells with S-nitrosothiols or other nitrosating agents. Two examples of therapeutic approaches are given. In the first, the patient's own red blood cells are S-nitrosated extracorporeally (yielding "loaded" red blood cells) and then given to the patient. The second approach is to directly administer to a patient an agent such as S-nitrosocysteine, which is permeable to red blood cells.

For some diseases or disorders, the administration of NO-loaded red blood cells is especially desirable. Upon a change from the oxygenated to the deoxygenated state, or upon a change in the oxidation state of the heme Fe from the reduced state (FeII) to the oxidized (FeIII) state, NO is released from the thiol groups of hemoglobin, and is rapidly transferred to glutathione to form S-nitrosoglutathione. Red blood cells are known to have a high concentration of glutathione. S-nitrosoglutathione efficiently delivers NO to tissues.

In another aspect, the invention is a method for the treatment of infection by administering to an infected mammal an agent which causes S-nitrosation of thiol groups within the cells which are the target of such agent. For example, an S-nitrosothiol to which lymphocytes are highly permeable can be administered to a patient infected with HIV. Such treatment for HIV can also be used excorporeally, to blood isolated from the patient. In another application, the infection is bacterial, and the S-nitrosothiol to be used as an anti-bacterial agent is one to which the target bacterial cells are highly permeable, as compared to the permeability properties of the host cells. (See, for example De Groote, M. A., et al., *Proc. Natl. Acad. Sci. USA* 92:6399–6403 (1995).) Alternatively, nitrosothiols can be used to treat *Plasmodium falciparum* within red blood cells.

Another embodiment of the invention is a method for specifically modifying a protein containing one or more metal atoms so that the protein becomes S-nitrosylated at one or more thiol groups without modifying the metal, as by changing the oxidation state or causing the metal atoms to bind NO. This can be accomplished by the use of a reagent which possesses $NO^+$ character, such as a nitrosothiol (See, for instance, Example 4A.), which reacts specifically with thiol groups of a protein in which metal is bound.

An S-nitrosation method has been devised which does not affect the heme of hemoglobin. SNO-Hb (SNO-Hb(FeII)$O_2$) can be synthesized from Hb(FeII)$O_2$ with up to 2 SNO groups per tetramer without oxidation of the heme Fe from FeII to FeIII. In contrast, when Hb(FeII)$O_2$ is incubated with excess nitric oxide or nitrite, methemoglobin (HbFe[III]) forms rapidly (Example 1B) and to a significant extent. When Hb[FeII] is incubated with nitric oxide, NO binds rapidly to the heme, forming Hb(FeII)NO to a significant extent (Example 1A).

Although rates of formation of SNO-Hb(FeII)$O_2$ from Hb(FeII)$O_2$ are more rapid (see Example 2A), the corresponding SNO-deoxyHb form can also be made by incubation of S-nitrosoglutathione or S-nitrosocysteine, for example, with Hb(FeII), yielding SNO-Hb(FeII), as in Example 1C.

The effects of the various forms of Hb on vasodilation—constriction, dilation or a neutral effect—depend on three factors: whether 1) the Fe of the heme is oxidized, 2) $O_2$ is bound at the heme (that is, the oxygenation state, dictated by the conformation of the protein as R state or T state), and 3) thiol is present in sufficient concentration to facilitate the transfer of $NO^+$.

The importance of the first factor is shown in FIG. 4A. Hb(FeII)$O_2$ and SNO-Hb[FeII]$O_2$ act as vasoconstrictors, but SNO-Hb[FeIII] (metHb form, where FeII has been oxidized to FeIII) acts as a vasodilator. FIG. 4A shows that SNO-Hb[FeII]$O_2$ with oxygen bound at the heme, and with a ratio of SNO/Hb=2, acts as a powerful vasoconstrictor.

Figure 2A:
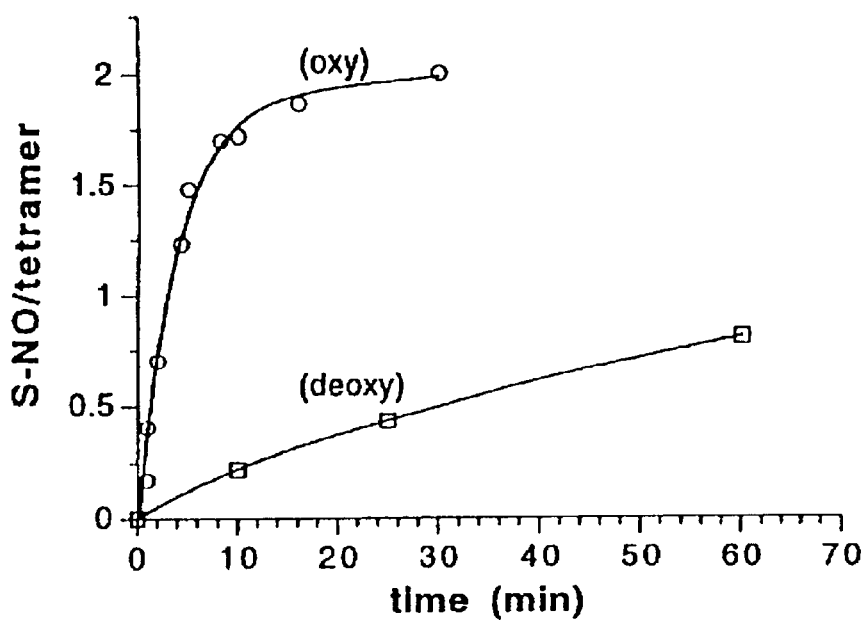
FIG. 2A is a graph showing formation, with time, of SNO-Hb by S-nitrosylation.
Figure 2B:
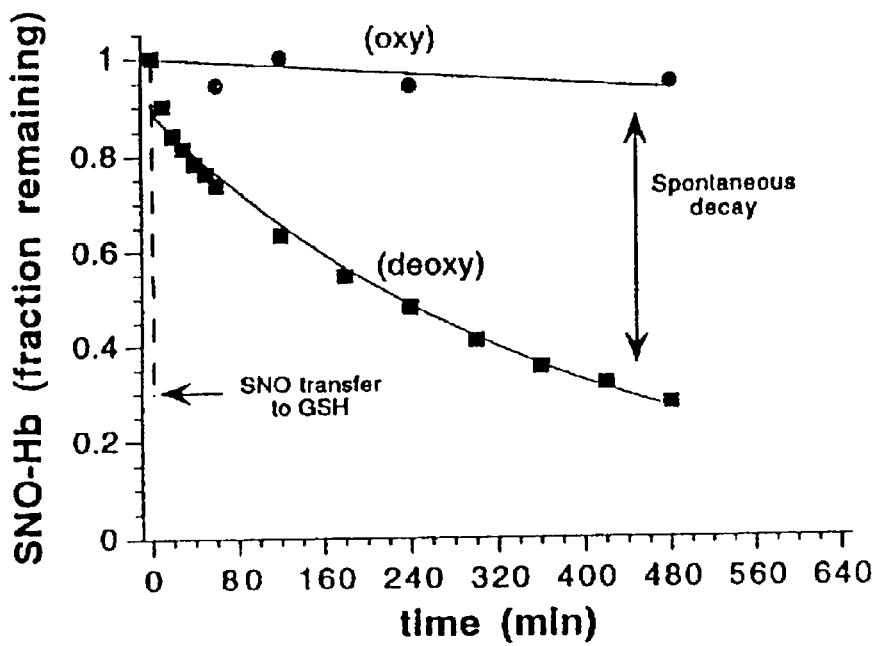
FIG. 2B is a graph showing the decomposition, with time, of oxy and deoxy forms of SNO-Hb.

SNO-Hb(FeII) is also a vasodilator. FIG. 2B illustrates the second factor in demonstrating that rates of RSNO decomposition and transfer are much faster for SNO-Hb in the deoxy state than for SNO-Hb in the oxy state.

It can be seen how the $NO^+$-donating properties of SNO-Hb depend on oxygen concentrations. SNO-Hb releases oxygen at sites of low oxygen concentration or under oxidizing conditions. SNO-Hb releases its NO group(s) to cause vasodilation either due to 1) oxidation of the heme Fe to FeIII or 2) loss of the $O_2$ from the heme by deoxygenation. It is shown in FIG. 2B that NO is transferred off SNO-Hb best in the deoxy state. In ischemia, SNO-Hb deoxygenates, rapidly followed by the loss of NO. It can be seen from the data that SNO-metHb having a ratio of 1 SNO/SNO-metHb is a more powerful vasodilator than SNO-oxyHb having a ratio of 2 SNO/SNO-oxyHb. It should be noted that S-nitrosation of Hb induces the R state (oxy conformation). Thus, it follows that 1 SNO-oxyHb molecule having a ratio of 1 SNO/SNO-oxyHb is less potent than 10 molecules of SNO-oxyHb having a ratio of 0.1 SNO/SNO-oxyHb.

Figure 4B:
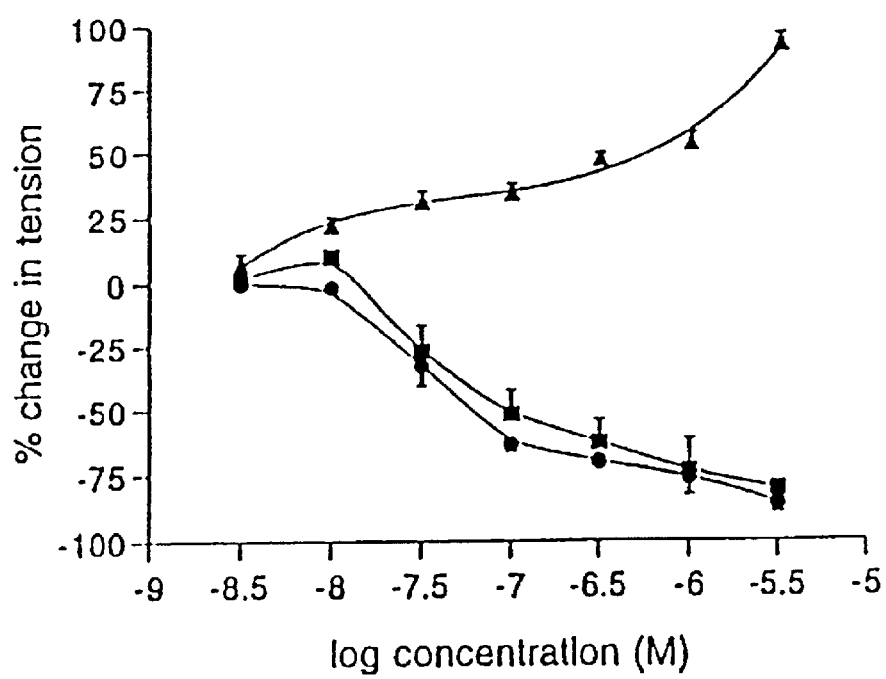
FIG. 4B is a graph of change in tension of a rabbit aortic ring versus concentration of the Rb used in the experiment, where glutathione was also added to test the effect as compared to FIG. 4A.
Figure 4C:
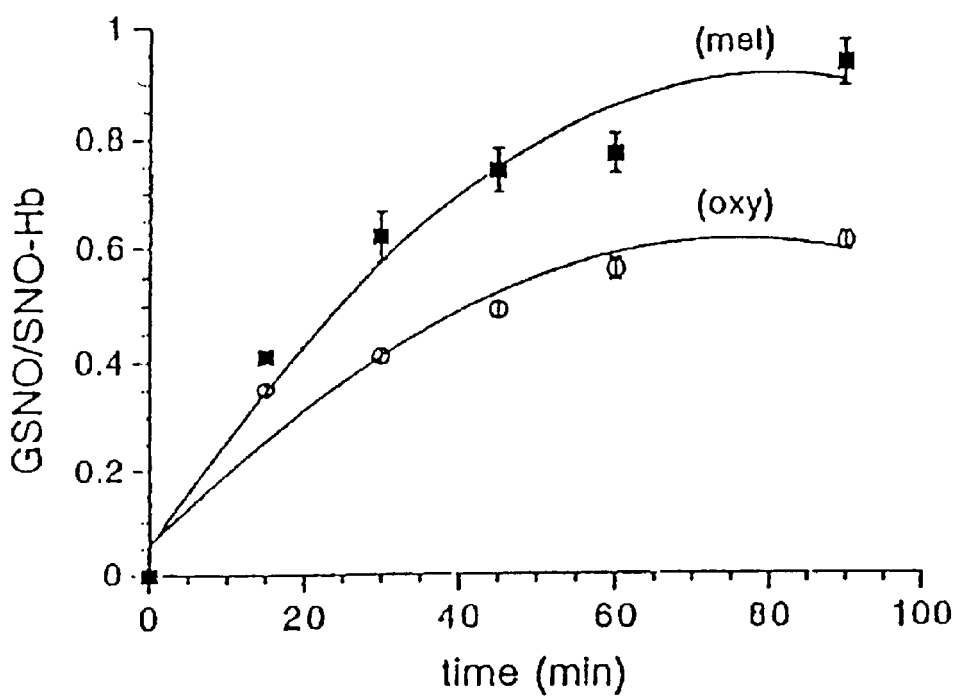
FIG. 4C is a graph of the ratio of S-nitrosoglutathione formed/starting SNO-Hb concentration versus time, showing rates of NO group transfer from oxy and met forms of Hb to gluthiathione.

The third factor is illustrated by the results shown in FIG. 4B. These results demonstrate potentiation by thiol of the vasodilator effect of SNO-Hb(FeII)$O_2$ and SNO-Hb(FeIII). Transfer of $NO^+$ from SNO-Hb to low molecular weight nitrosothiols is more efficient when Hb is in the deoxy state compared to the oxy state (FIG. 2B) or in the met state compared to the oxy state (FIG. 4C).

NO is released or transferred as $NO^+$ (nitrosyl cation) from SNO-HB. The SNO groups of SNO-Hb have $NO^+$ character. Transfer of $NO^+$ from SNO-Hb occurs most efficiently to small thiols, such as glutathione, and is most efficient when the heme is oxidized (SNO-metHb) or the SNO-Hb is in the deoxy state.

One embodiment of the invention resulting from these findings is a method of therapy that enhances the transfer of NO+from SNO-Hb to small thiols, thereby delivering NO biological activity to tissues, by the coadminstration of low molecular weight thiols, along with a form of SNO-Hb, to a mammal in need of the physiological effects of NO. To further increase the effect of NO release it is preferred that the SNO— forms of metHb or deoxyHb (or an equivalent conformation or spin state) be administered with the thiol (See FIG. 2B, for example.) A mixture of SNO-metHb and SNO-oxyHb, and possibly also thiol, can also be used. The composition and proportion of these components depends on the disease state. For example, to achieve both enhanced $O_2$ delivery and NO delivery, SNO-oxyHb can be used. Where no further delivery of $O_2$ is desirable, as in acute respiratory distress syndrome, for example, the SNO- forms of metHb and deoxyHb are especially preferred. Alternatively, the ratios of SNO/Hb can be regulated to control $O_2$ release.

Figure 5:
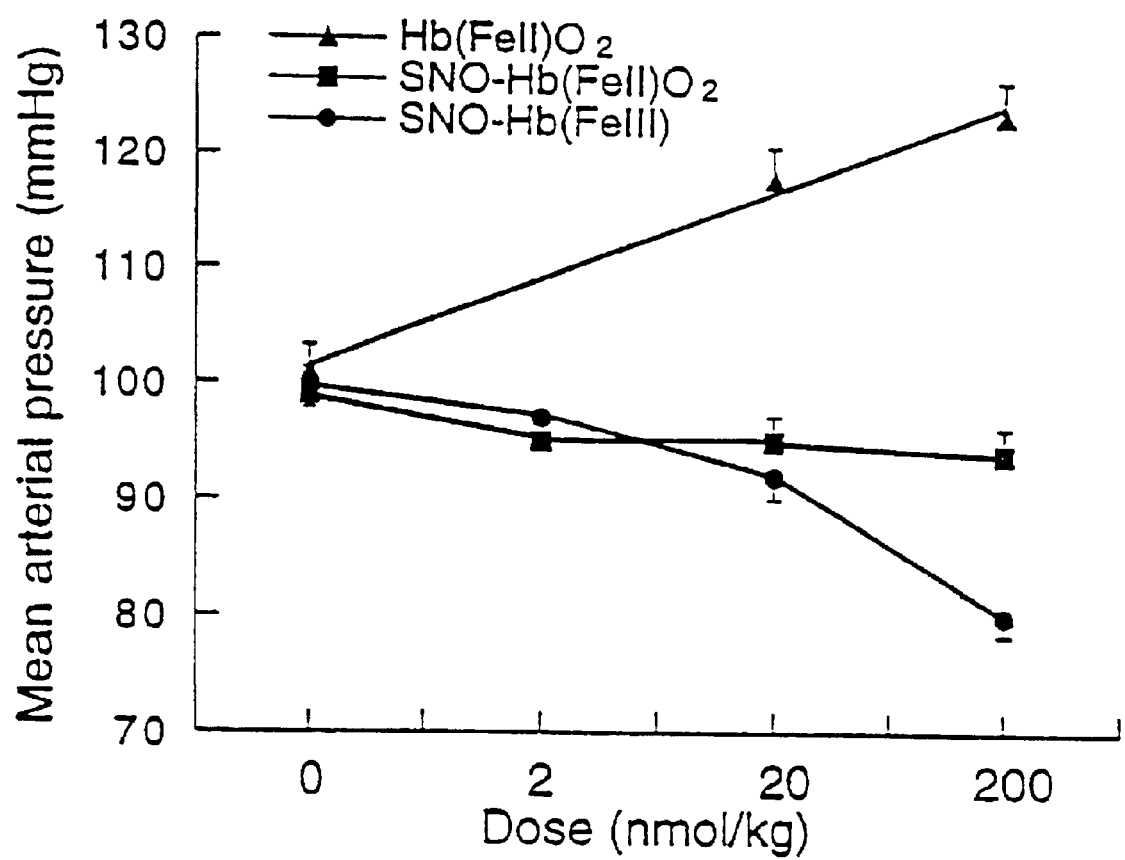
FIG. 5 is a graph showing the mean arterial blood pressure in rats after they received various doses of oxyHb (▲), SNO-oxyHb (■), or SNO-metHb (●).

The vessel ring bioassay data of FIG. 4A agree well with the in vivo data of FIG. 5. The results of the experiments described in Example 5 confirm that Hb(FeII)$O_2$ (oxyHb) causes an increase in blood pressure in vivo, as it did also in vitro. SNO-Hb(FeIII) (SNO-metHb) causes a decrease in blood pressure in vivo as well as in vitro. SNO-Hb(FeII)$O_2$ (SNO-oxyHb) has a negligible effect on blood pressure in vivo in contrast to the increase in tension seen in the corresponding vessel ring bioassay. For SNO-oxyHb the in vivo effect is neutral. This may be explained by the constrictive effect caused by NO becoming bound to the heme being compensated by the release of NO upon deoxygenation. Therefore, SNO-oxyHb can deliver $O_2$ with minimal effect on blood pressure.

With knowledge of the results herein it is possible to synthesize Hb proteins with predicted NO-releasing properties, which will constrict, dilate, or have no effect on blood vessels. An additional option is the choice between making oxygenated or deoxygenated forms to administer for medical conditions in which $O_2$ delivery is desirable, or undesirable, respectively.

It is possible to produce a variety of modified Hbs having specific desired properties of $O_2$ and NO delivery. For example, Hb in the R state or R-structure (oxyHb) can be converted to the T state or T-structure (deoxyHb) by a number of known methods. This can be done, for example, by reaction of Hb with inositol hexaphosphate. It is also known to those skilled in the art that Hb in the R state can be made, for example, by treating Hb with carboxypeptidase. Similarly, it is known that metHb can be synthesized using ferricyanide or nitrite.

Producing Hb molecules which are locked in the T state allows the synthesis of RSNO-Hb which remains in a form that is a biologically active donor of NO, rather than a carrier of NO. Hb which is locked in the R state can be used as a substrate for the synthesis of RSNO-Hb which carries a maximum amount of NO per molecule.

Another embodiment of the invention is a blood substitute comprising one or more forms of Hb which have been specifically S-nitrosated to some extent at one or more thiol groups of the Hb, in order to regulate $O_2$ release and NO release. Conditions to be treated include those in which NO or $O_2$ delivery is desired, those in which NO or $O_2$ utilization is desired, or those in which NO or $O_2$ is in excess. For example, in a medical condition which is characterized by the presence of an excess of oxygen free radicals and excess NO·, both the heme of SNO-Hb and NO released by SNO-Hb serve to trap oxygen free radicals. The heme Fe is oxidized in the process of scavenging oxygen free radicals and NO·, and NO is released from the oxidized Hb by donation to a thiol, in the form of $RSNO^+$, which is not toxic. Inflammation and reperfusion injury, for example, are characterized by excess NO production and an excess of oxygen free radicals. Forms of Hb scavenge oxygen radicals and free NO, converting NO to forms that are not toxic.

A further embodiment of the invention is a method of therapy for a condition that would benefit from the delivery of NO in a biologically active form or $O_2$ or both, based on the administration of a blood substitute comprising a form of nitrosated Hb. For example, SNO-Hb is useful to treat myocardial infarction. SNO-Hb has the effect of donating NO, keeping blood vessels open. SNO-Hb deoxygenates at low oxygen tension, delivering oxygen and releasing NO at the same site, thereby causing vasodilation. (See Example 7 and FIGS. 6A–6F.) These effects can be augmented by also administering thiol, either simultaneously with SNO-Hb, or before or after. For the purpose of treating myocardial infarction, for example, a high concentration or dose of SNO-Hb that has a low ratio of SNO/SNO-Hb is appropriate. Alternatively, SNO-metHb can be used for this purpose.

In another aspect, the invention is a method of enhancing NO-donor therapy by coadministering SNO-Hb or other forms of nitrosated Hb together with a nitroso-vasodilator (nitroglycerin, for example) which would be otherwise consumed by the conversion of oxyHb to metHb in Hb which has not been S-nitrosated.

Platelet activation is manifested by a number of events and reactions which occur in response to adhesion of platelets to a nonplatelet surface such as subendothelium. Binding of agonists such as thrombin, epinephrine, or collagen sets in motion a chain of events which hydrolyzes membrane phospholipids, inhibits adenylate cyclase, mobilizes intracellular calcium, and phosphorylates critical intracellular proteins. Following activation, platelets secrete their granule contents into plasma, which then allow the linking of adjacent platelets into a hemostatic plug. (See pages 348–351 in *Harrison's Principles of Internal Medicine,* 12th edition, eds. J. D. Wilson et al., McGraw-Hill, Inc., New York, 1991).

A thrombus is a pathological clot of blood formed within the circulatory system. It may remain attached to its place of origin or become dislodged and move to a new site within the circulatory system. Thromboembolism occurs when a dislodged thrombus or part of a thrombus partially or completely occludes a blood vessel and prevents oxygen transport to the affected tissues, ultimately resulting in tissue necrosis.

Sites where damage has occurred to the vascular surface are especially susceptible to the formation of thrombi. These sites include those on the interior surface of a blood vessel in which damage to the endothelium, narrowing or stenosis of the vessel, or atherosclerotic plaque accumulation has occurred.

NO is one of several endothelium-derived thromboregulators, which are defined as physiological substances that modulate the early phases of thrombus formation. In particular, NO reduces platelet adhesion, activation and recruitment on the endothelial cell surface, and achieves this, it is thought, by activating platelet guanylate cyclase, thereby increasing platelet intracellular cGMP-(Stamler, J. S. et al, *Circ. Res.* 65:789–795 (1989)), and decreasing intraplatelet $Ca^{2+}$levels. NO and the prostacylcin prostaglandin (PG) $I_2$ act synergistically to inhibit and actively mediate platelet disaggregation from the collagen fibers of the subendothelial matrix. Unlike prostacyclin, NO also inhibits platelet adhesion. Furthermore, platelets synthesize NO, and the L-arginine-NO pathway acts as an intrinsic negative feedback mechanism to regulate platelet reactivity. NO is involved in leukocyte interactions with the vessel wall and can inhibit neutrophil aggregation. (See review article, Davies, M. G. et al., *British Journal of Surgery* 82:1598–1610, 1995.)

NO is antiathrogenic in a number of ways. (See, for example, Candipan, R. C. et al., *Arterioscler. Thromb. Vasc. Biol.* 16:44–50, 1996.) NO inhibits smooth muscle proliferation and attenuates LDL (low density lipoprotein) oxidation and other oxidant-related processes.

Hemoglobin may promote atherosclerosis as well as thrombosis as a consequence of its NO-scavenging property. This limitation of hemoglobin derives from its high affinity for nitric oxide. In vitro, NO is a potent inhibitor of platelet aggregation and adhesion to collagen fibrils, the endothelial cell matrix and monolayers (Radomski, M. W. et al., *Br. J. Pharmacol.* 92:181–187 (1987); Radomski, M. W. et al., *Lancet* 2:1057–1058 (1987); Radomski M. W. et al., *Biochem. Biophys. Res. Commun.* 148:1482–1489 (1987)). NO elevates cGMP levels in platelets, thereby decreasing the number of platelet-bound fibrinogen molecules and inhibiting intracellular $Ca^{++}$ flux and platelet secretion (Mellion, B. T. et al., *Blood* 57:946–955 (1981); Mendelson, M. E. et al., *J. Biol. Chem.* 165:19028–19034 (1990); Lieberman, E. et al., *Circ. Res.* 68:1722–1728 (1991)). Scavenging of nitric oxide by Hb prevents the molecule from inhibiting platelets. This explanation has been given support by in vivo studies (Krejcy, K. et al., *Arterioscler. Thromb. Vasc. Biol.* 15:2063–2067 (1995)).

The results shown in FIGS. 7A–7C (see Example 9) show that nitrosated hemoglobins, including SNO-Hb, can be used in the treatment of acute blood clotting events that occur as a result of increased platelet deposition, activation and thrombus formation or consumption of platelets and coagulation proteins. Such complications are known to those of skill in the art, and include, but are not limited to myocardial infarction, pulmonary thromboembolism, cerebral thromboembolism, thrombophlebitis and unstable angina, and any additional complication which occurs either directly or indirectly as a result of the foregoing disorders.

SNO-Hb and other nitrosated hemoglobins can also be used prophylactically, for example, to prevent the incidence of thrombi in patients at risk for recurrent thrombosis, such as those patients with a personal history or family history of thrombosis, with atherosclerotic vascular disease, with chronic congestive heart failure, with malignancy, or patients who are pregnant or who are immobilized following surgery.

NO is known to activate soluble guanylate cyclase, which produces CGMP. CGMP mediates inhibition of platelet aggregation. Results in Example 10 demonstrate that this inhibition of platelet aggregation may be mediated not by CGMP alone, but by some other mechanism as well.

Certain compounds or conditions are known to cause a shift in the allosteric equilibrium transition of Hb towards either of the two alternative quaternary structures of the tetramer, the T- or R-structures. (See, for example, pages 7–28 in Perutz, M., *Mechanisms of Cooperativity and Allosteric Regulation in Proteins*, Cambridge University Press, Cambridge, U. K., 1990.) These are, for instance, the heterotropic ligands $H^+$, $CO_2$, 2,3-diphosphoglycerate (2,3-DPG) and $Cl^-$, the concentrations of which modulate oxygen affinity. The heterotropic ligands lower the oxygen affinity by forming additional hydrogen bonds that specifically stabilize and constrain the T-structure. Other compounds affecting the allosteric equilibrium include inositol hexaphosphate (1HP) and the fibric acid derivatives such as bezafibrate and clofibrate. The fibric acid derivatives, antilipidemic drugs, have been found to combine with deoxy-, but not with oxyhemoglobin. They stabilize the T-structure by combining with sites in the central cavity that are different from the DPG binding sites. Other allosteric effectors have been synthesized which are related to bezafibrate. A ligand that stabilizes specifically the R-structure increases the oxygen affinity, and a ligand that stabilizes the T-structure does the reverse. Other ligands may affect the spin state of the heme. For example, in deoxyhemoglobin and in methemoglobin the Fe is high-spin ferrous (S=2) and 5-coordinated; in oxyhemoglobin and in cyan-metHb the Fe is low-spin ferrous (S=0) and 6-coordinated; when $H_2O$ is the sixth ligand, methemoglobin is also high-spin. The inhibition of platelet aggregation by S-nitrosomethemoglobin seen in FIG. 7C is consistent with enhanced potency in the high spin conformation. Such substances which control the allosteric equilibrium or spin state of hemoglobin may be administered to a human or animal to promote the formation of, or to stabilize, a particular allosteric structure and/or spin state.

The dosage of Hb required to deliver NO for the purpose of platelet inhibition can be titrated to provide effective amounts of NO without causing drastic changes in blood pressure. If the goal of the therapy is to deliver oxygen, the Hb may be administered in a unit of blood to avoid a drop in blood pressure. If the goal is to alleviate shock, very little Hb can be administered compared to the amount to be given for myocardial infarction. For shock, the more important goal is to deliver NO rather than to deliver oxygen. It may be preferable to use continuous infusion or several infusions per day. Example 12 (see FIG. 10) shows that the effects of SNO-Hb(FeII)$O_2$ on blood flow in rat brain last over 20 minutes; in other experiments an effect has been seen for up to an hour. There is a correlation between blood pressure effects and platelet inhibition effects, but platelet inhibition occurs at a lower NO concentration than that which is required to produce blood pressure effects, and generally lasts longer.

Example 11 shows that S-nitrosothiols can be used to add NO groups not only on the thiol groups of cysteine residues in hemoglobin, but also on other reactive sites of the hemoglobin molecule. The products of the nitrosation reactions in Example 11 were hemoglobin molecules with more than 2 NO groups per Hb tetramer. The exact sites of the addition of NO have not been confirmed, but it is expected that NO addition occurs at thiol groups and various other nucleophilic sites within Hb, including metals. Reactive sites, after the thiol groups, are tyrosine residues and amines, and other nucleophilic centers.

Nitrosation reactions on other proteins have been investigated previously (Simon, D. I. et al., *Proc. Natl. Acad. Sci. USA* 93:4736–4741 (1996)). Methods of modifying proteins to produce nitrosoproteins are known in the art, and include, for example, exposing the protein to $NaNO_2$ in 0.5 M HCl (acidified $NO_2^-$) for 15 minutes at 37° C. An alternative method is to place a helium-deoxygenated solution of protein in 100 mM sodium phosphate, pH 7.4, inside dialysis tubing and expose the protein to NO gas bubbled into the dialysate for 15 minutes. (Stamler, J. S. et al., *Proc. Natl. Acad. Sci. USA* 89:444–448 (1992); see also Williams, D. L. H. *Nitrosation*, Cambridge University Press, New York (1988), which gives further methods of nitrosation).

By these methods, multiple NO-related modifications ("NO groups" or "NO biological equivalents" resulting from nitrosations, nitrosylations or nitrations) can be made on Hb at nucleophilic sites, which may include thiols, nucleophilic oxygen atoms as may be found in alcohols, nucleophilic nitrogen atoms as may be found in amines, or the heme iron. Agents facilitating nitrosations, nitrosylations or nitrations of Hb can be thought of as "NO or $NO^+$ donating agents." The products of such modifications may have such groups, for example, as —SNO, —$SNO_2$, —ONO, $ONO_2$, —CNO, —$CNO_2$, —NNO, —$NNO_2$, —FeNO, —CuNO, —SCuNO, SFeNO and the different ionized forms and oxidation variants thereof. (See, regarding oxidation of hemoglobin by $Cu^{++}$, Winterbourne, C., *Biochemistry J.* 165:141–148 (1977)). The covalent attachment of the NO group to sulfydryl residues in proteins is defined as S-nitrosation; the covalent attachment of the NO group to a metal, such as Fe, can be called nitrosylation, yielding a metal-nitrosyl complex. General NO attachment to nucleophilic centers is referred to herein as nitrosation. Thus, the term nitrosated hemoglobin as used herein includes SNO-Hb and Hb(FeII) NO as well as other forms of hemoglobin nitrosated at other sites in addition to thiols and metals. In addition, Hb can be nitrated. Hbs which have been nitrosated and/or nitrated at multiple different types of nucleophilic sites (termed polynitrosated, that is, having NO equivalents added to other nucleophilic sites as well as to thiols; or polynitrated, respectively) will permit transnitrosation reactions and the release of NO and its biological equivalents in the circulatory system at different rates and engendering different potencies.

These and other nitrosation and nitration reactions can cause oxidation of the heme Fe to some extent, under some conditions. However, some minor degree of oxidation is acceptable. The nitrosated Hb is still be useful as a therapeutic agent if oxidized to a minor extent. For applications where the NO-delivering function, rather than the $O_2$-delivering function of nitrosated Hb, is more desirable, extensive oxidation of the heme Fe is acceptable.

If it is desired to avoid oxidation of the heme Fe, it is possible to remove the heme, perform the necessary chemical reactions upon the protein to nitrosate to the extent desired, and replace the heme into the modified hemoglobin product. (See, for removing and replacing the heme, Antonini, E. and Brunori, M., *Hemoglobin and Myoglobin in their Reactions with Ligands*, Elsevier, N.Y., 1971.)

In addition to the nitrosating under conditions that do not oxidize the heme, such as brief exposure to low molecular weight RSNOs, as illustrated in Examples 1 and 2, alternative methods can be used to produce nitrosated hemoglobin in which the heme Fe is not oxidized. For instance, it is possible to produce by recombinant methods α and β globin chains, nitrosate them to the extent desired, then assemble the chains with heme to form a functional, nitrosated tetramer. (See, for example, European Patent Application EPO 700997, published Mar. 13, 1996, filed May 10, 1990, "Production in bacteria and yeast of hemoglobin and analogues thereof.")

Another alternative method to nitrosate the α and β globin chains without producing a form of metHb as the end product, is to nitrosate the intact Hb molecule to the extent desired, thereby allowing the heme Fe to be oxidized, then reduce the heme Fe by treating the nitrosated Hb with either methemoglobin reductase or a cyanoborohydride such as sodium cyanoborhydride.

It has been generally thought that nitric oxide as NO gas in solution reacts with hemoglobin (Hb) in two major ways: 1) with the deoxyHb to form a stable nitrosyl (FeII) heme adduct; and 2) with oxyHb to form nitrate and metHb—a reaction that inactivates NO. These two reactions contributed to the idea that Hb is a scavenger of NO. In both of these reactions, NO biological activity is lost. The results described herein demonstrate that, in fact, neither reaction occurs under physiological conditions. Rather, the products of the NO/Hb reaction are dictated by the ratio of NO to Hb, and by the conformation of Hb—R(oxy) vs. T(deoxy).

At low ratios of NO to deoxyHb (e.g., 1:100 or less), the Hb molecule is in T-structure. Under this condition, NO introduced as gas to a Hb solution binds to the α-hemes, as has been seen by EPR. Upon introduction of oxygen, with conversion to the R state, NO is transferred to a thiol of cysteine to yield S-nitrosohemoglobin with close to 100% efficiency. At ratios of NO/Hb of 1:25–1:50, the efficiency of formation of SNO-Hb is ~35% (decreasing with increasing NO/Hb ratio). The reaction appears to involve migration of NO from a heme to P heme and then to the β thiol. In going from the heme to a thiol, the heme or nitrosothiol needs to lose an electron by oxidation (NO→$NO^+$ or RSNO·→RSNO). Oxygen serves as an electron acceptor in the system, driving the reaction thermodynamically, as well as causing a conformational change by its binding at the heme, which exposes the thiol groups. At higher ratios of NO to Hb (1:20–1:2), with the protein still in T-structure, we find that the protein liberates $NO^-$ from the β hemes with production of metHb. This occurs in the absence of $O_2$ and provides another indication that the NO bound to β-hemes is unstable. Once $O_2$ is introduced, S-nitrosothiol (SNO) may form, but the relative yield is very low because of loss to $NO^-$. The yield of SNO-Hb approaches zero at NO/Hb ratios of 1:2, upon introduction of oxygen.

At the higher ratios of NO to Hb (i.e., >0.75–1), NO itself maintains the R-structure. Under this condition, the NO is more stable because of an unusual constraint on the molecule. Specifically, loss of NO from the β hemes promotes the T-structure, whereas formation of SNO-Hb selects for the R-structure. This is not a favored reaction. The consequence is that small amounts of S-nitrosohemoglobin are formed, but the yields are low (~5%). This does not exclude the possibility that the molecule has therapeutic value, but would give the appearance of a very stable compound with no biological effect.

The reaction of NO with oxyHb is also dependent on the ratios of NO to oxyHb. Under conditions of relatively high (non-physiological) ratios of NO to Hb, (NO/oxyHb>1:20), NO appears to destabilize the hydrogen bond between the $O_2$ and the proximal histidine (by competing for it) yielding some metHb. By changing the ionic composition of the solvent buffer (e.g., borate 0.2 M, pH 7.4), formation of metHb can be significantly reduced even with excess NO (NO/Hb=3:1). On the other hand, metHb formation is facilitated in acetate buffer at pH 7.4; when the hydrogen bond between $O_2$ and the proximal histidine is broken, the $O_2$ seems to gain superoxide-like character. NO then reacts rapidly to form metHb and nitrate. Efficient metHb formation actually requires an excess of NO/oxyHb. In contrast, at lower ratios of NO/Hb (<1:20), it reacts with the small residual fraction (<1%) of deoxyHb, in turn producing S-nitroso-hemoglobin extremely efficiently. As the concentration of NO is increased, there is some reaction with oxyHb, but the products are nitrite and nitrate, not nitrate alone. The conclusion is that NO can be incubated in reaction mixtures of oxyHb without inactivating the $O_2$ binding functionality by converting it to nitrate.

Nitrosylhemoglobin can be used in an animal or human as a therapeutic NO donor for the prevention or treatment of diseases or medical disorders which can be alleviated by delivery of NO or its biologically active form to tissues affected by the disease or medical disorder. Like SNO-Hb, nitrosylhemoglobin can be administered as a blood substitute, because nitrosylhemoglobin can be converted to SNO-Hb under physiological conditions. NO is released from the thiol either by deoxygenation or by conversion to metHb.

Inhaled NO causes selective pulmonary vasodilation without influencing systemic responses. A previously-formed rationale behind its use is that scavenging by Hb prevents adverse systemic effects. It is illustrated in Examples 14–21 that NO can be used to produce S-nitrosohemoglobin, which is a potent vasodilator and antiplatelet agent. Inhaled NO can be used to raise levels of endogenous S-nitrosohemoglobin. Similarly, treatment of red blood cells (RBCs) with NO can be used to form SNO-RBCs, or "loaded" red blood cells.

Compared to SNO-deoxyHb, which is a good NO donor, but which would release its NO very quickly, or SNO-oxyHb, which would release its NO more slowly, but has a propensity to form metHb over time, nitrosyl-deoxyhemoglobin stored in a form such that final ratio of NO:heme is less than about 1:100 or greater than about 0.75, is stable. Formation of metHb is prevented at these NO:heme ratios. For this reason nitrosyl-deoxyhemoglobin stored with such NO:heme ratios in a physiologically compatible buffer can be administered to an animal or human as an NO donor.

A blood substitute or therapeutic which can be used as an NO donor, and which is free of the vasoconstrictor effects of underivatized Hbs, can be made by obtaining a solution of oxyHb (including solutions stored in the form of oxyHb) and adding NO as dissolved gas, yielding SNO-oxyHb. Buffer conditions and NO:Hb ratios can be optimized, as illustrated in Example 21 and FIG. 19, to yield S-nitrosothiol without significant production of oxidized Hb (metHb). For example, NO added to oxyhemoglobin in 10 mM phosphate buffer, pH 7.4, at a ratio of less than 1:30 NO:Hb resulted in formation of SNO-oxyHb with minimal formation of metHb. This ratio can be increased by varying the buffer conditions, for example by the use of 10 mM phosphate, 200 mM borate at pH 7.4. The buffer anions as well as the buffer concentration should be chosen carefully. For instance, acetate and chloride have the opposite effect from borate, increasing the formation of metHb and nitrite at 200 mM, pH 7.4.

This may be explained by a competition between free NO and oxygen for a H-bond with the imidazole of the proximal His residue. If low concentrations of NO are used, in low ionic strength buffer, e.g., 10 mM phosphate, metHb does not readily form. If the H-bond is weakened by increasing the ionic strength of the buffer, NO reacts more readily with oxyHb, yielding more metHb. Buffers with a low $PK_a$ relative to pH 7.4 tend to stabilize FeIII. Buffers having a $pK_a$ at least about two pH units higher than the reaction condition are preferred.

A blood substitute can be made which acts as a donor of $NO^-$. NO can be added to a solution of deoxyHb at a ratio of NO:Hb in the range of 1:100 to 1:2, with a ratio of NO/heme of approximately 1:10 being preferred. If the ratio of NO:heme is increased, to a NO:Hb of about 2 (at which Hb is still in the T (deoxy) state), in the absence of an electron acceptor/free radical scavenger, NO is released from the β heme as NO⁻, with oxidation of the heme iron to form metHb. The product solution can be used as a blood substitute or a therapeutic NO donor. NO⁻ can protect from N-methyl-D-glutamate-mediated brain injury in stroke; this effect has not been found for NO.

Nitosylhemoglobin belongs to a broader class of nitrosyl-heme-containing donors of NO which can be administered to an animal or human for the delivery of NO to tissues. Nitrosyl-heme-containing donors of NO include, for example, the nitrosated ("nitrosated" as defined herein) hemoglobins nitrosylhemoglobin and SNO-nitrosylhemogobin, nitrosyl-heme, and substituted forms of hemoglobin in which a different metal, (e.g., Co$^{++}$, Mg$^{++}$, Cu$^{++}$) is substituted for the heme iron, or nitrosyl-porphyrins are substituted for the heme.

Applicants teach physiologically significant results that provide a rationale for NO donors to be attached to Hb. Such derivatized Hbs can themselves serve as NO-donating therapeutics and can ameliorate the side effects of underivatized Hb administered as a blood substitute, for example. At one time, it had been thought that there would be no use for these compounds, because it was thought that NO released by the Hb would immediately be scavenged by the heme. It had been thought also that the released NO would oxidize Hb and limit oxygen delivery. The same rationale has previously limited the administration of NO donors, such as nitroglycerin and nitroprusside, because they had been thought to cause the formation of metHb.

Preferably, NO-donors to be covalently attached to hemoglobin are relatively long-lived and have at least one functional group that can be used for the chemical attachment to hemoglobin. Examples of NO-donors include nitroprusside, nitroglycerin, nitrosothiols, and the diazeniumdiolte class of compounds (also called "NONOates") having structure 1.

| X = [B(O)NO]⁻ → X⁻ + 2NO | (at pH 7.4, 37°) |
|---|---|
| 1 | (X = a nucleophilic residue) |
| a diazeniumdiolate | |

A variety of these compounds have been synthesized that, in their anionic form, release NO without activation at physiological pH (Keefer, L. K. et al., *Am. Chem. Soc. Symposium Ser.* 553:136–146 (1994); Hanson, S. R. et al., *Adv. Pharmacol.* 34:383–398 (1995)). Systemic administration can result in system-wide effects, according to equation 1. However, attachment to hemoglobin can be used to produce tissue-selective delivery of NO and oxygen. For instance, covalently esterifed NO-donors can be activated predominantly in the liver. Different NO donors can be chosen to be linked to hemoglobin for different controlled release rates of NO from Hb.

Compound 4, for example, is a diazeniumdiolate with a half-life for NO release, at 37° C. and pH 7.4, of approximately two weeks. It can be converted to its nucleophilic N-4 mercaptoethyl derivative, compound 5. Hemoglobin can be activated toward coupling reactions by reacting it with γ-maleimidobutyric acid N-hydroxysuccinimide ester. Compound 5 can then be covalently attached to the activated hemoglobin through its maleimide functionality. The adduct, 6, can generate NO steadily over several days in pH 7.4 phosphate buffer at 37° C. This would alleviate side effects of underivatized blood substitutes, for example.

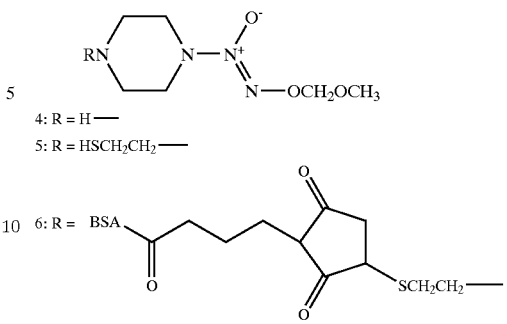

4: R = H—
5: R = HSCH₂CH₂—

6: R = BSA

Nitric oxide synthase (NOS) conjugated to Hb can reload NO onto the hemes, facilitating delivery of NO to the tissues. NOS of neurons is preferable for this conjugated Hb because the neuronal NOS responds to oxygen tension. At low oxygen tension, the neuronal NOS produces more NO; at high oxygen tension, NOS produces less NO. This form of NOS will efficiently reload NO onto the heme when Hb is deoxygenated. NOS-Hb conjugates can be used when a blood substitute is indicated, and especially when an ischemic injury or condition is present.

Biologically compatible electron acceptors, are well known in the art and include, but are not limited to, superoxide dismutase and the oxidized forms of nicotinamide adenine dinucleotide (NAD⁺), nicotinamide adenine dinucleotide phosphate (NADP⁺), flavin adenine dinucleotide (FAD), flavin mononucleotide (FMN), ascorbate, dehydroascorbate and nitroxide spin traps. One or more electron acceptors can be conjugated to Hb molecules, and can facilitate the conversion of the nitrosyl-Hb-electron acceptor form to the SNO-Hb-electron acceptor form by accepting the electron lost by NO in its transfer, in the form of NO⁺ or as RSNO·, to a β93Cys thiol group.

Nitroxides are one such class of electron acceptors which also act as free radical scavengers. Nitroxides are stable free radicals that have been shown to have antioxidant catalytic activities which mimic those of superoxide dismutase (SOD), and which when existing in vivo, can interact with other substances to perform catalase-mimic activity. Nitroxides have been covalently attached to hemoglobin. See Hsia, J-C., U.S. Pat. No. 5,591,710, the contents of which are incorporated by reference in their entirety. See also Liebmann, J. et al., *Life Sci.* 54:503–509 (1994), describing nitroxide-conjugated bovine serum albumin and differential nitroxide concentrations among the different organs of mice tested with the conjugate.

Methods for chemically attaching superoxide dismutase (SOD) to Hb are known in the art. For example, see Quebec, E. A. and T. M. Chang, *Artif. Cells Blood Substit. Immobil. Biotechnol.* 23:693–705 (1995) and D'Agnillo, F. and Chang, T. M., *Biomater. Artif. Cells Immobilization Biotechnol.* 21:609–621 (1993). SOD attached to nitrosylhemoglobin can drive the reaction in which NO is transfered from the heme to thiol, by serving as an electron acceptor.

Like NO, CO is known to have vasodilator effects. (See Zakhary, R. et al., *Proc. Natl. Acad. Sci USA* 93:795–798 (1996).) A solution of deoxyhemoglobin can be derivatized with CO by exposing it to purified CO gas in solution, until the desired extent of CO-bound Hb is reached. CO-derivatized Hb can be administered as a blood substitute or co-administered with other heme-based blood substitutes to alleviate the effects (e.g., hypertension, intestinal pain and immobility) of underivatized hemoglobin. Hemoglobins can be derivatized to the extent necessary to overcome constrictor effects, for example to a ratio of CO/Hb in the range of approximately 0.1% to 10.

Because the α subunits lack thiol groups to serve as NO+ acceptors from the heme, a blood substitute comprising α chains, for example in the form of dimers or tetramers, can be made which has different properties from a blood substitute comprising β chains alone, or comprising a combination of α and β chains. A blood substitute comprising α chains of hemoglobin can be administered to an animal or to a human patient to alleviate a condition characterized by the effects caused by NO, for example, in hypotensive shock.

β chains, unlike α chains, serve as active donors of NO to the tissues, rather than traps for NO. A blood substitute comprising β chains, for example in the form of β dimers or tetramers, can be made. Such a blood substitute can be used in conditions where it is desired to deliver oxygen as well as NO to tissues, for example, in angina and other ischemic conditions.

Methods are known by which hemoglobin can be separated into its α and β subunits and reconstituted. Separated, heme-free, alpha- and beta-globins have been prepared from the heme-containing alpha and beta subunits of hemoglobin. (Yip, Y. K. et al., *J. Biol. Chem.* 247:7237–7244 (1972)). Native human hemoglobin has been fully reconstituted from separated heme-free alpha and beta globin and from hemin. Preferably, heme is first added to the alpha-globin subunit. The heme-bound alpha globin is them complexed to the heme-free beta subunit. Finally, heme is added to the half-filled globin dimer, and tetrameric hemoglobin is obtained (Yip, Y. K. et al., *Proc. Natl. Acad. Sci. USA* 74:64–68 (1997)).

The human alpha and beta globin genes reside on chromosomes 16 and 11, respectively. Both genes have been cloned and sequenced, (Liebhaber, et al., *Proc. Natl. Acad. Sci. USA* 77:7054–7058 (1980) (alpha-globin genomic DNA); Marotta, et al., J. Biol. Chem. 252:5040–5053 (1977) (beta globin cDNA); Lawn, et al., *Cell* 21:647 (1980) (beta globin genomic DNA)).

Recombinant methods are available for the production of separate α and β subunits of hemoglobin. Nagai and Thorgerson, (*Nature* 309:810–812 (1984)) expressed in *E. coli* a hybrid protein consisting of the 31 amino terminal residues of the lambda cII protein, an Ile-Glu-Gly-Arg linker, and the complete human beta globin chain. They cleaved the hybrid immediately after the linker with blood coagulation factor Xa, thus liberating the beta-globin chain. Later, (Nagai, K. et al., *Proc. Natl. Acad. Sci. USA* 82:7252–7255 (1985)) took the recombinant DNA-derived human beta globin, naturally derived human alpha globin, and a source of heme and succeeded in producing active human hemoglobin.

An efficient bacterial expression system for human alpha globin was reported. (GB 8711614, filed May 16, 1987; see also WO 88/09179). This led to the production of wholly synthetic human hemoglobin by separate expression of the insoluble globin subunits in separate bacterial cell lines, and in situ refolding of the chains in the presence of oxidized heme cofactor to obtain tetrameric hemoglobin. A synthetic human hemoglobin has been produced in yeast cells (EP 700997A1, filing date 10.05.1990).

The properties of hemoglobin have been altered by specifically chemically crosslinking the alpha chains between the Lys99 of alpha 1 and the Lys99 of alpha 2. (Walder, U.S. Pat. Nos. 4,600,531 and 4,598,064; Snyder, et al., *Proc. Natl. Acad. Sci USA* 84:84 7280–7284 (1987); Chaterjee, et al., *J. Biol. Chem.* 261:9927–9937 (1986)). This chemical crosslinking was accomplished by reacting bis (3,5-dibromosalicyl) fumarate with deoxyhemoglobin A in the presence of inositol hexaphosphate. The beta chains have also been chemically crosslinked. (Kavanaugh, M. P. et al., *Biochemistry* 27:1804–1808 (1988)). These linking methods can be adapted to methods of producing α or β dimers or other multimers, or for the crosslinking of other polypeptides to the α and β chains. (For further methods to derivatize proteins and to conjugate proteins, see Hermansoh, G. T., *Bioconjugate Techniques*, Academic Press, 1996.)

The term hemoglobin or Hb as used herein includes variant forms such as mutant forms, chemically modified forms, genetically altered forms, such as fusion proteins, and truncated forms. It also includes Hbs of all animal species and variant forms thereof. The biological and/or chemical properties of these variant Hbs may be different from those of hemoglobins which are found naturally occurring in animals.

It will be appreciated that NO exists in biological systems not only as nitric oxide gas, but also in various redox forms and as biologically active adducts of nitric oxide such as S-nitrosothiols, which can include S-nitrosoproteins, S-nitroso-amino acids and other S-nitrosothiols (Stamler, J. S. *Cell* 78:931–936 (1994)).

A blood substitute can be a biologically compatible liquid which performs one or more functions of naturally occurring blood found in a mammal, such as oxygen carrying and/or delivery, NO carrying and/or delivery, and the scavenging of free radicals. A blood substitute can also comprise one or more components of such a liquid which, when infused into a mammal, perform one or more functions of naturally occurring blood. Examples of blood substitutes include preparations of various forms of hemoglobin. Such preparations may also include other biologically active components, such as a low molecular weight thiol, nitrosothiol or NO donating agents, to allow transnitrosation.

The compounds and therapeutic preparations of this invention to be used in medical treatment are intended to be used in therapeutically effective amounts, in suitable compositions, which can be determined by one of skill in the art. Modes of administration are those known in the art which are most suitable to the affected site or system of the medical disorder. Intravenous infusion is a preferred mode of administration of various forms of hemoglobin to be used as a blood substitute. Suitable compositions may include carriers, stabilizers or inert ingredients known to those of skill in the art, along with biologically active component(s).

The term "therapeutically effective amount," for the purposes of the invention, refers to the amount of nitrosated Hb and/or nitrosating agent which is effective to achieve its intended purpose. While individual needs vary, determination of optimal ranges for effective amounts of each compound to be administered is within the skill of one in the art. Research animals such as dogs, baboons or rats can be used to determine dosages. Generally, dosages required to provide effective amounts of the composition or preparation, and which can be adjusted by one of ordinary skill in the art, will vary, depending on the age, health, physical condition, sex, weight, extent of disease of the recipient, frequency of treatment and the nature and scope of the desired effect. Dosages for a particular patient can be determined by one of ordinary skill in the art using conventional considerations, (e.g. by means of an appropriate, conventional pharmacological protocol). For example, dose response experiments for determining an appropriate dose of a heme-based blood substitute can be performed to determine dosages necessary to produce a physiological concentration of approximately 1 nM to 100 μM heme. Suitable pharmaceutical carriers can be combined with active ingredients employed in a therapeutic composition, if necessary.

The present invention is further and more specifically illustrated in the following examples, which are not intended to be limiting in any way.

Exemplification

Materials and Methods for Assays

Determination of R—S—NO Concentration

The concentration of R—S—NO groups in a sample is based on the method reported in Saville, *Analyst* 83:670–672 (1958). The quantification of the NO group, displaced from the thiol by mercuric ion, forms the basis of this highly sensitive method. The detection limit is in the range of 0.1–0.5 μM.

  (5)

  (6)

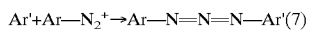 (7)

As shown (equations 5–7), the reaction proceeds in two steps. First, $NO^+$ is displaced from the RSNO by mercuric ion and reacts, under acidic conditions, with sulfanilamide (Ar—$NH_2$). In a second step, the diazonium salt (which is formed in amounts equivalent to the thionitrite) is then coupled with the aromatic amine, N-(1-naphthyl)-ethylenediamine (Ar'), to form an intensely colored azo dye which can be measured at 540 nm ($\epsilon \sim 50,000$ $M^{-1}$ $cm^{-1}$). The same assay performed with the mercuric salt omitted allows for the simultaneous detection of nitrite. In principle, the second part of the Saville procedure is analogous to the classical Griess reaction for the detection of nitrite.

The procedure is as follows:

Solution A: sulfanilamide 1t dissolved in 0.5 M HCl.
Solution B: same solution as used in A to which 0.2% $HgCl_2$
Solution C: 0.02% solution of N-(1-naphthyl)-ethylenediamine dihydrochloride dissolved in 0.5 M HCl.

A given volume (50 μl–1 ml) of the sample to be assayed is added to an equivalent volume of solution A and solution B. The two samples are set aside for 5 minutes to allow formation of the diazonium salt, after which an equivalent volume of solution C is added to each mixture. Color formation, indicative of the azo dye product, is usually complete by 5 minutes. The sample absorbance is then read spectrophotometrically at 540 nm. The RSNO is quantified as the difference in absorbance between solution B and A. (i.e. B–A). In the event that the background nitrite concentration is high (i.e. increased background in A), the accuracy of the measurement can be increased by the addition of an equivalent volume of 0.5% ammonium sulfamate in acid (45 mM) 5 minutes prior to the addition of sulfanilamide. The nitrous acid in solution reacts immediately with excess ammonium sulfamate to form nitrogen gas and sulfate.

Concentrations of thiol greater than 500 μM in samples may interfere with the assay if nitrite is also present at micromolar concentration. Because nitrite will nitrosate indiscriminantly under the acidic conditions employed, thiols will effectively compete for reaction with sulfanilamide (present at 50 mM in this assay) as their concentration approaches the millimolar range. This will lead to artifactual detection of RSNO. The problem can be avoided by (1) keeping the ratio of thiol to sulfanilamide <0.01, (2) first alkylating thiols in the solution, or (3) adding free thiols to standards to correct for the potential artifact.

Assay for S-nitrosohemoglobin and Nitrosyl(FeII)-Hemoglobin

A highly sensitive photolysis-chemiluminescence methodology was employed, which had been used for measuring RSNOs (S-nitrosothiols) in biological systems (Gaston, B., et al., *Proc. Natl. Acad. Sci. USA* 90:10957–10961 (1993); Stamler, J. S., et al., *Proc. Natl. Acad. Sci USA* 89:7674–7677 (1992)). The method involves photolytic liberation of NO from the thiol, which is then detected in a chemiluminesence spectrometer by reaction with ozone. The same principle of operation can be used to cleave (and measure) NO from nitrosyl-metal compounds (Antonini, E. and Brunori, M. In *Hemoglobin and Myoglobin in Their Reactions with Ligands*, American Elsevier Publishing Co., Inc., New York, pp. 29–31 (1971)). With adjustment of flow rates in the photolysis cell, complete photolysis of the NO ligand of Hb(FeII)NO is achieved. Standard curves derived from synthetic preparations of SNO-Hb, Hb(FeII)NO, and S-nitrosoglutathione were linear (R>0.99), virtually superimposable, and revealing of sensitivity limits of approximately 1 nM. Two analytical criteria were then found to reliably distinguish SNO-Hb from Hb(FeII)NO: 1) signals from SNO-Hb were eliminated by pretreatment of samples with 10-fold excess $HgCl_2$, while Hb(FeII)NO was resistant to mercury challenge; and 2) treatment of SNO-Hb with $HgCl_2$ produced nitrite (by standard Griess reactions) in quantitative yields, whereas similar treatment of Hb(FeII)NO did not. UV/VIS spectroscopy confirmed that NO remained attached to heme in the presence of excess $HgCl_2$.

We linked a photolysis cell directly to the reaction chamber and detector portion (bypassing the pyrolyzer) of a chemiluminescence apparatus (model 543 thermal energy analyzer, Thermedix, Woburn Mass.). A sample (5 to 100 μl) is either introduced directly or introduced as a chromatographic effluent from an attached high-performance liquid or gas chromatography system into the photolysis cell (Nitrolite, Thermedix, Woburn Mass.). This cell consists of a borosilicate glass coil (3 m×0.64 cm o.d.×1 mm i.d., turned to a diameter of 6 cm and a width of 12 cm). The sample is introduced with a purge stream of helium (5 liters/min) and then irradiated with a 200-W mercury-vapor lamp (vertically mounted in the center of the photolysis coil on Telfon towers). The effluent from the photolysis coil is directed to a series of cold traps, where liquid and gaseous fractions less volatile than nitric oxide (such as nitrite and nitrate) are removed. Nitric oxide is then carried by the helium stream into the chemiluminescence spectrometer, in which free nitric oxide is detected by reaction with ozone. Signals are recorded on a digital integrator (model 3393A, Hewlett-Packard). Flow rates and illumination levels in the photolysis cell were designed to result in complete photolysis of the S—N bond of S-nitrosothiols, as confirmed by analysis of effluent from the cell according to the method of Saville (Saville, B., *Analyst* 83:670–672 (1958)).

To determine what fraction of the total nitric oxide detected in samples was derived from S-nitrosothiols, several control measurements were performed. Mercuric ion was used to displace nitric oxide selectively from the S-nitrosothiols (Saville, B., *Analyst* 83:670–672 (1958)). Comparison of measured nitric oxide concentrations from samples alternatively pretreated or not pretreated with $HgCl_2$ ensured that nitric oxide obtained by photolysis was derived specifically from S-nitrosothiols. Similarly, as an added measure of confirmation, we distinguished between S-nitrosothiols and free nitric oxide by comparing nitric oxide concentrations in samples alternatively exposed or not exposed to photolyzing illumination.

Methods for Spectrophotometric Experiments and Nitrosylhemoblogin Formation, Examples 14–20

Purified human $HbA_0$ was obtained from Apex Biosciences (Antonini, E. and Brunori, M. In *Hemoglobin and Myoglobin in Their Reactions with Ligands*, American Elsevier Publishing Co., Inc., New York (1971)). The spectrophotometer used was a Perkin Elmer UV/vis Spectrometer Lambda 2S. All measurements were made at 23° C. in a sealed quartz cuvette to which all additions were made. Deoxygenation was achieved by argon passage through a Hb solution within a sealed quartz cuvette. The degree of deoxygenation can be measured by UV/vis spectrum. Nitrosylation of hemes is achieved by addition of purified NO gas to deoxyHb and the products quantitated by the extinction coefficient per Antonini and Brunori, supra.

EXAMPLE 1

Interactions of NO and RSNO with Hb

It was observed that naturally occurring N-oxides, such as NO and RSNOs (Gaston, B., et al., *Proc. Natl. Acad. Sci. USA* 90:10957–10961 (1993); Scharfstein, J. S., et al., *J. Clin. Invest.*, 94:1432–1439 (1994); Clancy, R. M., et al., *Proc. Natl. Acad. Sci USA*, 91:3680–3684 (1994)), differed markedly in their reactions with Hb. NO bound very rapidly to deoxyHb (Hb[FeII]), forming relatively stable Hb[FeII] NO complexes (FIG. 1A), and converted oxyHb (Hb[FeII] $O_2$) to methemoglobin (Hb[FeIII]) and nitrate (FIG. 1B), confirming previous reports (Olson, J. S., *Meth. Enzymol.* 76:631–651 (1981); Toothill, C., Brit. J. *Anaesthy.* 39:405–412 (1967)). In contrast, RSNOs were found to participate in transnitrosation reactions with sulfhydryl groups of Hb, forming S-nitrosohemoglobin (SNO-Hb), and did not react with the heme centers of either deoxyHb or $Hb(FeII)O_2$ (FIGS. 1C and 1D).

A. Interaction of NO with deoxyHb

Conversion of deoxyHb (Hb[FeII]) to Hb(FeII)NO is observed upon incubation of Hb(FeII) with increasing concentrations of nitric oxide. See FIG. 1A. a. Deoxy Hb. b, c, d. Reaction mixtures of NO and Hb(FeII) in ratios of 1:1, 2:1 and 10:1, respectively. The reaction product Hb(FeII)NO formed essentially instantaneously on addition of NO (i.e. within instrument dead time).

B. Interaction of NO with OxyHb

Conversion of oxyHb (HbFeII]$O_2$) to metHb (HbFe[III]) is observed upon incubation of oxyHb with increasing concentrations of NO. See FIG. 1B. a. oxy Hb. b, c, d. Reaction mixtures containing NO and oxyHb in ratios of 1:1, 2:1 and 10:1, respectively. Methemoglobin formation occurred instantaneously on addition of NO (i.e. within instrument dead time).

C. Interaction of S-Nitrosothiols with DeoxyHb

Conversion of Hb(FeII) to SNO-Hb(FeII) is observed upon incubation of either GSNO (shown) or S-nitrosocysteine (CYSNO) with deoxy Hb. There is little (if any) interaction of RSNO with the heme functionalities of Hb. See FIG. 1C. a. deoxyHb. b, c, d. Reaction mixtures of GSNO and Hb(FeII) in ratios of 1:1, 2:1 and 10:1, respectively. Spectra were taken after 60 min of incubation in b, c, and 15 min in d. Further analysis of reaction products revealed the formation of moderate amounts of SNO-Hb in all cases. Yields of SNO-Hb (S—NO/Hb) in b, c, and d at 60 min were 2.5%, 5% and 18.5%, respectively. (See FIG. 1C and FIG. 2A.)

D. Interaction of S-Nitrosothiols with OxyHb

Conversion of $Hb(FeII)O_2$ to $SNO-Hb(FeII)O_2$ is observed upon incubation of either GSNO (shown) or CYSNO with oxyHb. There is little (if any) reaction of GSNO (or CYSNO) at the heme centers of $Hb(FeII)O_2$. Specifically, the capacity for $O_2$ binding to heme is unaffected by RSNOs. See FIG. 1D. a. oxyHb. b, c, d. Reaction mixtures of GSNO and oxyHb in ratios of 1:1, 2:1, and 10:1, respectively. Spectra were taken after 60 min of incubation in the spectrophotometer. Further analysis of reaction products revealed the formation of SNO-Hb in all cases. Yields of SNO-Hb in spectra b, c and d were 5%, 10% and 50% (S-NO/Hb), respectively. In 5 other determinations, the yield of S-NO/Hb was 0.37±0.06 using GSNO (pH 7.4, 10-fold excess over Hb) and ~2 SNO/tetramer (1.97±0.06) using CYSNO (vida infra). These last data are in agreement with reports that human HbA contains 2 titratable SH groups.

Methods

Human $HbA_o$ was purified from red cells as previously described (Kilbourn, R. G., et al., *Biochem. Biophys. Res. Comm.*, 199:155–162 (1994)). Nitric oxide solutions were rigorously degassed and purified according to standard procedure (Beckman, J. S., et al., *Methods in Nitric Oxide Research*, Feelisch and Stamler, eds., Wiley Chichester, U. K. (1996)) and saturated solutions were transferred in air tight syringes. Deoxygenation of Hb was achieved by addition of excess dithionite (NO studies) or by reduction of $Hb(FeII)O_2$ through evacuation in Thunberg tubes (RSNO studies; as RSNOs react with dithionite). RSNOs were synthesized as previously described (Gaston, B., et al., (1993); Arnelle, D. R. and Stamler, J. S., *Arch. Biochem. Biophys.* 318:270–285 (1995)) Incubations with $HbA_0$ were made in phosphate buffer, pH 7.4, 0.5 mM EDTA. Quantifications of SNO-Hb were made according to the method of Saville (Gaston, B., et al., (1993); Stamler, J. S., et al., *Proc. Nat. Acad. Sci. USA*, 90:444–448 (1992)) after purification of protein with Sephadex G-25 columns. The Saville method, which assays free $NO_x$ in solution, involves a diazotization reaction with sulfanilamide and subsequent coupling with the chromophore N-(naphthyl) ethylenediamine. No low molecular weight S—NO complexes survived this purification and all activity was protein precipitable. The reactions and spectra were carried out using a Perkin Elmer UV/Vis Spectrometer, Lambda 2S.

EXAMPLE 2

Allosteric Function of $O_2$, in Regulation of Hb S-Nitrosylation

Oxygenation of Hb is associated with conformational changes that increase the reactivity of cysβ93 to alkylating reagents (Garel, C., et al.,*J. Biochem.*, 123:513–519 (1982); Jocelyn, P. C., *Biochemistry of the SH Group*, Academic Press, London, p.243 (1972); Craescu, C. T., et al.,*J. Biol. Chem.*, 261:14710–14716 (1986)). The physiological importance of this effect was not established. It was observed here that rates of S-nitrosation of Hb were markedly dependent on conformational state. In the oxy conformation (R state), S-nitrosation was more rapid than in the deoxy conformation (T state) (FIG. 2A). The rate of S-nitrosation was accelerated in both conformations by alkaline conditions (i.e., rate at pH 9.2>pH 7.4), which would tend to expose the cysβ93 that is otherwise screened from reaction by the C-terminal histidine 146β. The salt bridge (asp β94—his β146) tying down the histidine residue is loosened at high pH. These data suggest that the increase in thiol reactivity associated with the R state derives, at least in part, from improved NO access rather than a conformation-induced change in pK.

A. Oxygenation Accelerates S-Nitrosylation of Hb

Rates of Hb S-nitrosation by S-nitrosocysteine (CYSNO) are faster in the oxy conformation (Hb[FeII]$O_2$) than in the deoxy state (Hb[FeII]).

Methods

Incubations were performed using 10-fold excess CYSNO over protein (50 μM) in aerated 2% borate, 0.5 mM EDTA (oxyHb), or in a tonometer after rapid $O_2$ evacuation (deoxyHb). At times shown in FIG. 2A, samples were rapidly desalted across G-25 columns (preequilibrated with phosphate buffered saline, 0.5 mM EDTA, pH 7.4) to remove CYSNO, and analyzed for SNO-Hb by the method of Saville (Stamler, J. S., et al., *Proc. Natl. Acad. Sci. USA*, 89:444–448 (1992)).

B. Deoxygenation Accelerates Denitrosylation of Hb

Rates of RSNO decomposition (and transfer) are much faster in the deoxy conformation [SNO-Hb(FeII)] than in the oxy state [SNO-Hb(FeII)$O_2$]. The decomposition of SNO-Hb(FeII) is further accelerated by the presence of excess glutathione. Within the dead time of measurements according to this method (~15 seconds), a major fraction of SNO-Hb(FeII) was converted to GSNO.

Methods

Hbs in PBS (0.5 mM EDTA, pH 7.4) were incubated in air (oxy) or in a tonometer previously evacuated of $O_2$ (deoxy) SNO-Hb(FeII)$O_2$ decomposition was determined by the method of Saville (Saville, B., *Analyst* 83:670–672 (1958)). Spontaneous decomposition of SNO-Hb(FeII) was followed spectrophotometrically by formation of Hb(FeII)NO. Transnitrosation reactions with glutathione were performed by addition of 100-fold excess glutathione over protein (50 μM), immediate processing of the reaction mixture under anaerobic conditions followed by rapid TCA precipitation, and analysis of RSNO in the supernatant. Rates of NO group transfer were too rapid to measure accurately by the standard methods used in this study.

EXAMPLE 3

NO-related Interactions with Cysteine Residues of Hb in Physiological Systems

Given that Hb is largely contained within red blood cells, potential mechanisms by which S-nitrosation of intracellular protein might occur were explored. Incubation of oxygenated rat red blood cells with S-nitrosocysteine resulted in very rapid formation of intracellular SNO-Hb(FeII)$O_2$ (FIG. 3A). Rapid oxidation of Hb was not observed under these conditions. Intraerythrocytic SNO-Hb also formed when red blood cells were treated with S-nitrosohomocysteine or S-nitrosocysteinylglycine, but not with S-nitrosoglutathione (GSNO). Thus, erythrocyte access of RSNOs is thiol group specific. Exposure of oxygenated red blood cells to NO resulted primarily in metHb formation.

Endothelium-Derived Relaxing Factor (EDRF) and Hemoglobin

Hb-mediated inhibition of endothelium-dependent relaxations is commonly used as a marker of NO responses. Inasmuch as reactions with either metal or thiol centers of Hb should lead to attenuated NO/EDRF (endothelium-derived relaxing factor) responses, experiments were performed to elucidate the molecular basis of inhibition. Hb preparations in which β93 thiol groups had been blocked with N-ethylmaleimide (NEM) or the hemes blocked by cyanmet (FeIIICN)-derivitization were studied in an aortic ring bioassay, and their activities were compared with that of native Hb. Both cyanmet-Hb and NEM-Hb caused increases in vessel tone and attenuated acetylcholine (EDRF)-mediated relaxations (FIG. 3B). However, native Hb was significantly more effective than either of the modified Hb preparations (FIG. 3B). Taken in aggregate, these studies suggest that both the thiol and metal groups of Hb contribute to its NO-related activity. To verify formation of an S-nitrosothiol in Hb, a bioassay was used in which 2 cm segments of thoracic aorta were interposed in Tygon tubing, through which 3 cc of Krebs solution containing Hb (4 μM) and ACh (2 μM) were circulated by roller pump (1.5 cc/min×5 min). Analysis of the effluent (Gaston, B., et al., (1993)) revealed the formation of SNO-Hb (20±4 nM) in 5 of 5 experiments.

A. S-Nitrosation of Intraerythrocytic Hb

Incubation of rat erythrocytes with S-nitrosocysteine (equimolar to heme (5 mM); phosphate buffer pH 7.4, 25° C.) leads to rapid formation of intracellular SNO-Hb(FeII) $O_2$,' MetHb does not form rapidly. Separation of intracellular RSNOs across G-25 columns reveals that only a small percentage exists as low molecular weight S-nitrosothiol (e.g. GSNO) at most time points. By 60 min, 3 of the 4 available SH groups of Hb were S-nitrosated (note that rat Hb contains 4 reactive SH groups). See FIG. 3A. Inset shows spectra of SNO-Hb isolated from rat erythrocytes and related analyses. Spectrum A is that of SNO-Hb isolated from erythrocytes following G-25 chromatography. Treatment of A with dithionite results in reduction of the S—NO moiety, liberating free NO which is autocaptured by deoxy Hb, forming Hb(FeII)NO (note that dithionite simultaneously deoxygenates Hb) (spectrum C). This spectrum (C) reveals a stoichiometry of ~3 S-NOs per tetramer. The spectrum of Hb(FeII)NO containing 4 NO's per tetramer is shown for comparison (inset, spectrum B).

Methods

At shown intervals, red blood cells were pelleted rapidly by centrifugation, washed three times, lysed in deionized water at 4° C., and the cytosolic fraction subjected to rapid desalting across G-25 columns. Intracellular SNO-Hb was measured by the method of Saville (Gaston, B., et al., (1992); Stamler, J. S., et al., *Proc. Natl. Acad. Sci. USA*, 89:444–448 (1992)), and confirmed spectroscopically (inset of FIG. 3A) as described above.

B. Molecular Basis of EDRF/Hb Interaction

The effects of native Hb on EDRF responses were compared with Hb preparations in which the thiol or heme centers had been blocked by alkylation or cyanmet derivitization, respectively. All preparations of Hb elicited contractions; however, those of native Hb (in which both SH and metal centers are free for interaction) were most pronounced. See FIG. 3B. Likewise, acetylcholine (ACh) mediated relaxations were most effectively inhibited by native Hb. Relaxations were inhibited to lesser degrees by cyanmet Hb (CN-Hb)(in which hemes were blocked from reaction) and NEM-Hb (in which thiol groups were alkylated by N-ethylmaleimide). See Table 1. These data illustrate that both heme and β93SH groups of Hb contribute to reversal of EDRF responses. Direct measurement of SNO-Hb, formed from EDRF under similar conditions, is described in Example 8.

Methods

Descending rabbit thoracic aorta were cut into 3 mm rings and mounted on stirrups attached to force transducers (model FT03, Grass Instruments, Quincy, Mass.) for measurement of isometric tone. The details of this bioassay system have been previously described (Stamler, J. S., et al., *Proc. Natl. Acad. Sci. USA*, 89:444–448 (1992)). Cyanmet Hb was prepared from human HbA according to published protocols (Kilbourn, R. G. et al. *Biochem. Biophys. Res. Comm.*, 199:155–162, (1994)). Alkylation of HbA with N-ethylmaleimide was followed by desalting across G-25 Sephadex to remove excess NEM. Removal of unmodified Hbcysβ93 was achieved by passage through Hg-containing affinity columns. The alkylation of free SH groups was verified using 5,5'-dithio-bis[2-nitrobenzoic acid].

TABLE 1

| ADDITIONS | % INCREASE IN TENSION (↓) | % ACh RELAXATION (†) |
|---|---|---|
| Hb (1 µM) | 40.8 ± 2.3 (n = 7) | 31.9 ± 6.9 (n = 7) |
| NEM-Hb (1 µM) | 29.4 ± 1.3** (n = 7) | 60.5 ± 3.9* (n = 7) |
| CN-Hb (1 µM) | 12.9 ± 3.0** (n = 6) | 80.7 ± 1.0**† (n = 4) |
| ACh (1 µM) | | 98.3 ± 0.6 (n = 10) |

*P < 0.01
**P < 0.001, Compared to Hb
†P < 0.001, Compared to ACh

EXAMPLE 4

Transduction of SNO-Hb Vasoactivity

Arterial red blood cells contain two physiologically important forms of hemoglobin: Hb(FeII)O$_2$ and Hb(FeIII) (Antonini, E. and Brunori, M. In *Hemoglobin and Myoglobin in Their Reactions with Ligands*, American Elsevier Publishing Co., Inc., New York, pp. 29–31 (1971)). Arterial-venous differences in the S-nitrosothiol content of intraerythrocytic Hb suggest that the NO group is released during red cell transit. Such findings raise the possibility of functional consequences, perhaps influenced by the redox state of heme and its occupation by ligand. SNO-Hb(FeII)O$_2$ was found to possess modest NO-like activity when tested in a vascular ring bioassay. Specifically, the contraction elicited by SNO-Hb(FeII)O$_2$ was less than that of native Hb(FeII)O$_2$, indicating that S-nitrosation partially reverses the contractile effects of Hb (FIG. 4A). By comparison, SNO-Hb (FeIII) was found to be a vasodilator (FIG. 4A). Notably, free NO was devoid of relaxant activity in the presence of Hb(FeII)O$_2$ or Hb(FeIII) (not shown).

Red blood cells contain millimolar concentrations of glutathione. As equilibria among RSNOs are rapidly established through RSNO/thiol exchange (Arnelle, D. R. and Stamler, J. S., *Arch. Biochem. Biophy.*, 318:279–285 (1995)), the vasoactivity of SNO-Hb was reassessed in the presence of glutathione. FIG. 4B illustrates that glutathione potentiated the vasodilator activity of both SNO-Hb(FeII)0$_2$ and SNO-Hb(FeIII). GSNO formation under these conditions (confirmed chemically and in bioassay experiments) appeared to fully account for this effect. Further kinetic analyses revealed that transnitrosation involving glutathione was more strongly favored in the equilibrium with SNO-Hb (FeIII) than SNO-Hb(FeII)O$_2$ (FIG. 4C). Given the findings of steady-state levels of SNO-Hb in red blood cells (Table 2 and FIG. 3A), these results suggest that 1) the equilibrium between naturally occurring RSNOs and Hb(cysβ93) lies toward SNO-Hb under physiological conditions; 2) that transnitrosation reactions involving SNO-Hb and GSH are likely to occur within red blood cells (in these studies, low molecular weight RSNOs have been found in erythrocytes loaded with SNO-Hb); and 3) that oxidation of the metal center of Hb shift the equilibrium toward GSNO, thereby potentially influencing bioactivity.

Additional mechanisms of NO group release from SNO-Hb were sought. Arterial-venous differences in levels of SNO-Hb raised the possibility that S—NO bond stability may be regulated by the changes in Hb conformation accompanying deoxygenation. To test this possibility, the rates of NO group release from SNO-Hb(FeII)O$_2$ and SNO-Hb(FeIII) were compared. Deoxygenation was found to enhance the rate of SNO-Hb decomposition (FIG. 2B). These rates were accelerated greatly by glutathione in a reaction yielding GSNO (FIG. 2B). The results illustrate that O$_2$-metal interactions influence S—NO affinity, and suggest a new allosteric function for Hb.

Figure 4D:
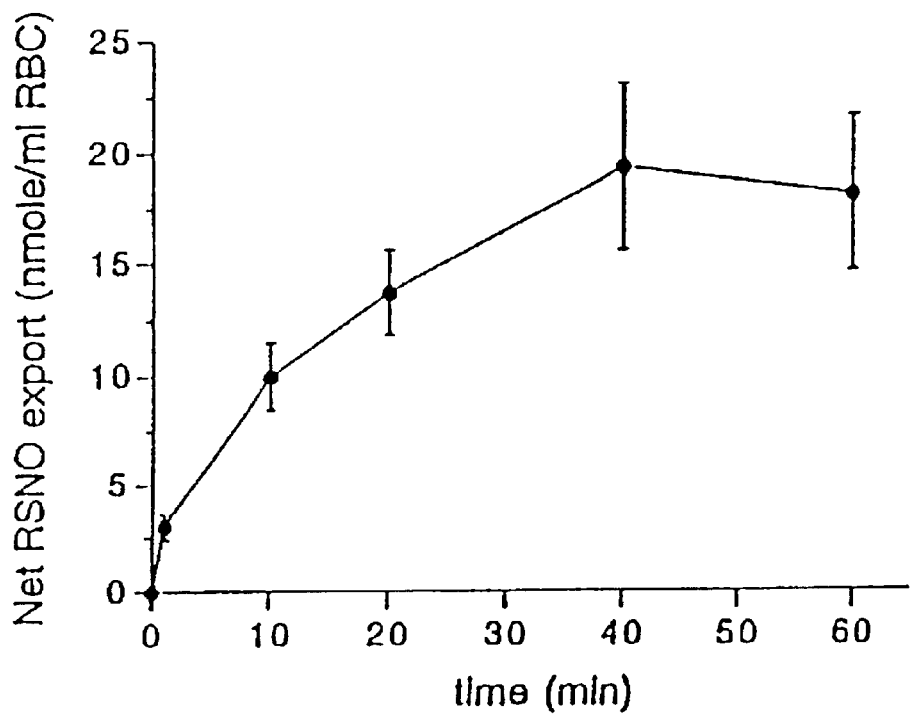
FIG. 4D is a graph of S-nitrosothiols exported from loaded red blood cells over time.

For SNO-Hb to be of physiological importance it must transduce its NO-related activity across the erythrocyte membrane. This possibility was explored by incubating erythrocytes containing SNO-Hb in physiologic buffer, and measuring the accumulation of extracellular RSNOs over time. FIG. 4D illustrates that red blood cells export low molecular weight (trichloroacetic acid soluble) S-nitrosothiols under these conditions. Importantly, the degree of hemolysis in these experiments was trivial (<0.5%), and correction for lysis did not significantly impact on rates of RSNO release. These results establish that an equilibrium exists between low molecular weight and protein RSNOs within the red cell, and that intracellular location is unlikely to be a limiting factor in the transduction of such NO-related activity to the vessel wall.

A. Concentration-Effect Responses of Different SNO-Hb Preparations

Contractile effects of Hb(FeII)O$_2$(▲) are shown to be partially reversed by S-nitrosation (SNO-Hb[FeII]O$_2$(■); P=0.02 by ANOVA vs Hb(FeII)O$_2$) (See FIG. 4A.). Oxidation of the metal center of SNO-Hb (SNO-Hb[FeIII](●)) converts the protein into a vasodilator (P<0.0001 by ANOVA vs. SNO-Hb[FeII]O$_2$), with potency comparable to that of other S-nitrosoproteins (Stamler, J. S., et al., *Proc. Natl. Acad. Sci. USA*, 89:444–448 (1992)). The contractile properties of Hb(FeIII) are shown for comparison (□); n=6–17 for each data point.

Methods

Details of the vessel ring bioassay have been published (Stamler, J. S., et al., *Proc. Natl. Acad. Sci. USA* 89:444–448 (1992)). SNO-Hb(FeII)O$_2$ preparations were synthesized with 10-fold excess S-nitrosocysteine (CYSNO) over Hb(FeII)O$_2$ protein (2% borate, 0.5 mM EDTA, ~15 min incubation), after which desalting was performed across Sephadex G-25 columns. CYSNO was synthesized in 0.5 N HCl, 0.5 mM EDTA and then neutralized (1:1) in 1 M phosphate buffer containing 0.5 mM EDTA. SNO-Hb(FeIII) preparations followed a similar protocol, but used Hb(FeIII) as starting material. The latter was synthesized by treatment of Hb(FeII)O$_2$ with excess ferricyanide, followed by desalting across G-25 columns. SNO-Hb concentrations were verified spectroscopically and the S-nitrosothiol content was determined by the method of Saville (Stamler, J. S., et al., *Proc. Nat. Acad. Sci USA* 89:444–448 (1992)). The S-NO/tetramer stoichiometry for both SNO-Hb preparations was ~2. Oxidation of the heme was undetectable by uv-spectophotometric methods.

B. Potentiation of SNO-Hb effects by Glutathione

Addition of glutathione (100 µM) to bioassay chambers potentiates the dose-response to both SNO-Hb(FeII)O$_2$(○) and SNO-Hb(FeIII)(●) (See FIG. 4B. n=6–12; p<0.0001 for both by ANOVA, compared with the respective tracings in FIG. 4A. Glutathione had a transient affect on baseline tone in some experiments, and did not significantly influence the response to Hb(FeII)O$_2$ (▲).

C. Transnitrosation Between SNO-Hb and Glutathione

Rates of NO group transfer from SNO-Hb (100 µM) to glutathione (10 mM) are displayed for SNO-Hb(FeII)O$_2$ (oxy) and SNO-Hb(FeIII) (met) (n=5). Data are presented as the amount of GSNO formed relative to the starting SNO-Hb concentration. The transfer is more rapid for SNO-Hb (FeIII) than SNO-Hb(FeII)O$_2$ (p<0.002 by ANOVA), suggesting that the GSNO/SNO-Hb equilibrium is shifted toward GSNO by formation of metHb.

Methods

Thiol/SNO-Hb exchange, forming GSNO, was verified chemically (Stamler, J. S., et al., *Proc. Natl. Acad. Sci. USA*, 89:444–448 (1992)) following trichloroacetic acid precipitation (n=5). These results were verified in separate experiments by measuring the residual SNO-Hb concentration, following separation of reaction mixtures across G-25 columns.

D. Export of S-Nitrosothiols by Red Blood Cells

Human red blood cells containing SNO-Hb are shown to export low molecular weight RSNOs over time. Hemolysis, which ranged from 0–<0.5% over one hour and did not correlate with rates of RSNO release, could account for only a trivial fraction of the measured extracellular RSNO.

Methods

Packed human red blood cells were obtained by centrifugation, washed, and resuspended in phosphate buffered saline containing 5 mM SNOCYS (0.5 mM EDTA, pH 7.4) for one hour. This results in a red cell preparation containing SNO-Hb (FeIIO$_2$/FeIII mixture) with a stoichiometry of 0.5 S-NO/tetramer. The red blood cells were then washed repeatedly to remove residual CYSNO (verified), and incubated in Krebs' solution (1:4). The accumulation of extracellular RSNO was measured over time by the method of Saville (Saville, B., *Analyst*, 83:670–672 (1958)). Hemolysis was determined by spectral analysis of red blood cell supernatants following centrifugation.

EXAMPLE 5

SNO-Hb Bioactivity In Vivo

Systemic administration of cell-free Hb results in hypertensive responses which have been attributed to NO scavenging by the heme (Vogel, W. M., et al., *Am. J. Physiol.* 251:H413–H420 (1986); Olsen, S. B., et al., *Circulation* 93:329–332 (1996)). To determine if SNO-Hb is free of this adverse affect, and to explore if in vitro mechanisms of NO release extend to the in vivo circumstance, we compared responses to Hb and SNO-Hb infused as a bolus into the femoral vein of anesthetized rats. As illustrated in FIG. 5, Hb(FeII)O$_2$ (200 nmol/kg) caused an increase in mean arterial pressure of 20±3 mm Hg (n=4; P<0.05). In contrast, SNO-Hb(FeII)O$_2$ did not exhibit hypertensive effects and SNO-Hb(FeIII) elicited hypotensive responses (FIG. 5). Thus, the profiles of these compounds in vivo closely resemble those seen in vitro (FIG. 4A). Moreover, to demonstrate that the physiological responses of red cells are comparable to those of cell-free Hb preparations, erythrocytes containing SNO-Hb were injected into the femoral vein of rats pretreated with L-NMMA (50 mg/kg) to deplete endogenous RSNOs. At levels of SNO-Hb comparable to those found in the normal rat (0.1–0.5 μM), SNO-Hb containing red blood cells elicited hypotensive responses (8±1 mm Hg; mean±SEM; n=9), whereas native (SNO-Hb depleted) red blood cells did not (P=0.001). These changes in mean blood pressure of ~10% are on the order of those that differentiate normotension from hypertension in man, and in the therapeutic range of some antihypertensive regimens. The effects of both Hb and SNO-Hb—whether cell-free or contained within red cells—were transient, suggesting that S-nitrosylation of Hb and metabolism of SNO-Hb may be occurring in vivo, with consequent restoration of blood pressure. The bioactivity of SNO-Hb in blood, where S—NO/heme stoichiometries approach 1:50,000, is a dramatic illustration of the resistance of this NO-related activity to Hb(Fe) inactivation.

In Vivo Effects of Cell-Free Hb and SNO-Hbs

Administration of 2–200 nmol/kg Hb(FeII)O$_2$ (as a bolus) into the femoral vein of a Sprague-Dawley rat is shown to increase mean arterial pressure in a dose-dependent manner. At 200 nmol/kg, mean arterial pressure increased by 25 mm Hg (20±3 mm Hg; n=4; P<0.05). Elevations in blood pressure reversed within 10–15 minutes. SNO-Hb(FeII)O$_2$ infusions (over the same dose range) are shown to ameliorate Hb(FeII)O$_2$-induced hypertension without causing overt changes in blood pressure. A similar response was seen at higher doses. By comparison, SNO-Hb(FeIII) infusions caused a significant fall in mean arterial pressure (pre 108±4 mm Hg; post 74±6 mm Hg, n=5; P<0.05) at the highest dose (200 nmol/kg). Hypotensive responses tended to be transient with blood pressure normalizing over 10 minutes. A fall in blood pressure was also seen with injection of erythrocytes containing SNO-Hb.

Methods

Rats were anesthetized by intraperitoneal injection of pentobarbital and the femoral arteries and veins accessed by local cut down. The artery was then cannulated and the blood pressure monitored continuously using a Viggo Spectramed pressure transducer attached to a Gould recorder. An IBM PC (DATA Q Codas) was used for data acquisition.

EXAMPLE 6

Loading of Red Blood Cells With S-Nitrosothiols

Incubation of rat erythrocytes with S-nitrosocysteine (equimolar to heme (5 mM); phosphate buffer pH 7.4, 25° C.) leads to rapid formation of intracellular S-nitrosothiols. MetHb does not form rapidly. Separation of cell content across G-25 columns establishes the formation of intraerythrocytic low molecular weight S-nitrosothiol, e.g. S-nitrosoglutathione, (GSNO). By 2 minutes, one can achieve as much as millimolar GSNO.

Method for Assay of RSNO

S-nitrosocysteine (5 mM) treated red blood cells are pelleted rapidly by centrifugation, washed three times, lysed in deionized water at 4° C., and the cytosolic fraction subjected to rapid desalting across G-25 columns. Intracellular RSNO is measured by the method of Saville and can be confirmed spectroscopically.

Effects on Blood Pressure From Loaded Red Blood Cells

Red blood cells treated with S-nitroscysteine (to produce SNO-RBCs) and introduced into the femoral vein of a Sprague-Dawley rat decreased mean arterial pressure in a dose-dependent manner. For red blood cells in which SNO-Hb was assayed at 0.3 μM (the endogenous in vivo SNO-Hb concentration), arterial pressure decreased by 8±1 mm Hg (mean±SEM for 9 experiments; p<0.001 compared to untreated red blood cell controls). For red blood cells in which SNO-Hb was assayed at 0.5 μM, arterial pressure decreased by 10 mm Hg. For red blood cells in which SNO-Hb was assayed at 0.1 μM (a sub-endogenous SNO-Hb concentration), arterial pressure decreased by 6 mm Hg. The administration of untreated red blood cells caused no effect or a slight increase in arterial blood pressure. Administration of L-monomethyl-L-arginine (L-NMMA; 50 mg/kg) caused an increase in blood pressure of about 20 mm Hg. Changes in blood pressure from a bolus administration of loaded red blood cells lasted 15–20 minutes.

Further Methods

Rats were anesthetized by intraperitoneal injection of pentobarbital and the femoral arteries and veins accessed by local cut down. The artery was then cannulated and the blood pressure monitored continuously using a Viggo Spectramed pressure transducer attached to a Gould recorder. An IBM PC (DATA Q Codas) was used for data acquisition.

EXAMPLE 7

Effects of SNO-Hb on Coronary Vasodilation Coronary Flow and Blood Pressure

SNO-Hb was synthesized as described in Example 4A. Completion of the reaction was determined as described in Example 4A. Twenty-four healthy mongrel dogs (25–30 kg) were anesthetized with intravenous thiamylal sodium (60–80 mg/kg) and subjected to left thoracotomy in the fourth intercostal space. The left circumflex coronary artery distal to the left atrial appendage was minimally dissected. A pair of 7-MHz piezoelectric crystals (1.5×2.5 mm, 15–20 mg) was attached to a Dacron backing and sutured to the adventitia on opposite surfaces of the dissected vessel segment with 6-0 prolene. Oscilloscope monitoring and on-line sonomicrometry (sonomicrometer 120-2, Triton Technology, San Diego, Calif.) were used to ensure proper crystal position. A pulse Doppler flow probe (10 MHz, cuff type) was implanted distal to the crystals. An inflatable balloon occluder was also placed distal to the flow probe. All branches of the circumflex artery between the crystals and the occluder were ligated. Heparin sodium-filled polyvinyl catheters were inserted into the left ventricular cavity via the apex, into the left atrium via the atrial appendage, and into the ascending aorta via the left internal thoracic artery. The catheters, tubing, and wires were tunnelled to a subcutaneous pouch at the base of the neck.

After a 10 to 15 day recovery period, the catheters and wires were exteriorized under general anesthesia, and 2–3 days later, each dog was given a bolus injection of SNO-Hb (0.4 mg) to evaluate vascular response. Two dogs that demonstrated <5% dilation of epicardial coronary vessels were excluded from subsequent studies, and two were excluded because of other technical reasons.

Dogs were trained and studied while loosely restrained and lying awake in the lateral recumbent position. The laboratory was kept dimly illuminated and quiet. Aortic pressure, left ventricular end-diastolic pressure dP/dt external coronary diameter and coronary flow were monitored continuously. In 10 dogs, 0.1 ml of SNO-Hb solution, 50 nm/kg, was injected via the left atrial catheter. To verify potential effects of solvent on vasculature, 0.1 ml injections of 30% ethanol in distilled water were given as vehicle control. Between injections, phasic coronary blood flow and coronary artery diameter were allowed to return to preinjection levels (minimum 15 minutes). Allowing a 15 minute period between injections resulted in no modification of repeated does injections. To assess the direct and potential flow mediated indirect vasodilation effects of SNO-Hb on the conductance vessels, the dose was repeated in 6 of 10 dogs with partial inflation of the adjustable occluder to maintain coronary blood flow at or slightly below preinjection levels. The response to acetylcholine chloride (Sigma-Chemical) was assessed in another group of 10 dogs following a similar protocol to that used for SNO-Hb.

Epicardial coronary diameter, coronary blood flow, heart rate, and aortic and left ventricular end-diagnostic pressures were compared before and after each SNO-Hb injection. The maximum changes in coronary dimension and blood flow were expressed as a function of increasing doses of SNO-Hb. The response of coronary dimension to increasing doses followed a characteristic sigmoid dose-response curve that could be described by the following equation $$\text{Effect} = \frac{\text{maximal effect} \times \text{dose}}{K_D + \text{dose}}$$

where $K_D$ is the drug-receptor complex dissociation constant and is the dose at which 50% of the maximum response ($EC_{50}$) is achieved. In each animal, a nonlinear least-squares regression ($r^2 > 0.90$) was performed on the dose-response data. The regression was constrained to the above equation. From the regression, values for maximum response and $K_D$ were obtained for each individual animal. The mean of these values was then calculated to obtain an average $K_D$ and maximum response for the study group. These values were used to generate a mean curve, which was plotted with the mean dose-response values. (See FIGS. 6A–6F.)

EXAMPLE 8

Endogenous Levels of S-nitrosohemoglobin and Nitrosyl(FeII)-Hemoglobin in Blood To determine if SNO-Hb is naturally occurring in the blood, and if so, its relationship to the $O_2$ transport capacity and nitrosylated-heme content of red cells, an analytical approach was developed to assay the S-nitrosothiol and nitrosyl-heme content of erythrocytes (Table 2). Arterial blood was obtained from the left ventricle of anesthetized rats by direct puncture and venous blood was obtained from the jugular vein and inferior vena cava. Hb was then purified from red cells and assayed for RSNO and (FeII)NO content. Arterial blood contained significant levels of SNO-Hb, whereas levels were virtually undetectable in venous blood (Table 2). Measurements made 45 minutes after infusion of the NO synthase inhibitor $N^\omega$-monomethyl-L-arginine (L-NMMA) (50 mg/kg), showed a depletion of SNO-Hb as well as total Hb-NO (82 and 50±18%, respectively; n=3–5; p<0.05). These data establish the endogenous origin of SNO-Hb, although some environmental contribution is not excluded. The arterial-venous distribution seen for SNO-Hb was reversed in the case of Hb(FeII)NO, which was detected in higher concentrations in partially deoxygenated (venous) erythrocytes (Table 2). Accordingly, the proportion of nitrosylated protein thiol and heme appears to depend on the oxygenation state of the blood. Consistent with these findings, Wennmalm and coworkers have shown that Hb(FeII)NO forms mainly in venous (partially deoxygenated) blood (Wennmalm, A., et al., Br. *J. Pharmacol.* 106(3):507–508 (1992)). However, levels of Hb(FeII)NO in vivo are typically too low to be detected (by EPR) and SNO-Hb is EPR-silent (i.e., it is not paramagnetic). Thus, photolysis-chemiluminesence represents an important technological advance, as it is the first methodology capable of making quantitative and functional assessments of NO binding to Hb under normal physiological conditions.

TABLE 2

Endogenous levels of S-nitrosohemoglobin and nitrosyl(FeII)-hemoglobin in blood

| Site | SNO-Hb (nM) | Hb(FeII)NO (nM) |
|---|---|---|
| Arterial | 311 ± 55* | 536 ± 99† |
| Venous | 32 ± 14 | 894 ± 126 |

*P < 0.05 vs venous,
†P < 0.05 for paired samples vs venous

Methods

Blood was obtained from the left ventricle (arterial) and jugular vein (venous) of anesthetized Sprague-Dawley rats.

Comparable venous values were obtained in blood from the inferior vena cava. Red blood cells were isolated by centrifugation at 800 g, washed three times in phosphate buffered saline at 4° C., lysed by the addition of 4-fold excess volume of deionized water containing 0.5 mM EDTA, and desalted rapidly across G-25 columns according to the method of Penefsky at 4° C. In 24 rats, Hb samples were divided in two aliquots which were then treated or not treated with 10-fold excess $HgCl_2$ over protein concentration as measured by the method of Bradford. Determinations of SNO-Hb and Hb(FeII)NO were made by photolysis-chemiluminescence as described below. In 12 additional rats, further verification of the presence of SNO-Hb was made by assaying for nitrite after $HgCl_2$ treatment. Specifically, samples (with and without $HgCl_2$) were separated across Amicon-3 (Centricon filters, m.w. cut off 3,000) at 4° C. for 1 h, and the low molecular weight fractions collected in airtight syringes containing 1 µM glutathione in 0.5 N HCl. Under these conditions, any nitrite present was converted to S-nitrosoglutathione, which was then measured by photolysis-chemiluminescence (detection limit~1 nM). SNO-Hb was present in all arterial samples, and levels determined by this method (286±33 nM) were virtually identical to and not statistically different from those shown in Table 2. In venous blood, SNO-Hb was undetectable (0.00±25 nM); levels were not statistically different from those given above.

Method for Assay of S-Nitrosohemoglobin

A highly sensitive photolysis-chemiluminescence methodology was employed. A somewhat similar assay has been used for measuring RSNOs (S-nitrosothiols) in biological systems (Gaston, B., et al., *Proc. Natl. Acad. Sci. USA* 90:10957–10961 (1993); Stamler, J. S., et al., Proc. Natl. Acad. Sci. USA 89:7675–7677 (1992)). The method involves photolytic liberation of NO from the thiol, which is then detected in a chemiluminesence spectrometer by reaction with ozone. The same principle of operation can be used to cleave (and measure) NO from nitrosyl-metal compounds (Antonini, E. and Brunori, M. In *Hemoglobin and Myoglobin in Their Reactions with Ligands*, American Elsevier Publishing Co., Inc., New York, pp. 29–31 (1971)). With adjustment of flow rates in the photolysis cell, complete photolysis of the NO ligand of Hb(FeII)NO could be achieved. Standard curves derived from synthetic preparations of SNO-Hb, Hb(FeII)NO, and S-nitrosoglutathione were linear (R>0.99), virtually superimposable, and revealing of sensitivity limits of approximately 1 nM. Two analytical criteria were then found to reliably distinguish SNO-Hb from Hb(FeII)NO: 1) signals from SNO-Hb were eliminated by pretreatment of samples with 10-fold excess $HgCl_2$, while Hb(FeII)NO was resistant to mercury challenge; and 2) treatment of SNO-Hb with $HgCl_2$ produced nitrite (by standard Griess reactions) in quantitative yields, whereas similar treatment of Hb(FeII)NO did not. UV/VIS spectroscopy confirmed that NO remained attached to heme in the presence of excess $HgCl_2$.

EXAMPLE 9

Inhibition of Platelet Aggregation by S-Nitrosohemoglobins

Methods to prepare human $HbA_0$ were as described in Example 1 "Methods" section. Methods to make SNO-Hb (FeII)$O_2$ were as described for Example 2A. Methods to make SNO-Hb(FeIII) were as in Example 1 (see parts B, C, and "Methods" in Example 1). Quantifications of SNO-hemoglobins were made as in Example 1 according to the method of Saville (Saville, B., *Analyst* 83:670–672 (1958)) and by the assay as described in Example 8, "Method for assay of S-nitrosohemoglobin."

Venous blood, anticoagulated with 3.4 nM sodium citrate, was obtained from volunteers who had not consumed acetylsalicylic acid or any other platelet-active agent for at least 10 days. Platelet-rich plasma was prepared by centrifugation at 150×g for 10 minutes at 25° C. and was used within 2 hours of collection. Platelet counts were determined with a Coulter counter (model ZM) to be 1.5 to 3×$10^8$ ml.

Aggregation of platelet-rich plasma was monitored by a standard nephelometric technique in which results have been shown to correlate with bleeding times. Aliquots (0.3 ml) of platelets were incubated at 37° C. and stirred at 1000 rpm in a PAP-4 aggregometer (Biodata, Hatsboro, Pa.). Hemoglobins were preincubated with platelets for 10 min and aggregations were induced with 5 µM ADP. Aggregations were quantified by measuring the maximal rate and extent of change of light transmittance and are expressed as a normalized value relative to control aggregations performed in the absence of hemoglobin.

The results of the aggregation assays are shown in FIGS. 7A, 7B and 7C. Standard deviations are shown as vertical bars. SNO-Hb[Fe(II)]$O_2$ causes some inhibition of platelet aggregation at the higher concentrations tested. SNO-Hb[Fe(III)] also inhibits platelet aggregation when present at concentrations of 1 µM and above, but to a much greater extent than SNO-Hb(Fe(II)]$O_2$.

EXAMPLE 10

Effect of SNO-Hbs on cGMP

Platelet rich plasma (PRP) was incubated with either hemoglobin, SNO-oxy Hb, or SNO-metHb for 5 min, after which the assay was terminated by the addition of 0.5 ml of ice cold trichloroacetic acid to 10%. Ether extractions of the supernatant were performed to remove trichloroacetic acid, and acetylation of samples with acetic anhydride was used to increase the sensitivity of the assay. Measurements of cyclic GMP were performed by radioimmunoassay (Stamler, J. et al., *Circ. Res.* 65:789–795 (1989)).

Results are shown in FIG. 8. For all concentrations of Hb tested (1, 10 and 100 µM), the concentration of cGMP measured for SNO-Hb(FeIII) was less than that of native Hb.

EXAMPLE 11

Polynitrosation of Hb

A. $HbA_0$ (oxy) was incubated with S-nitrosoglutathione at a ratio of 6.25 S-nitrosoglutathione/$HbA_0$ for 240 minutes at pH 7.4 at 25° C. and desalted over Sephadex G-25 columns. Spectra were run in the presence (spectrum B, FIG. 9A) and absence (spectrum A, FIG. 9A) of dithionite. The shift in the spectrum is indicative of 2 SNO groups/tetramer.

B. $HbA_0$ was incubated with 100-fold excess S-nitrosoglutathione over protein for 240 minutes at pH 9.2, followed by desalting over a G-25 column. A portion was then treated with dithionite. The spectra in FIG. 9B indicate that Hb has been nitrosated at multiple sites.

C. $HbA_0$ was treated with 100-fold excess S-nitroscysteine over tetramer at pH 7.4, 25° C. for 5–20 min. After various times of treatment, the protein was desalted over a G-25 column and treated with dithionite. The spectra show progressive polynitrosation of Hb with time (spectra A to F in FIG. 9C). After 5 minutes of treatment with 100-fold excess S-nitrosocysteine, 0.09 NO groups had added per tetramer (spectrum A of FIG. 9C); after 20 minutes, at least 4 NO groups had added (spectrum F). At intermediate time points, 0.4 NO groups (spectrum B), 1.58 NOs (spectrum C), 2.75 NOs (spectrum D) or 2.82 NOs had added per tetramer (spectrum E).

D. Rat Hb was treated with 100×S-nitrosoglutathione excess over tetramer for 3 hours at pH 7.4. The protein was then desalted by passage through a G-25 column. A portion of the desalted protein was treated with dithionite (spectrum B in FIG. 9D; the protein of spectrum A was left untreated by dithionite). Spectrum B in FIG. 9D is illustrative of a ratio of 6 RNOs/Hb.

E. A time course experiment tracking the extent of nitrosation of $HbA_0$ with time was performed (FIG. 9E). Treatment of $HbA_0$ was with 10×excess S-nitrosocysteine at pH 7.4, 25° C. or with 100×excess S-nitroscysteine under the same conditions. Analysis for SNO and NO was performed by the method of Saville and by UV spectroscopy as in Jia, L. et al., *Nature* 380:221–226 (1996). Under these conditions the heme is ultimately oxidized; the rate is time dependent.

Treatment with 10×excess S-nitrosocysteine nitrosylates only the thiol groups of the two reactive cysteine residues of HbAo. Inositol hexaphosphate is known to shift the allosteric equilibrium towards the T-structure (ordinarily, the deoxy form). Treatment with 100×excess nitrosates additional groups; i.e., the product has more than 2 NO groups/ tetramer.

EXAMPLE 12

Effect of $SNO-Hb(FeII)O_2$ on Blood Flow $SNO-Hb(FeII)O_2$, having a SNO/Hb ratio of 2, was prepared (from $HbA_0$) by reaction with S-nitrosothiol. Rats breathing 21% $O_2$ were injected (time 0) with Hbs prepared from $HbA_0$ as indicated in FIG. 10 (open circles, SNO-Hb (100 nmol/kg); filled circles, SNO-Hb (1000 nmol/kg); filled squares, unmodified Hb (1000 nmol/kg)). Three rats were used per experiment. Blood flow was measured in brain using the $H_2$ clearance method; microelectrodes were placed in the brain stereotactically. Concomitant $PO_2$ measurements revealed tissue $PO_2=20$. Thus, SNO-Hb improves blood flow to the brain under normal physiological conditions, whereas native Hb decreases blood flow. NO group release is promoted by local tissue hypoxia.

EXAMPLE 13

Effects of $SNO-Hb(FeII)O_2$, SNO-Hb(FeIII) and $(NO)_x$-Hb(FeIII) on Tension of Rabbit Aorta Hemoglobin was treated with either 1:1, 10:1 or 100:1 S-nitrosocysteine to Hb tetramer for 1 hour, processed as in Example 4. The products of the reactions done with 1:1 and 10:1 excess were assayed by the Saville assay and by standard spectrophotometric methods. The product of the reaction done at the 1:1 ratio is $SNO-Hb(Fe)O_2$; SNO-Hb (FeIII) is found following reaction with 1:10 excess CYSNO/tetramer.

The aortic ring bioassay was performed as described in Example 4. The product of the reaction in which a ratio of 100:1 CYSNO/Hb tetramer was used, contains 2 SNOs as well as NO attached to the heme. The potency of the 100:1 CYSNO/Hb product is much greater than that of SNO-Hb (FeIII) and is indicative of polynitrosation (see FIG. 11).

EXAMPLE 14

Effect of Oxygenation on Partially Nitrosylated Hemoglobin

The effect of oxygenation on partially nitrosylated Hb was examined by following spectral changes in the Soret region upon the addition of air to partially nitrosylated Hb. Hemoglobin A (17 $\mu$M) was deoxygenated by bubbling argon through a 1 ml solution in 100 mM phosphate (pH 7.4), for 45 minutes. Nitric oxide was added by injection of 0.5 $\mu$l of a 2 mM solution, stored under nitrogen. The final heme:NO ratio was 68:1. The solution was slowly aerated by sequential 50 $\mu$l injections of room air. FIG. 12 shows that the initial additions of air failed to produce a true isosbestic point, indicating changes in the concentrations of at least three absorbent species. Later additions of air did produce a true isosbestic point, indicative of the conversion of deoxyhemoglobin to oxyhemoglobin, with the loss of nitrosyl heme. The results show that nitrosylated Hb is not a stable end product.

EXAMPLE 15

Conversion of Nitrosylhemoglobin to SNO-Hemoglobin

The hypothesis that the nitric oxide was being transferred from the heme iron to t thiol residue, forming nitrosothiol upon oxygenation, was tested. Hemoglobin A (400 $\mu$M) was deoxygenated by bubbling argon through a 1 ml solution in 100 mM phosphate (pH 7.4), for 45 minutes.

Nitric oxide was added by injection of an appropriate volume of a 2 mM solution, stored under nitrogen, to achieve different NO/Hb ratios. The solutions were then exposed to air by vigorous vortexing in an open container. Samples were then analyzed by Saville assay and by chemiluminescence after UV photolysis. Data are shown as mean± standard error (n>3). FIG. 13 shows that S-nitrosothiol is formed in this manner, and that the efficiency of this reaction is greatest at high ratios of heme to nitric oxide. Amounts are highest at very high NO/Hb ratios, i.e., >2:1. This result implies that nitrosyl Hb entering the lung is converted into SNO-Hb, as under physiological conditions the ratio of heme to NO is high.

EXAMPLE 16

Effects Dependent upon Heme:NO Ratio

It was proposed that the binding of nitric oxide to the heme of the β chain was inherently unstable, and that the reason for lower yields of SNO-Hb at higher concentrations of nitric oxide, was a loss of bound nitric oxide as a result of this instability. Hemoglobin A (17.5 $\mu$M) was deoxygenated by bubbling argon through a 1 ml solution in 100 mM phosphate (pH 7.4), for 45 minutes. Nitric oxide was added by sequential injections of an appropriate volume of a 2 mM solution, stored under nitrogen. FIG. 14A: Difference spectra of the nitric oxide hemoglobin mixture and the starting deoxyhemoglobin spectrum are shown. FIG. 14B: The peak wavelength of the difference spectra plotted against the concentration of nitric oxide added to the solution. These data show that addition of small amounts of nitric oxide (heme:NO ratios of approximately 70:1) produce predominantly nitrosylhemoglobin and some oxidized hemoglobin. However, nitric oxide additions of the order of 10 $\mu$M result in the formation of oxidized hemoglobin. Heme:NO ratios at this point are approximately 7:1. As the concentration of nitric oxide is increased by further additions of nitric oxide, the predominant species formed becomes nitrosylhemoglobin (heme:NO ratio 1:1). The results in FIGS. 14A and 14B show that under anaerobic conditions, the addition of increasing quantities of nitric oxide to Hb results first in the production of nitrosylhemoglobin and then oxidized Hb (metHb). At very high levels of nitric oxide, nitrosylhemoglobin is once again seen as the nitric oxide first reduces metHb to deoxyHb (producing nitrite), then binds NO. This drives the conformational change of T-structure Hb to R-structure, stabilizing the β heme-nitric oxide bond. The appearance of oxidized Hb at heme to nitric oxide ratios of approximately 10:1 indicates the decay of the heme/NO bond to produce oxidized Hb and nitric oxide anion (nitroxyl). The presence of nitric oxide anion was confirmed by detection of $N_2O$ in the gas phase by gas chromatography mass spectrometry and by the production of $NH_2OH$.

EXAMPLE 17

Effects Upon Oxygenation of Nitrosyl-DeoxyHb

Hemoglobin A (20.0 mM) was deoxygenated by bubbling argon through a 1 ml solution in 100 mM phosphate (pH 7.4), for 45 minutes. In both FIG. 15A and FIG. 15B, the lowest to the highest spectra indicate the sequential additions of air. These are difference spectra in which the pure deoxyHb spectrum occurs at zero absorbance. The peak at 419 nm is from nitrosylhemoglobin; oxidized hemoglobin absorbs at 405 nm.

In the experiments shown in FIG. 15A, hemoglobin was gradually oxygenated by sequential additions of 10 µl of room air by Hamilton syringe. Spectra are shown as difference spectra from the initial deoxyhemoglobin spectrum. In the experiments shown in FIG. 15B, nitric oxide (1 µM) was added by injection of 0.5 µl of a 2 mM solution, stored under nitrogen. Final heme:NO ratio was 80:1. The solution was gradually oxygenated by sequential additions of 10 µl of room air. Spectra are shown as difference spectra from the initial deoxyhemoglobin spectrum. These data show the initial formation of a nitrosylhemoglobin peak, along with some formation of oxidized hemoglobin, which disappears after the addition of approximately 30 µl of air. The results indicate that a small quantity of nitrosyl Hb is formed upon addition of low ratios of nitric oxide to deoxy Hb, and that this nitrosyl Hb is lost upon oxygenation.

EXAMPLE 18

Role of β93Cys in Destabilizing Nitrosyl-Heme

Recombinant hemoglobins were obtained from Clara Fonticelli at the University of Maryland School of Medicine. β93Ala represents a single amino acid substitution within human hemoglobin A, whilst β93Cys represents a wild type control. Recombinant hemoglobin (5 µM containing either a wild type cysteine (β93Cys) or a mutant alanine (β93Ala) at position β93 was deoxygenated as in FIGS. 15A and 15B. Nitric oxide (1 µM) was added by injection of 0.5 µl of a 2 mM solution, stored under nitrogen. The final heme:NO ratio was 20:1. The solution was gradually oxygenated by sequential additions of 10 µl of room air. The absorption at 418 nm of difference spectra versus initial deoxyhemoglobin spectra is shown in FIG. 16. These data indicate that within the mutant, a nitrosyl adduct was formed that was not lost upon addition of room air. However, the nitrosyl adduct formed within the wild type was lost after addition of greater than 10 µl of room air. This shows that NO is not lost from this nitrosyl (FeII) heme in a mutant Hb that does not possess a thiol residue at position β93. Therefore, this thiol, which is in close proximity to the heme within the R-structure, is critical for destabilizing the heme nitric oxide bond.

EXAMPLE 19

SNO-Hb from Nitrosyl-Hb Driven by $O_2$

Hemoglobin A (400 µM) was prepared in a 1 ml solution, in 100 mM phosphate (pH 7.4). Nitric oxide was added by injection of an appropriate volume of a 2 mM solution, stored under nitrogen. The solutions were vortexed vigorously in an open container. Samples were then analyzed by Saville assay and by chemiluminescence after UV photolysis. The results in FIG. 17 show that S-nitrosothiol Hb can be formed from oxyHb, but that the efficiency of this formation is critically dependent upon the ratio of heme to nitric oxide.

EXAMPLE 20

Formation of Oxidized Hb Dependent on Protein Concentration

Hemoglobin A was diluted to the concentrations indicated by the different symbols in FIG. 18A and FIG. 18B, in 50 ml of 100 mM phosphate buffer (pH 7.4). Nitric oxide was added by sequential injections of an appropriate volume of a 2 mM solution, stored under nitrogen. After each injection, the absorbance at 415 and 405 nm was measured. The ratio of these two absorbances was used to calculate the percentage content of oxidized hemoglobin (FIG. 18A), and the absolute yield of oxidized hemoglobin (FIG. 18B). ♦ represents 1.26 µM hemoglobin, ■ represents 5.6 µM hemoglobin, ▲ represents 7.0 µM hemoglobin, X represents 10.3 µM hemoglobin, ✶ represents 13.3 µM hemoglobin, and ● represents 18.3 µM hemoglobin. These data show that only a small proportion of the nitric oxide added results in the formation of oxidized hemoglobin (<10%). Furthermore, this tendency to form oxidized hemoglobin is reduced at higher protein concentrations.

EXAMPLE 21

Effect of Ionic Strength and NO:Hb Ratio on Extent of MetHb Formation

We proposed that the degree of hydrogen bonding between bound oxygen and the distal histidine was critical in determining the degree of oxidation of hemoglobin by nitric oxide. Therefore, we examined the degree of oxidation of hemoglobin by nitric oxide in a variety of buffers. 5 ml of phosphate buffer containing 300 µM Hemoglobin A (~95% oxyHb) was placed in a 15 ml vial. Nitric oxide was added from a stock solution, 2 mM, stored under nitrogen. Immediately after nitric oxide addition, the absorbance at 630 nm was measured, and the concentration of oxidized (metHb) was plotted, using 4.4 as the extinction coefficient for metHb at 630 nm. Experiments were performed in 1 M, 100 mM, and 10 mM sodium phosphate buffer (pH 7.4). The data in FIG. 19 show higher oxidized hemoglobin formation in 1 M phosphate, which is indicative of a higher effective substrate concentration, as would be predicted by phosphate destabilization of the hydrogen bond between iron bound oxygen and the distal histidine. At the lowest concentrations of nitric oxide added, S-nitrosothiol was formed under all conditions (approximately 5 µM). Additions of nitric oxide at concentrations of 30 µM or greater resulted in the additional formation of nitrite. The presence of 200 mM borate within the buffer reduced oxidized hemoglobin and nitrite formation, whilst the presence of either 200 mM acetate or chloride increased the formation of oxidized hemoglobin and nitrite. Addition of nitric oxide to hemoglobin in 10 mM phosphate buffer at a ratio of less than 1:30 (NO:Hemoglobin A) resulted in the formation of S-nitrosothiol without production of oxidized hemoglobin. S-nitrosothiol formation was optimized by adding the nitric oxide to hemoglobin in 10 mM phosphate, 200 mM borate, pH 7.4. Therefore, the balance between oxidation and nitrosothiol formation is dependent upon the ratio of nitric oxide to hemoglobin and the buffer environment.

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A method of delivering NO or its biological equivalent to tissues in an animal or human, comprising administering to the animal or human an effective amount of nitrosylhemoglobin.

2. Method for making SNO-oxyhemoglobin, comprising adding NO to an aqueous solution of oxyhemoglobin and buffer having a pK of at least about 9.4, at a concentration of approximately 10 mM to 200 mM, at pH 7.4.

3. Method for making SNO-oxyhemoglobin, comprising adding NO to an aqueous solution of oxyhemoglobin in a approximately 10 mM phosphate buffer at pH 7.4.

4. Method for making S-nitrosohemoglobin comprising adding NO to oxyhemoglobin in an aqueous solution at pH 7.4 to 9.2 such that the ratio of NO:hemoglobin is less than about 1:30.

5. A method for producing SNO-oxyhemoglobin, said method comprising mixing nitric oxide and deoxyhemoglobin at pH 7.4 and at a heme:NO ratio of less than 10, and exposing the resulting solution to air.

6. A method for producing S-nitrosohemoglobin, said method comprising mixing nitric oxide dissolved in an aqueous solution and purified oxyhemoglobin at a heme:NO ratio of less than about 10 in aqueous buffer at pH 7.4.

* * * * *